(12) United States Patent
Meyerowitz et al.

(10) Patent No.: US 11,135,222 B2
(45) Date of Patent: Oct. 5, 2021

(54) AURORA KINASE INHIBITORS

(71) Applicant: The Regents of the University of California, Oakland, CA (US)

(72) Inventors: Justin Gabriel Meyerowitz, San Francisco, CA (US); William Clay Gustafson, San Francisco, CA (US); William A. Weiss, San Francisco, CA (US); Nicholas T. Hertz, San Francisco, CA (US); Kevan M. Shokat, San Francisco, CA (US)

(73) Assignee: THE REGENTS OF THE UNIVERSIITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/948,078

(22) Filed: Nov. 20, 2015

(65) Prior Publication Data

US 2016/0250211 A1    Sep. 1, 2016

Related U.S. Application Data

(63) Continuation of application No. PCT/US2014/039238, filed on May 22, 2014.

(60) Provisional application No. 61/826,409, filed on May 22, 2013.

(51) Int. Cl.
*A61K 31/506* (2006.01)
*C07D 403/12* (2006.01)

(52) U.S. Cl.
CPC .......... *A61K 31/506* (2013.01); *C07D 403/12* (2013.01)

(58) Field of Classification Search
CPC .......................... A61K 31/506; C07D 403/12
See application file for complete search history.

(56) References Cited

U.S. PATENT DOCUMENTS

| | | | |
|---|---|---|---|
| 4,861,760 A | 8/1989 | Mazuel et al. | |
| 4,911,920 A | 3/1990 | Jani et al. | |
| 5,212,162 A | 5/1993 | Missel et al. | |
| 5,403,841 A | 4/1995 | Lang et al. | |
| 2011/0237598 A1 | 9/2011 | Stadtmueller et al. | |
| 2011/0245249 A1 | 10/2011 | Wasnaire et al. | |
| 2011/0319436 A1 | 12/2011 | Walter et al. | |
| 2012/0202818 A1 | 8/2012 | Tao et al. | |

FOREIGN PATENT DOCUMENTS

| | | |
|---|---|---|
| EP | 2 754 659 A1 | 7/2014 |
| WO | WO-2010/031056 A2 | 3/2010 |
| WO | WO-2010/031056 A3 | 3/2010 |
| WO | WO-2013/033862 A1 | 3/2013 |

OTHER PUBLICATIONS

International Search Report dated Sep. 12, 2014, for PCT Application No. PCT/US2014/039238, filed May 22, 2014, 4 pages.
Written Opinion dated Sep. 12, 2014, for PCT Application No. PCT/US2014/039238, filed May 22, 2014, 8 pages.

*Primary Examiner* — Anna Pagonakis
(74) *Attorney, Agent, or Firm* — Mintz, Levin, Cohn, Ferris, Glovsky and Popeo, P.C.

(57) ABSTRACT

Disclosed herein inter alia are compositions and methods useful in the treatment of cancer and for modulating the activity of Aurora A kinase and/or a Myc family protein.

10 Claims, 47 Drawing Sheets

| | $R_2$ | $R_3$ | Aurora A $IC_{50}$ (nM) |
|---|---|---|---|
| CD532 | H | NH-C(O)-NH-C6H4-CF3 | 48 |
| CD12 | H | NH-C(O)-C6H4-CF3 | 360 |
| CD13 | H | C(O)-NH-C6H4-CF3 | 200 |
| CD15 | H3C | NH-C(O)-NH-C6H4-CF3 | 58 |
| CD16 | H3C | NH-C(O)-C6H4-CF3 | 320 |
| CD17 | H3C | C(O)-NH-C6H4-CF3 | 150 |

| | $R_1$ | $R_2$ | $R_3$ | Aurora A $IC_{50}$ (nM) |
|---|---|---|---|---|
| CD532 | cyclopentyl | H | NHC(O)NH-phenyl-CF₃ | 48 |
| CD22 | cyclohexyl | CH₃ | NHC(O)NH-phenyl-CF₃ | 840 |
| CD24 | cyclohexyl | CH₃ | NHC(O)NH-phenyl | 780 |
| CD25 | cyclopentyl | H | NHC(O)NH-phenyl | 59 |

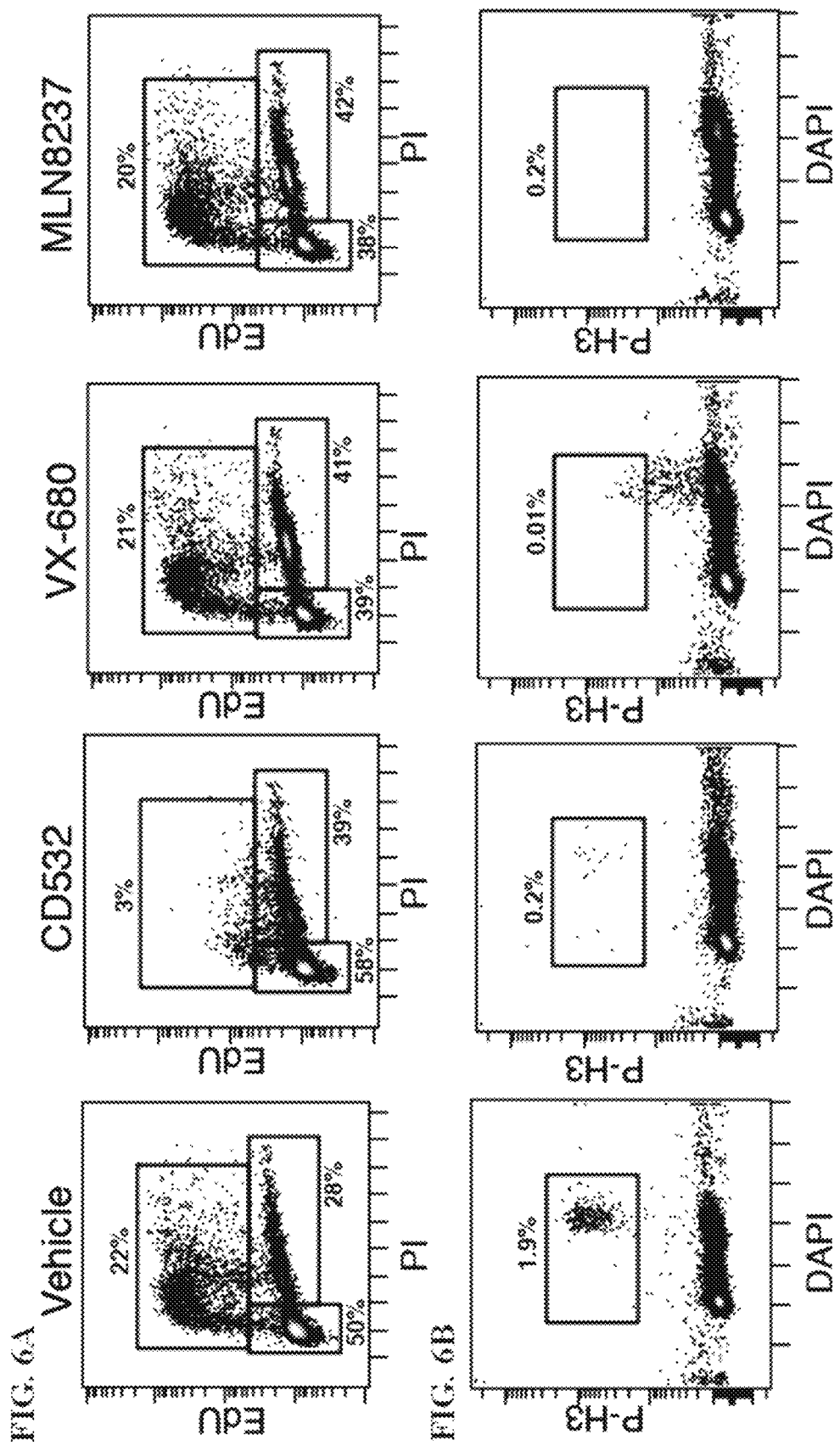

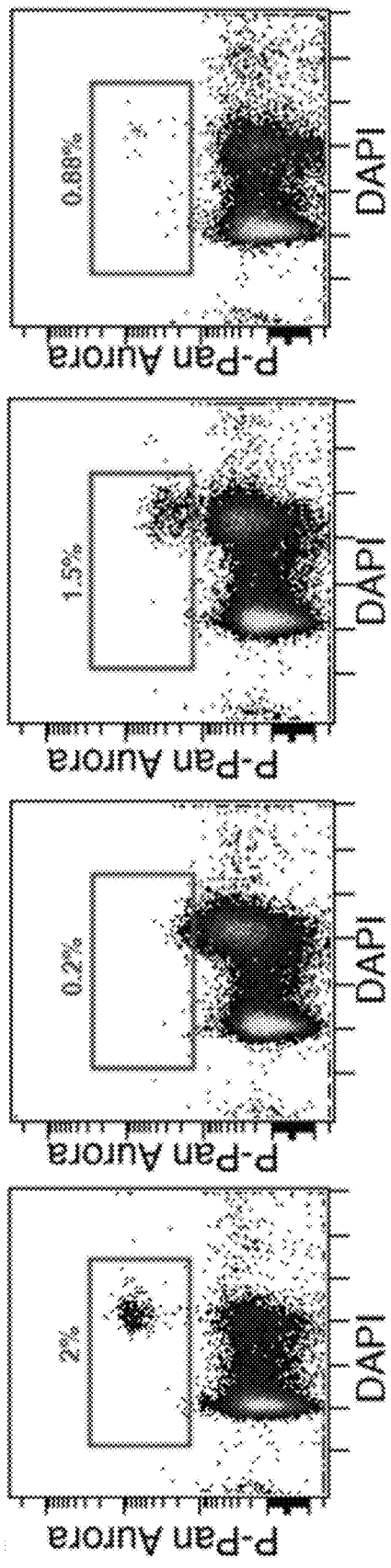
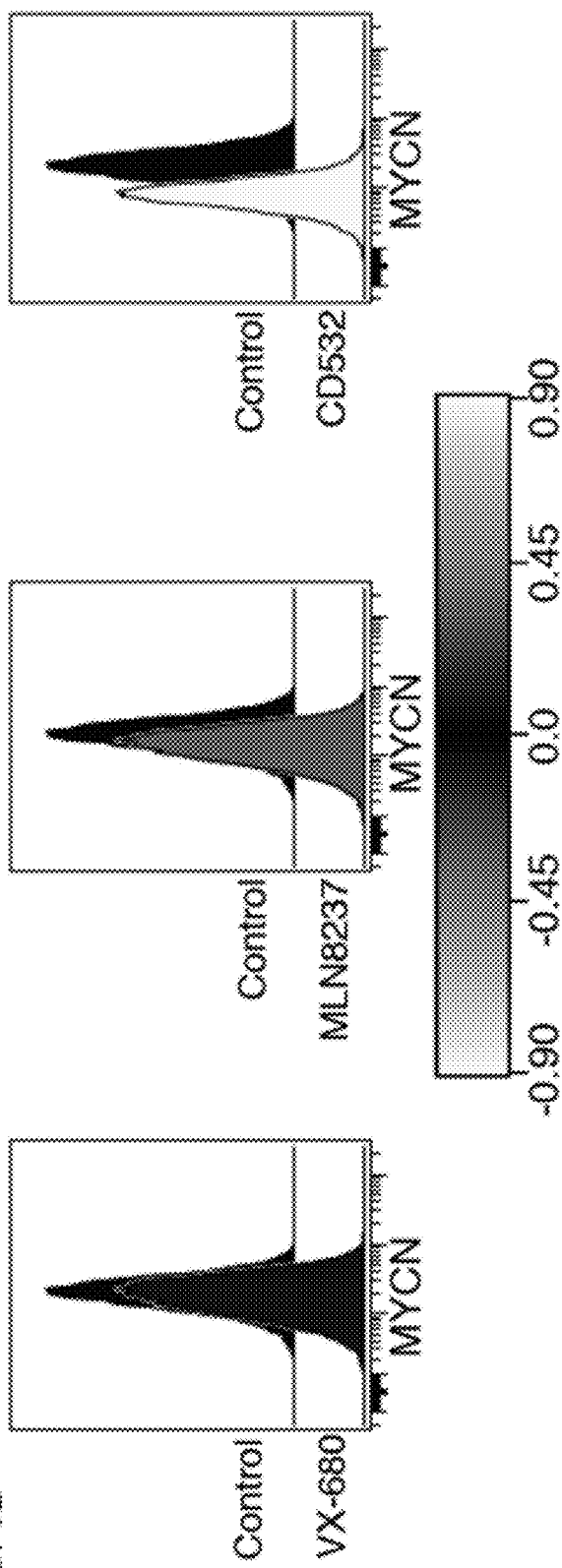
FIG. 6C
FIG. 6D

FIG. 11

| Name | R1 | R2 | R3 | IC50 (nM) Aurora A |
|---|---|---|---|---|
| NHCS3-2 | cyclopentyl | H | 3-CF3-phenyl amide | 48 |
| JM25 | cyclopentyl | H | phenyl amide | 59 |
| JM15 | cyclopentyl | CH3 | 3-CF3-phenyl amide | 58 |
| JM192 | cyclopentyl | H | 3-CF3, F-phenyl amide | 61 |
| JM134 | tetrahydrofuran | H | 3-CF3-phenyl amide | 192 |
| JM22 | cyclohexyl | CH3 | 3-CF3-phenyl amide | 838 |
| JM24 | cyclohexyl | CH3 | phenyl amide | 780 |
| JM12 | cyclopentyl | H | 3-CH3-phenyl amide | 363 |
| JM13 | cyclopentyl | H | 3-CH3-phenyl amide | 195 |
| JM16 | cyclopentyl | CH3 | 3-CH3-phenyl amide | 323 |
| JM17 | cyclopentyl | CH3 | 3-CH3-phenyl amide | 150 |

FIG. 12C
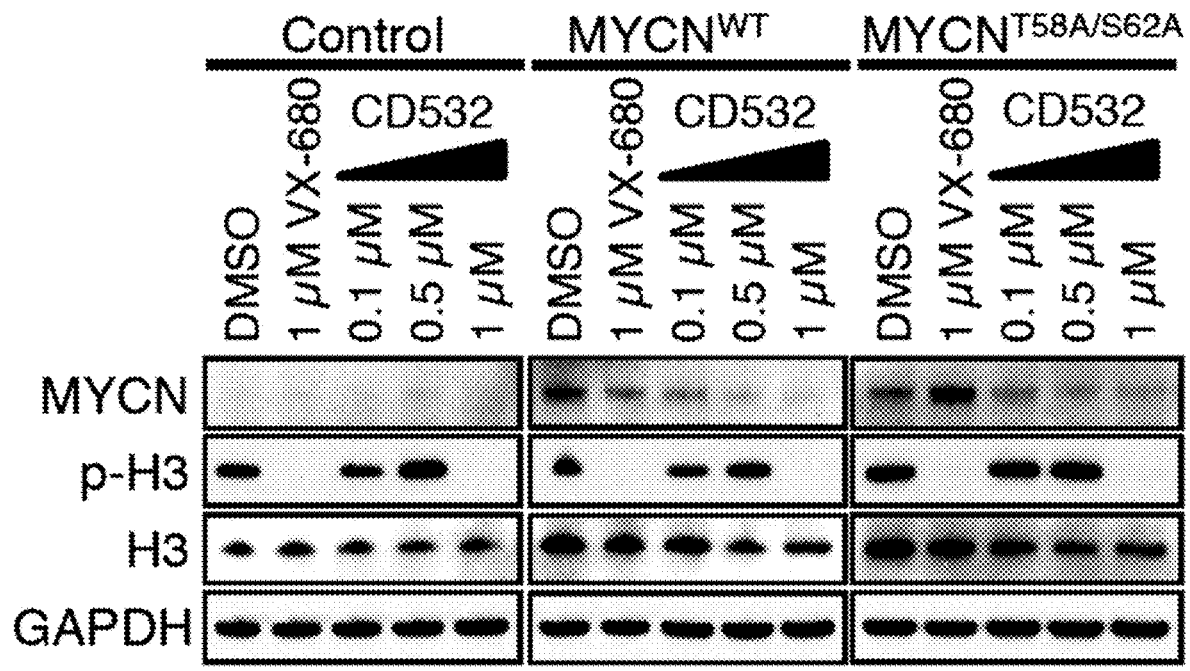
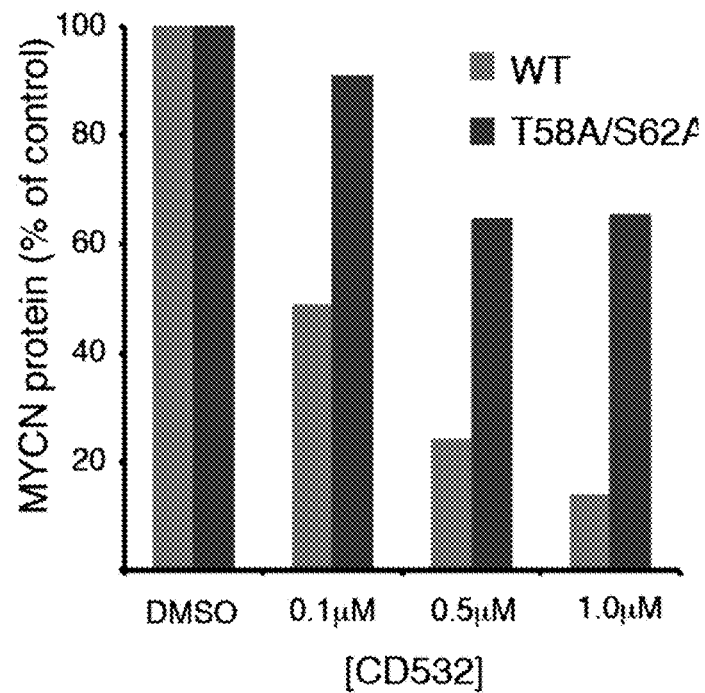

Kelly cells
24 hours, 1 μM

SUM142 Breast Cancer

RKO Colon Cancer

SMOwt medulloblastoma
25 mg/kg b.i.w.

\* p < 0.05
\*\* p < 0.005

AURORA KINASE INHIBITORS

CROSS-REFERENCE TO RELATED APPLICATIONS

This application is a continuation of PCT Application No. PCT/US2014/039238, filed on May 22, 2014, and entitled "AURORA KINASE INHIBITORS" which claims the benefit of U.S. Provisional Patent Application No. 61/826,409, filed on May 22, 2013, and entitled "AURORA KINASE INHIBITORS", the entirety of which are hereby incorporated by reference herein.

STATEMENT AS TO RIGHTS TO INVENTIONS MADE UNDER FEDERALLY SPONSORED RESEARCH AND DEVELOPMENT

This invention was made with government support under grant nos. K08NS079485, P01CA081403, and R01CA102321, awarded by the National Institutes of Health. The government has certain rights in the invention.

BACKGROUND OF THE INVENTION

MYC proteins are considered challenging drug targets, as they are composed almost entirely of two extended alpha helices with no apparent surfaces for small molecule binding. MYC also regulates as much as a third of the genome, with overexpression proposed to amplify cell-type specific gene expression rather than modulate a MYC-specific group of genes (Otto et al., 2009; Lin et al., 2012; Nie et al., 2012). Both MYC and MYC targets may be blocked through bromodomain inhibitors (Scrittori et al., 2001; Crosio et al., 2002; Liu et al., 2004; Ouchi, 2004; Filippakopoulos et al., 2010; Delmore et al., 2011; Mertz et al., 2011). Other methods, such as synthetic lethal screens for potential targets, have revealed druggable targets that may act downstream of MYC (Dietrich et al., 2010; Filomia et al., 2010; Toyoshima et al., 2012). However, using current chemical techniques, direct and efficient pharmacologic targeting of MYC transcription factors up to this time has proven challenging (Harrington et al., 2004; Prochownik and Vogt, 2010; Manfredi et al., 2011).

MYC genes contribute to a wide range of human tumors through overexpression, amplification, translocation, or stabilizing point mutations. The normal concentration of MYC in cells is tightly regulated at the level of protein stability through canonical upstream kinase signaling pathways, including PI3K/mTOR, CDK2, and MAPK. These kinases direct sequential phosphorylation and dephosphorylation of conserved residues in MYC proteins, which target them for ubiquitination and degradation by the proteasome (reviewed in (Gustafson and Weiss, 2010)). Thus, Aurora Kinase A alone, and MYCN, represent attractive cancer targets. Disclosed herein, inter alia, are solutions to these and other problems in the art.

BRIEF SUMMARY OF THE INVENTION

In one aspect is a compound, or a pharmaceutically acceptable salt thereof, having the formula:

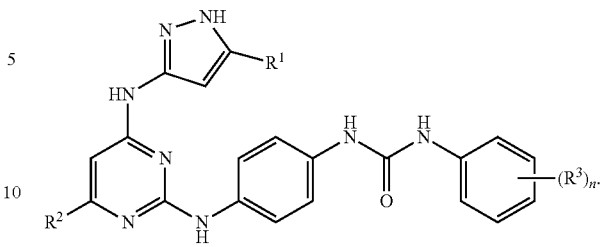

In formula (I), $R^1$ is a substituted or unsubstituted $C_5$ cycloalkyl, substituted or unsubstituted heterocycloalkyl, or substituted or unsubstituted 5 to 6 membered heteroaryl. $R^2$ is hydrogen, halogen, —$CF_3$, —$CCl_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCH_3$, —$OCF_3$, —$OCHF_2$, —C(O)$CH_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently halogen, —$CF_3$, —$CCl_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCH_3$, —$OCF_3$, —$OCHF_2$, —C(O)$CH_3$, unsubstituted alkyl, or unsubstituted heteroalkyl. The symbol n is independently an integer from 0 to 5.

Also provided herein are pharmaceutical compositions. In one aspect, the pharmaceutical composition includes a pharmaceutically acceptable excipient and a compound, or a pharmaceutically acceptable salt thereof, as described herein, including embodiments thereof.

Provided herein are methods of modulating the level of activity of Aurora A kinase. In one aspect, the method includes contacting the Aurora A kinase with an effective amount of a compound, or a pharmaceutically acceptable salt thereof, as described herein, including embodiments or in any examples, tables, or figures (e.g. compound of formula (I)).

Also provided are methods of modulating the level of activity of a Myc family (e.g. c-Myc, N-Myc, or L-Myc, or human Myc) protein in a cell. In one aspect, the method includes contacting the cell with an effective amount of a compound, or a pharmaceutically acceptable salt thereof, as described herein, including embodiments or in any examples, tables, or figures (e.g. compound of formula (I)).

Provided herein are methods of treating a Myc family (e.g. c-Myc, N-Myc, L-Myc, or human Myc) protein pathway associated cancer in a patient in need of such treatment. In one aspect, the method includes administering a therapeutically effective amount of a compound, or a pharmaceutically acceptable salt thereof, as described herein, including embodiments or in any examples, tables, or figures (e.g. compound of formula (I)).

BRIEF DESCRIPTION OF THE DRAWINGS

(FIG. 1A) Both VX-680-like diaminopyrimidine and a PP1-like pyrazolopyrimidine scaffolds were used for initial screening panel; Cell lines were treated for 24 hrs with 1 µM of 32 different compounds predicted to bind to Aurora A and modulate tertiary structure. Extracts were examined by western blot for MYCN and phospho-histone H3 expression, in (FIG. 1B) Kelly cells (quantitation on the right expressed as percent of control, additional blots in FIG. 5) and (FIG. 1C) a selected sub-panel of compounds was tested against SK-N-BE(2) cells (quantitation on the right expressed as percent of control) (FIG. 1D) Dose response of SK-N-BE(2) cells to increasing concentrations of CD532, MLN8237, and VX-680 (also in SMS-KCN cells and Kelly cells, FIGS. 15A and 15B); Dose responses of MLN8237 and CD532 at 72 hrs using a cyquant assay in (FIG. 1E) SKN-BE(2) and (FIG. 1F) Kelly MYCN-amplified neuroblastoma cells.

(FIG. 2A) Chemical structure of CD532 and surface representations of Aurora A Apo and of Aurora A bound to CD532; (FIG. 2B) CD532 in ATP binding pocket, overlaid with electron density before ligand fitting; (FIG. 2C) Interactions between CD532 (red), the DFG motif (D274) and β1/β2 (K141-V147) (FIG. 2D) Displacement of glycine rich loop in drug-bound structure as compared to Apo due to drug binding; (FIGS. 2E and F) Displaced α-C helix allows network of polar contacts between E181, R255, and DFG motif and (FIG. 2G) stabilization of inactive orientation of the activation loop (activation loop in balls); Structural comparisons are all C-terminal alignments.

(FIG. 3A) Chemical structures of CD compounds, VX-680, MLN8054, and MLN8237; (FIG. 3B) immunoblot and table) Effect of replacement of critical urea moiety with amides and substitution at the 6-position of pyrimidine; (FIG. 3C) Hydrophobic packing of cyclopentyl of CD532 between V147, L194, and gatekeeper L210; (FIG. 3D immunoblot and table) Effect of substitution of hydrophobic ring or des-trifluoromethyl; All treatments were of SK-NBE(2) cells for 24 hrs at 1 µM of compound.

(FIG. 4A) Angle between α-carbons of T333, E308, and A172 of Aurora A Apo (4J8N), Aurora A with VX-680 (3E5A), Aurora A with MLN8054 (2WTV), and Aurora A with CD532 (4J8M); (FIG. 4B) Comparison of binding modes of VX-680 and CD532 showing identical hinge binding; (FIG. 4C) Immunoblot of MYCN protein after 24 hr treatment of SK-N-BE (2) cells with VX-680, MLN8237, and CD532.

(FIG. 5A) Screening and characterization of conformation disrupting Aurora A inhibitor (CD) compounds; Screen of Kelly MYCN-amplified cells treated for 24 hrs with 1 uM of 32 different compounds predicted to bind to Aurora A and modulate tertiary structure. Extracts examined by western blot for MYCN and phospho-histone H3 expression, quantitation on right (additional blot FIG. 1B, quantitation FIG. 1B); (FIG. 5B) Representative sigmoidal dose response curve and (FIG. 5C) 32P ATP blot of CD532 against Aurora A; Enzyme was either full-length or kinase domain-only Aurora A, and substrate was either full-length purified Histone H3 or target oligopeptide; (FIG. 5D) Immunoprecipitation of Aurora A and immunoblot for p-Aurora A (T288) after 2 hrs treatment of IMR32 neuroblastoma cells with CD532.

FIGS. 6A-D. CD532 inhibits Aurora A kinase activity, downregulates MYCN, and blocks S phase entry by flow cytometry: Cells were treated for 6 hrs with the indicated drugs at 1 µM and EdU was added 1 hr prior to harvest to measure s-phase (FIG. 6A) cell cycle by EdU incorporation and propidium iodide staining (FIG. 6B) phospho-histone H3 (FIG. 6C) pan-Aurora phosphorylation (A, B, and C isoforms) and (FIG. 6D) MYCN protein.

(FIG. 7A) SMS-KCN cells or (FIG. 7B) Kelly cells were treated for 24 hrs with indicated of CD532, MLN8237, MLN8054 or VX-680 and analyzed by immunoblot for the indicated proteins.

(FIG. 10B) JM134 shows decreased binding affinity to Aurora A but maintains the protein conformation-altering chemical moieties that effect destabilization of MYCN; FIG. 10C The 5-fold increase in biochemical $IC_{50}$ against Aurora A of JM134 compared to NHC532 (CD532) arises from the alteration of the hydrophobic cyclopentyl moiety to a less hydrophobic 2-furan (FIG. 9; $IC_{50}$ values in FIG. 11). This decrease in active-site affinity of JM134 for Aurora A is reflected in the higher level of p-Histone H3 in JM134-treated cells as compared to NHC532-treated; however, JM134 treatment still decreases MYCN levels (though not as completely) as NHC532 (CD532), which emphasizes the importance of the biphenyl urea and 3-trifluoromethyl to give rise to MYCN destabilization.

FIG. 11. List of compounds generated and biochemical activity against Aurora A: The compound nomenclature below contains CD or JM as the two-letter prefix before compound number, however, the compound numbers (but not letters) still correspond to the compound numbers with a different prefix.

FIGS. 12A-C. Degradation of MYCN is proteasome-dependent and requires phosphorylation of MYCN: (FIG. 12A) Time dependence of MYCN protein loss in SK-N-BE (2) cells due to treatment with MLN8237 or CD532 performed at 1 µM; (FIG. 12B) CD532 dose dependence of MYCN protein loss in the absence or presence of proteasomal inhibition; (FIG. 12C) Immunoblot showing the effect of compounds at indicated concentrations for 24 hrs on protein levels of wild-type vs. T58A/S62A degradation-resistant MYCN in SHEP cells.

(FIG. 13A) Quantification of cell cycle of SK-N-BE(2) cells treated with CD532 (1 µM, 4 hr), MLN8237 (0.1 µM, 4 hr), JQ1 (2 µM, 24 hr), or MLN8237 (0.1 µM, 4 hr) in combination with JQ1 (2 µM, 24 hr); Corresponding scatter plots to (FIG. 13A) in FIG. 18A; Viability of SHEP cells transduced with MYCN or GFP after 72 hrs of treatment with (FIG. 13B) CD532 or (FIG. 13C) MLN8237; (FIG. 13D) Gene set enrichment analysis of 87 cancer cell lines against CD532 dose response showing enrichment of MYC-like gene expression profiles in susceptible lines, negative correlation between MYC genes up and $EC_{50}$ and positive correlation between MYC genes down and $EC_{50}$ (FIGS. 13 E and F) Western blot and quantification of tumors from mice treated daily for 2 days with 60 mg/kg CD532.

(FIG. 14C) Quantification of Aurora A/MYCN binding from triplicate experiments; CD532 causes complete and dose-dependent loss of Aurora A/MYCN interaction, whereas MLN8237 causes partial loss of interaction, consistent with CD532 conferring a larger magnitude scaffold disruption of Aurora A with a higher biochemical $IC_{50}$ for kinase inhibition compared to MLN8237.

(FIG. 17A) Scatter plots of EdU staining vs DAPI and pMPM2 staining: Raw data corresponding with cell cycle bar graphs in FIG. 13A; (FIG. 17B) Immunoblot demonstrating loss of MYCN in response to treatment with JQ1 and CD532 in SK-N-BE(2) cells corresponding to cell cycle data in FIG. 18A and FIG. 13A; (FIG. 17C) Pharmacokinetics of CD532 in mice; CD532 was delivered through intraperitoneal injection at 20 mg/kg and serum levels were measured at 1, 2, 4, 8, and 24 hrs; (FIG. 17D) Quantitation of S-phase fraction and (FIG. 17E) dot plot of SHEP non-MYCN-expressing neuroblastoma transduced with MYCN or mutationally-stabilized MYCNT58A/S62A and treated with MLN8237 or CD532 for 6 hrs.

(FIG. 18A) Plot of $EC_{50}$ vs MYC+ MYCN mRNA expression; Comparison of $EC_{50}$ values between MYCN amplified vs non-amplified cancer cell lines for (FIG. 18B) CD532 (FIG. 18C) JQ1 and (FIG. 18D) VX-680.

(FIG. 19A) SK-N-BE(2) cells were treated with CD532 for 2 hrs before immunoprecipitation of MYCN and immunoblot for Aurora A or MAX; (FIG. 19.B) Quantitation of MYCN-Aurora A and MYCN-MAX interactions in response to increasing concentration of CD532.

DETAILED DESCRIPTION OF THE INVENTION

Figure 1A:
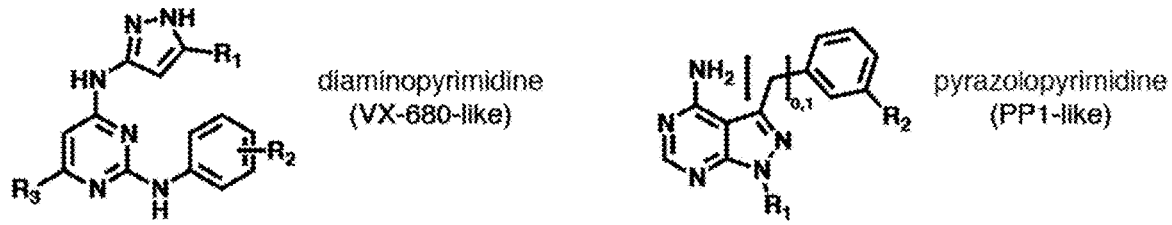
FIGS. 1A-F. Screening and characterization of conformation disrupting Aurora A inhibitor (CD) compounds.

MYC genes contribute to a range of cancers including for example neuroblastoma, where amplification of MYCN confers a poor prognosis. Proteolytic degradation of MYCN protein is regulated in part by a kinase-independent function of Aurora Kinase A. Described herein is a class of inhibitors that disrupts the native conformation of Aurora A and causes degradation of MYCN protein across MYCN-expressing neuroblastoma cell lines. Comparison of co-crystal structures with structure-activity relationships across multiple inhibitors and chemotypes, coupled with mechanistic studies and biochemical assays, delineates an Aurora A conformation-specific effect on proteolytic degradation of MYCN, rather than simple nanomolar-level inhibition of Aurora Kinase A kinase activity. This new class of inhibitors, which disrupts stabilizing interactions between Aurora A and MYCN, describes agents useful for targeting MYCN-driven cancers. A novel class of compounds induces a dramatic shift in the structure of Aurora A. CD532 potently inhibits Aurora Kinase A and causes rapid loss of MYCN protein.

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Alkyl is not cyclized. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Alkylene is not cyclized. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. Heteroalkyl is not cyclized. The heteroatom(s) O, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—O$CH_3$ and —$CH_2$—O—Si($CH_3$)$_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. Heteroalkylene is not cyclized. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively, wherein the carbons making up the ring or rings do not necessarily need to be bonded to a hydrogen due to all carbon valencies participating in bonds with non-hydrogen atoms. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S(O$_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C(O)NR"NR'''R'''', —CN, —NO$_2$, in a number ranging from zero to (2m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R',—C(O) NR'R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C(O)NR"NR'''R'''', —CN, —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R'''' groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:
(i) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and
(ii) alkyl, heteroalkyl, cycloalkyl, heterocycloalkyl, aryl, heteroaryl, substituted with at least one substituent selected from:
(a) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and
(b) alkyl, heteroalkyl, cycloalkyl, heterocycloalkyl, aryl, heteroaryl, substituted with at least one substituent selected from: oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —$NHC(O)NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents than are the corresponding free base forms. In other cases, the preparation may be a lyophilized powder that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It is apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol "⌇" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat cancer associated with a Myc family (e.g. c-Myc, N-Myc, L-Myc, or human Myc) protein pathway. For example certain methods herein treat cancer by decreasing a symptom of cancer. Symptoms of cancer would be known or may be determined by a person of ordinary skill in the art. The term "treating" and conjugations thereof, include prevention of an injury, pathology, condition, or disease (e.g. preventing the development of one or more symptoms of a Myc family (e.g. c-Myc, N-Myc, L-Myc, or human Myc) protein pathway associated cancer).

An "effective amount" is an amount sufficient to accomplish a stated purpose (e.g. achieve the effect for which it is administered, treat a disease, reduce enzyme activity, increase enzyme activity, reduce protein function, reduce protein stability, increase protein degradation, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist (inhibitor) required to decrease the activity of an enzyme or protein relative to the absence of the antagonist. An "activity increasing amount," as used herein, refers to an amount of agonist (activator) required to increase the activity of an enzyme or protein relative to the absence of the agonist. A "function disrupting amount," as used herein, refers to the amount of antagonist (inhibitor) required to disrupt the function of an enzyme or protein relative to the absence of the antagonist. A "function increasing amount," as used herein, refers to the amount of agonist (activator) required to increase the function of an enzyme or protein relative to the absence of the agonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

The term "associated" or "associated with" in the context of a substance or substance activity or function associated with a disease (e.g. cancer) means that the disease (e.g. cancer) is caused by (in whole or in part), or a symptom of the disease is caused by (in whole or in part) the substance or substance activity or function. For example, a symptom of a disease or condition associated with a Myc family (e.g. c-Myc, N-Myc, L-Myc, or human Myc) protein pathway activity may be a symptom that results (entirely or partially) from an increase in the level of activity of a Myc family (e.g. c-Myc, N-Myc, L-Myc, or human Myc) protein pathway. As used herein, what is described as being associated with a disease, if a causative agent, could be a target for treatment of the disease. For example, a disease associated with an increase in the level of activity of a Myc family (e.g. c-Myc, N-Myc, L-Myc, or human Myc) protein pathway, may be treated with an agent (e.g. compound as described herein) effective for decreasing the level of activity of a Myc family (e.g. c-Myc, N-Myc, L-Myc, or human Myc) protein pathway. For example, a disease associated with a decrease in a Myc family (e.g. c-Myc, N-Myc, L-Myc, or human Myc) protein pathway, may be treated with an agent (e.g. compound as described herein) effective for increasing the level of activity of a Myc family (e.g. c-Myc, N-Myc, L-Myc, or human Myc) protein pathway.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme (e.g. a component of a Myc family (e.g. c-Myc, N-Myc, L-Myc, or human Myc) protein pathway). In some embodiments contacting includes allowing a compound described herein to interact with a protein or enzyme that is involved in a signaling pathway.

As defined herein, the term "inhibition", "inhibit", "inhibiting" and the like in reference to a protein-inhibitor (e.g. antagonist) interaction means negatively affecting (e.g. decreasing) the level of activity or function of the protein (e.g. a component of a Myc family (e.g. c-Myc, N-Myc, L-Myc, or human Myc) protein pathway, Aurora A kinase, Myc family protein) relative to the level of activity or function of the protein (e.g. a component of a Myc family (e.g. c-Myc, N-Myc, L-Myc, or human Myc) protein pathway, Aurora A kinase, Myc family protein) in the absence of the inhibitor. In some embodiments inhibition refers to reduction of a disease or symptoms of disease (e.g. cancer associated with an increased level of activity of a component of a Myc family (e.g. c-Myc, N-Myc, L-Myc, or human Myc) protein pathway). In some embodiments, inhibition refers to a reduction in the level of activity of a signal transduction pathway or signaling pathway (e.g. a Myc family (e.g. c-Myc, N-Myc, L-Myc, or human Myc) protein pathway). Thus, inhibition may include, at least in part, partially or totally blocking stimulation, decreasing, preventing, or delaying activation, or inactivating, desensitizing, or down-regulating signal transduction or enzymatic activity or the amount of a protein (e.g. a component of a Myc family (e.g. c-Myc, N-Myc, L-Myc, or human Myc) protein pathway). Inhibition may include, at least in part, partially or totally decreasing stimulation, decreasing activation, or deactivating, desensitizing, or down-regulating signal transduction or enzymatic activity or the amount of a protein (e.g. a component of a Myc family (e.g. c-Myc, N-Myc, L-Myc, or human Myc) protein pathway) that may modulate the level of another protein or modulate cell survival (e.g. decreasing the level of activity of a component of a Myc family (e.g. c-Myc, N-Myc, L-Myc, or human Myc) protein pathway may decrease cancer cell survival in cells that may or may not have an increase in the level of activity of a component of a Myc family (e.g. c-Myc, N-Myc, L-Myc, or human Myc) protein pathway relative to a non-disease control).

As defined herein, the term "activation", "activate", "activating" and the like in reference to a protein-activator (e.g. agonist) interaction means positively affecting (e.g. increasing) the activity or function of the protein (e.g. a component of a Myc family (e.g. c-Myc, N-Myc, L-Myc, or human Myc) protein pathway, Aurora A kinase, Myc family protein) relative to the activity or function of the protein (e.g. a component of a Myc family (e.g. c-Myc, N-Myc, L-Myc, or human Myc) protein pathway, Aurora A kinase, Myc family protein) in the absence of the activator (e.g. compound described herein). In some embodiments, activation refers to an increase in the activity of a signal transduction pathway or signaling pathway (e.g. a Myc family (e.g. c-Myc, N-Myc, L-Myc, or human Myc) protein pathway). Thus, activation may include, at least in part, partially or totally increasing stimulation, increasing or enabling activation, or activating, sensitizing, or up-regulating signal transduction or enzymatic activity or the amount of a protein (e.g. a component of a Myc family (e.g. c-Myc, N-Myc, L-Myc, or human Myc) protein pathway) decreased in a disease (e.g. level of a component of a Myc family (e.g. c-Myc, N-Myc, L-Myc, or human Myc) protein pathway associated with cancer). Activation may include, at least in part, partially or totally increasing stimulation, increasing or enabling activation, or activating, sensitizing, or up-regulating signal transduction or enzymatic activity or the amount of a protein (e.g. a component of a Myc family (e.g. c-Myc, N-Myc, L-Myc, or human Myc) protein pathway) that may modulate the level of another protein or modulate cell survival (e.g. increasing the level of activity of a component of a Myc family (e.g. c-Myc, N-Myc, L-Myc, or human Myc) protein pathway may decrease cancer cell survival in cells that may or may not have a reduction in the level of activity of a component of a Myc family (e.g. c-Myc, N-Myc, L-Myc, or human Myc) protein pathway relative to a non-disease control).

The term "modulator" refers to a composition that increases or decreases the level of a target molecule or the function of a target molecule. In some embodiments, a modulator of a component of a Myc family (e.g. c-Myc, N-Myc, L-Myc, or human Myc) protein pathway (e.g. Aurora A kinase, Myc family protein) is a compound that reduces the severity of one or more symptoms of a disease associated with a component of a Myc family protein pathway (e.g. disease associated with an increase of the level of activity or amount of a component of a Myc family (e.g. c-Myc, N-Myc, L-Myc, or human Myc) protein pathway (e.g. Aurora A kinase, Myc family protein), for example cancer) or a disease that is not caused by a component of a Myc family protein but may benefit from modulation of the level of activity of amount of a component of a Myc family (e.g. c-Myc, N-Myc, L-Myc, or human Myc) protein pathway (e.g. Aurora A kinase, Myc family protein). In embodiments, a modulator of the level of activity or amount of a component of a Myc family (e.g. c-Myc, N-Myc, L-Myc, or human Myc) protein pathway (e.g. Aurora A kinase, Myc family protein) is an anti-cancer agent.

"Anti-cancer agent" is used in accordance with its plain ordinary meaning and refers to a composition (e.g. compound, drug, antagonist, inhibitor, modulator) having anti-neoplastic properties or the ability to inhibit the growth or proliferation of cells. In some embodiments, an anti-cancer agent is a chemotherapeutic. In some embodiments, an anti-cancer agent is an agent approved by the FDA or similar regulatory agency of a country other than the USA, for treating cancer.

Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechlorethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec.®.), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenyl acetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid;

spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or r1L.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol.™ (i.e. paclitaxel), Taxotere.™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-azaepothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta *Medica*), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta *Medica*), D-68144 (Asta *Medica*), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta *Medica*), D-68836 (Asta

*Medica*), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™) erlotinib (Tarceva™), cetuximab (Erbitux™), lapatinib (Tykerb™), panitumumab (Vectibix™) vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

"Patient" or "subject in need thereof" refers to a living organism suffering from or prone to a disease or condition that can be treated by administration of a compound or pharmaceutical composition or by a method, as provided herein. Non-limiting examples include humans, other mammals, bovines, rats, mice, dogs, monkeys, goat, sheep, cows, deer, and other non-mammalian animals. In some embodiments, a patient is human. In some embodiments, a subject is human.

"Disease" or "condition" refer to a state of being or health status of a patient or subject capable of being treated with a compound, pharmaceutical composition, or method provided herein. In some embodiments, the disease is a disease related to (e.g. caused by) an increase in the level (e.g. of activity or protein) of a component of a Myc family (e.g. c-Myc, N-Myc, L-Myc, or human Myc) protein pathway (e.g. Aurora A kinase, Myc family protein). In some embodiments, the disease is a disease related to (e.g. caused by) increase in the level (e.g. of activity or protein) of a Myc family (e.g. c-Myc, N-Myc, L-Myc, or human Myc) protein. In some embodiments, the disease is a disease related to (e.g. caused by) an increase in the level (e.g. of activity or protein) of Aurora A kinase. In some embodiments, the disease is a cancer associated with an increase in the level (e.g. level of activity or amount) of a Myc family (e.g. c-Myc, N-Myc, L-Myc, or human Myc) protein. In some embodiments, the disease is a cancer associated with an increase in the level (e.g. level of activity or amount) of a component of a Myc family (e.g. c-Myc, N-Myc, L-Myc, or human Myc) protein pathway (e.g. Aurora A kinase, Myc family protein). In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma; each associated with a modulated level of activity or amount of a component of a Myc family (e.g. c-Myc, N-Myc, L-Myc, or human Myc) protein pathway (e.g. Aurora A kinase, Myc family protein).

As used herein, the term "cancer" refers to all types of cancer, neoplasm or malignant tumors found in mammals (e.g. humans), including leukemia, carcinomas and sarcomas; each associated with a modulated level of activity or amount of a component of a Myc family (e.g. c-Myc, N-Myc, L-Myc, or human Myc) protein pathway (e.g. Aurora A kinase, Myc family protein). Exemplary cancers associated with a modulated level of activity or amount of a component of a Myc family (e.g. c-Myc, N-Myc, L-Myc, or human Myc) protein pathway (e.g. Aurora A kinase, Myc family protein) that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples associated with a modulated level of activity or amount of a component of a Myc family (e.g. c-Myc, N-Myc, L-Myc, or human Myc) protein pathway (e.g. Aurora A kinase, Myc family protein) may include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer, each associated with a modulated level of activity or amount of a component of a Myc family (e.g. c-Myc, N-Myc, L-Myc, or human Myc) protein pathway (e.g. Aurora A kinase, Myc family protein).

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be associated with a modulated level of activity or amount of a component of a Myc family (e.g. c-Myc, N-Myc, L-Myc, or human Myc) protein pathway (e.g. Aurora A kinase, Myc family protein) and may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be associated with a modulated level of activity or amount of a component of a Myc family (e.g. c-Myc, N-Myc, L-Myc, or human Myc) protein pathway (e.g. Aurora A kinase, Myc family protein) and may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be associated with a modulated level of activity or amount of a component of a Myc family (e.g. c-Myc, N-Myc, L-Myc, or human Myc) protein pathway (e.g. Aurora A kinase, Myc family protein) and may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be associated with a modulated level of activity or amount of a component of a Myc family (e.g. c-Myc, N-Myc, L-Myc, or human Myc) protein pathway (e.g. Aurora A kinase, Myc family protein) and may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tuberous carcinoma, verrucous carcinoma, or carcinoma *villosum*.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "co-administer" it is meant that a composition described herein is administered at the same time, just prior to, or just after the administration of one or more additional therapies (e.g. anti-cancer agent). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Pharmaceutical compositions provided by the present invention include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule (e.g. a component of a Myc family (e.g. c-Myc, N-Myc, L-Myc, or human Myc) protein pathway), and/or reducing, eliminating, or slowing the progression of disease symptoms (e.g. symptoms of cancer). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer such as radiation or surgery.

The term "MYCN" or "N-Myc" are used interchangeably and refer to the protein "V-Myc myelocytomatosis viral related oncogene, neuroblastoma derived". In embodiments, MYCN refers to the human protein MYCN. Included in the term MYCN are the wildtype and mutant forms of the protein. In embodiments, MYCN refers to the protein associated with Entrez Gene 4613, OMIM 164840, UniProt P04198, and/or RefSeq (protein) NP_005369. In embodiments, MYCN refers to the protein associated with one or more of the database entries listed immediately above at the time of filing of the present application.

The term "c-Myc" refers to the protein "V-Myc myelocytomatosis viral oncogene homolog". In embodiments, c-Myc refers to the human protein c-Myc. Included in the term c-Myc are the wildtype and mutant forms of the protein. In embodiments, c-Myc refers to the protein associated with Entrez Gene 4609, OMIM 190080, UniProt P01106, and/or RefSeq (protein) NP_002458. In embodiments, c-Myc refers to the protein associated with one or more of the database entries listed immediately above at the time of filing of the present application.

The term "L-Myc" refers to the protein "V-Myc myelocytomatosis viral oncogene homolog, lung carcinoma derived". In embodiments, L-Myc refers to the human protein L-Myc. Included in the term L-Myc are the wildtype and mutant forms of the protein. In embodiments, L-Myc refers to the protein associated with Entrez Gene 4610, OMIM 164850, UniProt P12524, and/or RefSeq (protein) NP_001028253. In embodiments, L-Myc refers to the protein associated with one or more of the database entries listed immediately above at the time of filing of the present application.

The term "Aurora A kinase" or "Aurora kinase A" or "AURKA" are used interchangeably and refer to the protein "Serine/threonine-protein kinase 6". In embodiments, Aurora A kinase refers to the human protein Aurora A kinase. Included in the term Aurora A kinase are the wildtype and mutant forms of the protein. In embodiments, Aurora A kinase refers to the protein associated with Entrez Gene 6790, OMIM 603072, UniProt O14965, and/or RefSeq (protein) NP_003591. In embodiments, Aurora A kinase refers to the protein associated with one or more of the database entries listed immediately above at the time of filing of the present application.

The term "Myc family protein" refers to any of the proteins c-Myc, N-Myc, or L-Myc, as described herein above. In embodiments, a Myc family protein is c-Myc. In embodiments, a Myc family protein is N-Myc. In embodiments, a Myc family protein is L-Myc. In embodiments, a Myc family protein is human c-Myc. In embodiments, a Myc family protein is human N-Myc. In embodiments, a Myc family protein is human L-Myc. In embodiments, a Myc family protein is a human Myc family protein.

The term "Myc family protein pathway" refers to a signal transduction pathway including a Myc family protein. In embodiments a Myc family protein pathway is a c-Myc protein pathway. In embodiments a Myc family protein pathway is an N-Myc protein pathway. In embodiments a Myc family protein pathway is an L-Myc protein pathway. A component of a Myc family protein pathway refers to a protein included in a signal transduction pathway including a Myc family protein. In embodiments, a component of a Myc family protein pathway is a protein included in a c-Myc family protein pathway. In embodiments, a component of a Myc family protein pathway is a protein included in an N-Myc family protein pathway. In embodiments, a component of a Myc family protein pathway is a protein included in an L-Myc family protein pathway. In embodiments, a component of a Myc family protein pathway is Aurora A kinase.

II. Compositions

In a first aspect is a compound, or pharmaceutically acceptable salt thereof, having the formula:

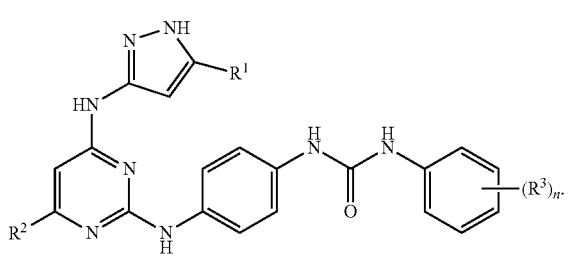

(I)

In formula (I), $R^1$ is a substituted or unsubstituted $C_5$ cycloalkyl, substituted or unsubstituted heterocycloalkyl, or substituted or unsubstituted 5 to 6 membered heteroaryl. R² is hydrogen, halogen, —CF₃, —CCl₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCH₃, —OCF₃, —OCHF₂, —C(O)CH₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R³ is independently halogen, —CF₃, —CCl₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCH₃, —OCF₃, —OCHF₂, —C(O)CH₃, unsubstituted alkyl, or unsubstituted heteroalkyl. The symbol n is independently an integer from 0 to 5.

In embodiments, a compound as described herein (including embodiments or as described in the examples, tables, figures, or claims) is provided. In embodiments, a pharmaceutically acceptable salt of a compound described herein (including embodiments or as described in the examples, tables, figures, or claims) is provided.

In embodiments, the compound has the formula:

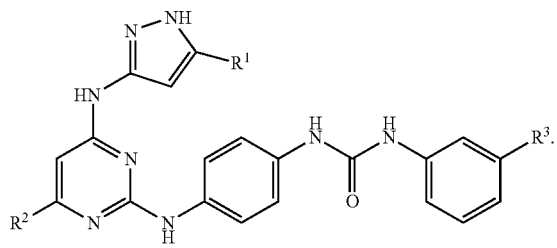

In embodiments, the compound has the formula:

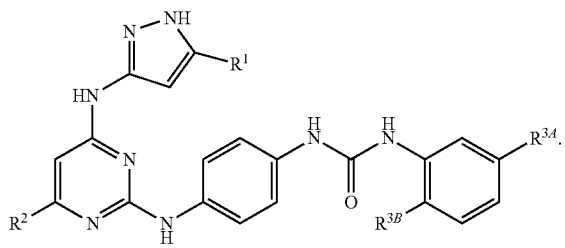

In embodiments, the compound has the formula:

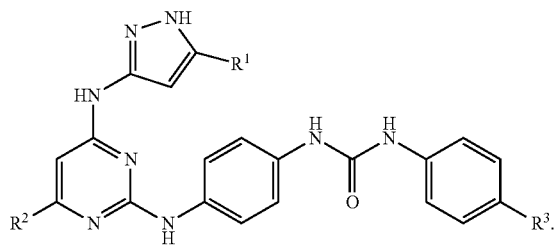

In embodiments, the compound has the formula:

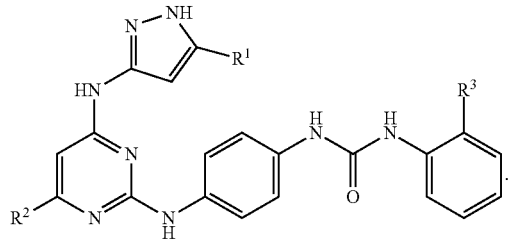

In embodiments, the compound has the formula:

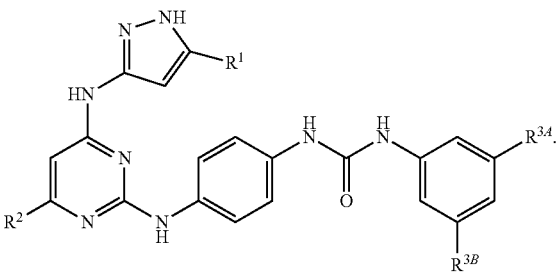

In embodiments, the compound has the formula:

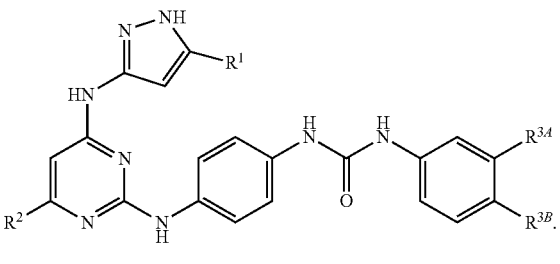

In embodiments, the compound has the formula:

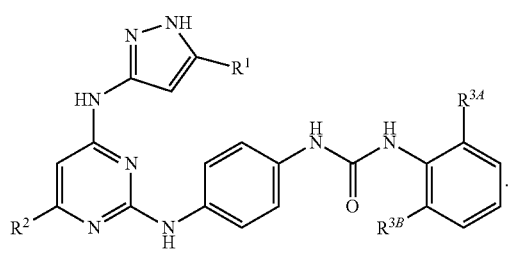

In embodiments, the compound has the formula:

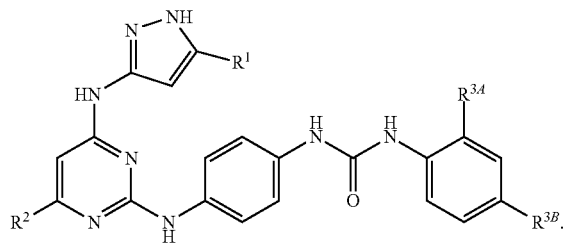

In embodiments, the compound is:

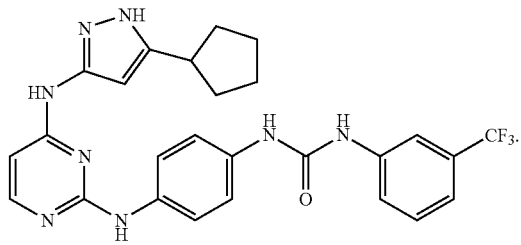 [SMILES: O=C(Nc1ccc(Nc2nccc(Nc3cc(C4CCCC4)[nH]n3)n2)cc1)Nc1cccc(C(F)(F)F)c1]

In embodiments, $R^1$ is a substituted or unsubstituted $C_5$ cycloalkyl, substituted or unsubstituted 5 to 6 membered heterocycloalkyl, or substituted or unsubstituted 5 to 6 membered heteroaryl. In embodiments, $R^1$ is an unsubstituted $C_5$ cycloalkyl, unsubstituted 5 to 6 membered heterocycloalkyl, or unsubstituted 5 to 6 membered heteroaryl. In embodiments, $R^1$ is an unsubstituted $C_5$ cycloalkyl. In embodiments, $R^1$ is an unsubstituted 5 to 6 membered heterocycloalkyl. In embodiments, $R^1$ is an unsubstituted 5 to 6 membered heteroaryl. In embodiments, $R^1$ is an unsubstituted cyclopentyl. In embodiments, $R^1$ is an unsubstituted furanyl.

In embodiments, $R^1$ is a substituted or unsubstituted $C_5$ cycloalkyl. In embodiments, $R^1$ is an unsubstituted $C_5$ cycloalkyl. In embodiments, $R^1$ is an unsubstituted cyclopentyl. In embodiments, $R^1$ is an unsubstituted cyclopentenyl. In embodiments, $R^1$ is a substituted $C_5$ cycloalkyl. In embodiments, $R^1$ is a substituted cyclopentyl. In embodiments, $R^1$ is a substituted cyclopentenyl. In embodiments, $R^1$ is a substituted $C_5$ cycloalkyl substituted with one substituent. In embodiments, $R^1$ is a substituted $C_5$ cycloalkyl substituted with two optionally different substituents. In embodiments, $R^1$ is a substituted $C_5$ cycloalkyl substituted with three optionally different substituents. In embodiments, $R^1$ is a substituted $C_5$ cycloalkyl substituted with four optionally different substituents.

In embodiments, $R^1$ is a $R^{11}$-substituted or unsubstituted $C_5$ cycloalkyl. In embodiments, $R^1$ is a $R^{11}$-substituted $C_5$ cycloalkyl. In embodiments, $R^1$ is a $R^{11}$-substituted cyclopentyl. In embodiments, $R^1$ is a $R^{11}$-substituted cyclopentenyl. In embodiments, $R^1$ is a $R^{11}$-substituted $C_5$ cycloalkyl substituted with one substituent. In embodiments, $R^1$ is a $R^{11}$-substituted $C_5$ cycloalkyl substituted with two optionally different substituents. In embodiments, le is a $R^{11}$-substituted $C_5$ cycloalkyl substituted with three optionally different substituents. In embodiments, $R^1$ is a $R^{11}$-substituted $C_5$ cycloalkyl substituted with four optionally different substituents.

In embodiments, $R^1$ is a substituted or unsubstituted heterocycloalkyl. In embodiments, $R^1$ is a substituted or unsubstituted 3 to 6 membered heterocycloalkyl. In embodiments, $R^1$ is a substituted or unsubstituted 4 to 6 membered heterocycloalkyl. In embodiments, $R^1$ is a substituted or unsubstituted 5 to 6 membered heterocycloalkyl. In embodiments, $R^1$ is a substituted or unsubstituted 5 membered heterocycloalkyl. In embodiments, $R^1$ is a substituted or unsubstituted heterocycloalkyl comprising one ring heteroatom (e.g. oxygen, sulfur, nitrogen). In embodiments, $R^1$ is a substituted or unsubstituted heterocycloalkyl comprising two optionally different ring heteroatoms (e.g. oxygen, sulfur, nitrogen). In embodiments, $R^1$ is a substituted or unsubstituted heterocycloalkyl comprising three optionally different ring heteroatoms (e.g. oxygen, sulfur, nitrogen). In embodiments, $R^1$ is an unsubstituted heterocycloalkyl. In embodiments, $R^1$ is an unsubstituted 3 to 6 membered heterocycloalkyl. In embodiments, $R^1$ is an unsubstituted 4 to 6 membered heterocycloalkyl. In embodiments, $R^1$ is an unsubstituted 5 to 6 membered heterocycloalkyl. In embodiments, $R^1$ is an unsubstituted 5 membered heterocycloalkyl. In embodiments, $R^1$ is an unsubstituted heterocycloalkyl comprising one ring heteroatom (e.g. oxygen, sulfur, nitrogen). In embodiments, $R^1$ is an unsubstituted heterocycloalkyl comprising two optionally different ring heteroatoms (e.g. oxygen, sulfur, nitrogen). In embodiments, $R^1$ is an unsubstituted heterocycloalkyl comprising three optionally different ring heteroatoms (e.g. oxygen, sulfur, nitrogen). In embodiments, $R^1$ is a substituted heterocycloalkyl. In embodiments, $R^1$ is a substituted 3 to 6 membered heterocycloalkyl. In embodiments, $R^1$ is a substituted 4 to 6 membered heterocycloalkyl. In embodiments, $R^1$ is a substituted 5 to 6 membered heterocycloalkyl. In embodiments, $R^1$ is a substituted 5 membered heterocycloalkyl. In embodiments, $R^1$ is a substituted heterocycloalkyl comprising one ring heteroatom (e.g. oxygen, sulfur, nitrogen). In embodiments, $R^1$ is a substituted heterocycloalkyl comprising two optionally different ring heteroatoms (e.g. oxygen, sulfur, nitrogen). In embodiments, $R^1$ is a substituted heterocycloalkyl comprising three optionally different ring heteroatoms (e.g. oxygen, sulfur, nitrogen). In embodiments, $R^1$ is a substituted heterocycloalkyl substituted with one substituent. In embodiments, $R^1$ is a substituted heterocycloalkyl substituted with two optionally different substituents. In embodiments, $R^1$ is a substituted heterocycloalkyl substituted with three optionally different substituents. In embodiments, $R^1$ is a substituted heterocycloalkyl substituted with four optionally different substituents.

In embodiments, $R^1$ is a $R^{11}$-substituted or unsubstituted heterocycloalkyl. In embodiments, $R^1$ is a $R^{11}$-substituted or unsubstituted 3 to 6 membered heterocycloalkyl. In embodiments, $R^1$ is a $R^{11}$-substituted or unsubstituted 4 to 6 membered heterocycloalkyl. In embodiments, $R^1$ is a $R^{11}$-substituted or unsubstituted 5 to 6 membered heterocycloalkyl. In embodiments, $R^1$ is a $R^{11}$-substituted or unsubstituted 5 membered heterocycloalkyl. In embodiments, $R^1$ is a $R^{11}$-substituted or unsubstituted heterocycloalkyl comprising one ring heteroatom (e.g. oxygen, sulfur, nitrogen). In embodiments, $R^1$ is a $R^{11}$-substituted or unsubstituted heterocycloalkyl comprising two optionally different ring heteroatoms (e.g. oxygen, sulfur, nitrogen). In embodiments, $R^1$ is a $R^{11}$-substituted or unsubstituted heterocycloalkyl comprising three optionally different ring heteroatoms (e.g. oxygen, sulfur, nitrogen). In embodiments, $R^1$ is a $R^{11}$-substituted heterocycloalkyl. In embodiments, $R^1$ is a $R^{11}$-substituted 3 to 6 membered heterocycloalkyl. In embodiments, $R^1$ is a $R^{11}$-substituted 4 to 6 membered heterocycloalkyl. In embodiments, $R^1$ is a $R^{11}$-substituted 5 to 6 membered heterocycloalkyl. In embodiments, $R^1$ is a $R^{11}$-substituted 5 membered heterocycloalkyl. In embodiments, $R^1$ is a $R^{11}$-substituted heterocycloalkyl comprising one ring heteroatom (e.g. oxygen, sulfur, nitrogen). In embodiments, $R^1$ is a $R^{11}$-substituted heterocycloalkyl comprising two optionally different ring heteroatoms (e.g. oxygen, sulfur, nitrogen). In embodiments, $R^1$ is a $R^{11}$-substituted heterocycloalkyl comprising three optionally different ring heteroatoms (e.g. oxygen, sulfur, nitrogen). In embodiments, $R^1$ is a $R^{11}$-substituted heterocycloalkyl substituted with one substituent. In embodiments, $R^1$ is a $R^{11}$-substituted heterocycloalkyl substituted with two optionally different substituents. In embodiments, $R^1$ is a $R^{11}$-substituted heterocycloalkyl substituted with three optionally different substituents. In embodiments, $R^1$ is a $R^{11}$-substituted heterocycloalkyl substituted with four optionally different substituents.

In embodiments, $R^1$ is a substituted or unsubstituted 5 to 6 membered heteroaryl. In embodiments, $R^1$ is a substituted or unsubstituted 5 membered heteroaryl. In embodiments, $R^1$ is a substituted or unsubstituted 6 membered heteroaryl. In embodiments, $R^1$ is an unsubstituted 5 to 6 membered heteroaryl. In embodiments, $R^1$ is an unsubstituted 5 membered heteroaryl. In embodiments, $R^1$ is an unsubstituted 6 membered heteroaryl. In embodiments, $R^1$ is a substituted 5 to 6 membered heteroaryl. In embodiments, $R^1$ is a substituted 5 membered heteroaryl. In embodiments, $R^1$ is a substituted 6 membered heteroaryl. In embodiments, $R^1$ is a substituted heteroaryl comprising one ring heteroatom (e.g. oxygen, sulfur, nitrogen). In embodiments, $R^1$ is a substituted heteroaryl comprising two optionally different ring heteroatoms (e.g. oxygen, sulfur, nitrogen). In embodiments, $R^1$ is a substituted heteroaryl comprising three optionally different ring heteroatoms (e.g. oxygen, sulfur, nitrogen). In embodiments, $R^1$ is a substituted heteroaryl substituted with one substituent. In embodiments, $R^1$ is a substituted heteroaryl substituted with two optionally different substituents. In embodiments, $R^1$ is a substituted heteroaryl substituted with three optionally different substituents. In embodiments, $R^1$ is a substituted heteroaryl substituted with four optionally different substituents. In embodiments, $R^1$ is a substituted or unsubstituted furanyl. In embodiments, $R^1$ is an unsubstituted furanyl. In embodiments, $R^1$ is a substituted furanyl.

In embodiments, $R^1$ is a $R^{11}$-substituted or unsubstituted 5 to 6 membered heteroaryl. In embodiments, $R^1$ is a $R^{11}$-substituted or unsubstituted 5 membered heteroaryl. In embodiments, $R^1$ is a $R^{11}$-substituted or unsubstituted 6 membered heteroaryl. In embodiments, $R^1$ is a $R^{11}$-substituted 5 to 6 membered heteroaryl. In embodiments, $R^1$ is a $R^{11}$-substituted 5 membered heteroaryl. In embodiments, $R^1$ is a $R^{11}$-substituted 6 membered heteroaryl. In embodiments, $R^1$ is a $R^{11}$-substituted heteroaryl comprising one ring heteroatom (e.g. oxygen, sulfur, nitrogen). In embodiments, $R^1$ is a $R^{11}$-substituted heteroaryl comprising two optionally different ring heteroatoms (e.g. oxygen, sulfur, nitrogen). In embodiments, $R^1$ is a $R^{11}$-substituted heteroaryl comprising three optionally different ring heteroatoms (e.g. oxygen, sulfur, nitrogen). In embodiments, $R^1$ is a $R^{11}$-substituted heteroaryl substituted with one substituent. In embodiments, $R^1$ is a $R^{11}$-substituted heteroaryl substituted with two optionally different substituents. In embodiments, $R^1$ is a $R^{11}$-substituted heteroaryl substituted with three optionally different substituents. In embodiments, $R^1$ is a $R^{11}$-substituted heteroaryl substituted with four optionally different substituents. In embodiments, $R^1$ is a $R^{11}$-substituted or unsubstituted furanyl. In embodiments, $R^1$ is a $R^{11}$-substituted furanyl.

In embodiments, $R^1$ is $R^{11}$-substituted or unsubstituted $C_5$ cycloalkyl, $R^{11}$-substituted or unsubstituted heterocycloalkyl, or $R^{11}$-substituted or unsubstituted 5 to 6 membered heteroaryl. $R^1$ may be $R^{11}$-substituted or unsubstituted $C_5$ cycloalkyl or $R^{11}$-substituted or unsubstituted heterocycloalkyl. $R^1$ may be $R^{11}$-substituted or unsubstituted $C_5$ cycloalkyl or $R^{11}$-substituted or unsubstituted 5 to 6 membered heteroaryl. $R^1$ may be $R^{11}$-substituted or unsubstituted heterocycloalkyl or $R^{11}$-substituted or unsubstituted 5 to 6 membered heteroaryl.

$R^{11}$ is oxo, halogen, —$CF_3$, —$CCl_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCH_3$, —$OCF_3$, —$OCHF_2$, —$C(O)CH_3$, $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl, or $R^{12}$-substituted or unsubstituted heteroaryl.

$R^{12}$ is independently oxo, halogen, —$CF_3$, —$CCl_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCH_3$, —$OCF_3$, —$OCHF_2$, —$C(O)CH_3$, $R^{13}$-substituted or unsubstituted alkyl, $R^{13}$-substituted or unsubstituted heteroalkyl, $R^{13}$-substituted or unsubstituted cycloalkyl, $R^{13}$-substituted or unsubstituted heterocycloalkyl, $R^{13}$-substituted or unsubstituted aryl, or $R^{13}$-substituted or unsubstituted heteroaryl.

$R^{13}$ is independently hydrogen, oxo, halogen, —$CF_3$, —$CCl_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCH_3$, —$OCF_3$, —$OCHF_2$, —$C(O)CH_3$, unsubstituted alkyl (e.g. $C_1$-$C_{10}$ alkyl), unsubstituted heteroalkyl (e.g. 2 to 8 membered heteroalkyl), unsubstituted cycloalkyl (e.g. $C_3$-$C_8$ cycloalkyl), unsubstituted heterocycloalkyl (e.g. $C_3$-$C_8$ heterocycloalkyl), unsubstituted aryl (e.g. $C_5$-$C_{10}$ aryl), or unsubstituted heteroaryl (e.g. $C_5$-$C_{10}$ heteroaryl).

In embodiments, $R^2$ is hydrogen, halogen, —$CF_3$, —$CCl_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCH_3$, —$OCF_3$, —$OCHF_2$, —$C(O)CH_3$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^2$ is hydrogen, halogen, —$CF_3$, —$CCl_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCH_3$, —$OCF_3$, —$OCHF_2$, —$C(O)CH_3$, substituted or unsubstituted $C_1$-$C_4$ alkyl, substituted or unsubstituted 2 to 4 membered heteroalkyl, substituted or unsubstituted $C_3$-$C_5$ cycloalkyl, substituted or unsubstituted 3 to 5 membered heterocycloalkyl, substituted or unsubstituted $C_6$-$C_{10}$ aryl, or substituted or unsubstituted 5 to 9 membered heteroaryl. In embodiments, $R^2$ is hydrogen, halogen, —$CF_3$, —$CCl_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —ONH$_2$, —NHC(O)NHNH$_2$, —NHC(O)NH$_2$, —NHSO$_2$H, —NHC(O)H, —NHC(O)OH, —NHOH, —OCH$_3$, —OCF$_3$, —OCHF$_2$, or —C(O)CH$_3$. In embodiments, R$^2$ is hydrogen, substituted or unsubstituted C$_1$-C$_4$ alkyl, substituted or unsubstituted 2 to 4 membered heteroalkyl, substituted or unsubstituted C$_3$-C$_5$ cycloalkyl, substituted or unsubstituted 3 to 5 membered heterocycloalkyl, substituted or unsubstituted C$_6$-C$_{10}$ aryl, or substituted or unsubstituted 5 to 9 membered heteroaryl. In embodiments, R$^2$ is hydrogen, unsubstituted C$_1$-C$_4$ alkyl, unsubstituted 2 to 4 membered heteroalkyl, unsubstituted C$_3$-C$_5$ cycloalkyl, unsubstituted 3 to 5 membered heterocycloalkyl, unsubstituted C$_6$-C$_{10}$ aryl, or unsubstituted 5 to 9 membered heteroaryl. In embodiments, R$^2$ is hydrogen or unsubstituted C$_1$-C$_4$ alkyl. In embodiments, R$^2$ is hydrogen or unsubstituted methyl. In embodiments, R$^2$ is hydrogen.

In embodiments, R$^2$ is hydrogen, halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCH$_3$, —OCF$_3$, —OCHF$_2$, —C(O)CH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R$^2$ is hydrogen. In embodiments, R$^2$ is halogen. In embodiments, R$^2$ is —F. In embodiments, R$^2$ is —Cl. In embodiments, R$^2$ is —Br. In embodiments, R$^2$ is —I. In embodiments, R$^2$ is —CF$_3$. In embodiments, R$^2$ is —CCl$_3$. In embodiments, R$^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R$^2$ is substituted or unsubstituted alkyl. In embodiments, R$^2$ is substituted or unsubstituted heteroalkyl. In embodiments, R$^2$ is substituted or unsubstituted cycloalkyl. In embodiments, R$^2$ is substituted or unsubstituted heterocycloalkyl. In embodiments, R$^2$ is substituted or unsubstituted aryl. In embodiments, R$^2$ is substituted or unsubstituted heteroaryl.

In embodiments, R$^2$ is substituted or unsubstituted C$_1$-C$_6$ alkyl. In embodiments, R$^2$ is substituted or unsubstituted 2 to 6 membered heteroalkyl. In embodiments, R$^2$ is substituted or unsubstituted C$_3$-C$_6$ cycloalkyl. In embodiments, R$^2$ is substituted or unsubstituted 3 to 6 membered heterocycloalkyl. In embodiments, R$^2$ is substituted or unsubstituted C$_6$-C$_{10}$ aryl. In embodiments, R$^2$ is substituted or unsubstituted 5 to 9 membered heteroaryl. In embodiments, R$^2$ is substituted or unsubstituted C$_1$-C$_4$ alkyl. In embodiments, R$^2$ is substituted or unsubstituted 2 to 4 membered heteroalkyl. In embodiments, R$^2$ is substituted or unsubstituted C$_3$-C$_5$ cycloalkyl. In embodiments, R$^2$ is substituted or unsubstituted 3 to 5 membered heterocycloalkyl. In embodiments, R$^2$ is substituted or unsubstituted C$_6$ aryl. In embodiments, R$^2$ is substituted or unsubstituted 5 to 6 membered heteroaryl. In embodiments, R$^2$ is substituted or unsubstituted methyl. In embodiments, R$^2$ is unsubstituted methyl. In embodiments, R$^2$ is substituted or unsubstituted piperazinyl. In embodiments, R$^2$ is 4-methyl-1-piperazinyl. In embodiments, R$^2$ is substituted C$_1$-C$_4$ alkyl. In embodiments, R$^2$ is unsubstituted C$_1$-C$_4$ alkyl. In embodiments, R$^2$ is substituted 2 to 4 membered heteroalkyl. In embodiments, R$^2$ is unsubstituted 2 to 4 membered heteroalkyl. In embodiments, R$^2$ is substituted C$_3$-C$_5$ cycloalkyl.

In embodiments, R$^2$ is unsubstituted C$_3$-C$_5$ cycloalkyl. In embodiments, R$^2$ is substituted 3 to 5 membered heterocycloalkyl. In embodiments, R$^2$ is unsubstituted 3 to 5 membered heterocycloalkyl. In embodiments, R$^2$ is substituted C$_6$-C$_{10}$ aryl. In embodiments, R$^2$ is unsubstituted C$_6$-C$_{10}$ aryl. In embodiments, R$^2$ is substituted 5 to 9 membered heteroaryl. In embodiments, R$^2$ is unsubstituted 5 to 9 membered heteroaryl.

In embodiments, R$^2$ is independently hydrogen, halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCH$_3$, —OCF$_3$, —OCHF$_2$, —C(O)CH$_3$, R$^{14}$-substituted or unsubstituted alkyl, R$^{14}$-substituted or unsubstituted heteroalkyl, R$^{14}$-substituted or unsubstituted cycloalkyl, R$^{14}$-substituted or unsubstituted heterocycloalkyl, R$^{14}$-substituted or unsubstituted aryl, or R$^{14}$-substituted or unsubstituted heteroaryl.

R$^{14}$ is independently oxo, halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCH$_3$, —OCHF$_2$, —C(O)CH$_3$, R$^{15}$-substituted or unsubstituted alkyl, R$^{15}$-substituted or unsubstituted heteroalkyl, R$^{15}$-substituted or unsubstituted cycloalkyl, R$^{15}$-substituted or unsubstituted heterocycloalkyl, R$^{15}$-substituted or unsubstituted aryl, or R$^{15}$-substituted or unsubstituted heteroaryl.

R$^{15}$ is independently oxo, halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCH$_3$, —OCHF$_2$, —C(O)CH$_3$, R$^{16}$-substituted or unsubstituted alkyl, R$^{16}$-substituted or unsubstituted heteroalkyl, R$^{16}$-substituted or unsubstituted cycloalkyl, R$^{16}$-substituted or unsubstituted heterocycloalkyl, R$^{16}$-substituted or unsubstituted aryl, or R$^{16}$-substituted or unsubstituted heteroaryl.

R$^{16}$ is independently hydrogen, oxo, halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCH$_3$, —OCHF$_2$, —C(O)CH$_3$, unsubstituted alkyl (e.g. C$_1$-C$_{10}$ alkyl), unsubstituted heteroalkyl (e.g. 2 to 8 membered heteroalkyl), unsubstituted cycloalkyl (e.g. C$_3$-C$_8$ cycloalkyl), unsubstituted heterocycloalkyl (e.g. C$_3$-C$_8$ heterocycloalkyl), unsubstituted aryl (e.g. C$_5$-C$_{10}$ aryl), or unsubstituted heteroaryl (e.g. C$_5$-C$_{10}$ heteroaryl).

In embodiments, R$^3$ is independently halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCH$_3$, —OCHF$_2$, —C(O)CH$_3$, unsubstituted C$_1$-C$_4$ alkyl, or unsubstituted 2 to 4 membered heteroalkyl. In embodiments, R$^3$ is independently halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHOH, —OCH$_3$, —OCF$_3$, —OCHF$_2$, —C(O)CH$_3$, or unsubstituted methyl. In embodiments, R$^3$ is independently —CF$_3$.

In embodiments, R$^3$ is independently halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCH$_3$, —OCF$_3$, —OCHF$_2$, —C(O)CH$_3$, unsubstituted alkyl, or unsubstituted heteroalkyl. In embodiments, R³ is halogen. In embodiments, R³ is independently —F. In embodiments, R³ is independently —Cl. In embodiments, R³ is independently —Br. In embodiments, R³ is independently —I. In embodiments, R³ is independently —CF₃. In embodiments, R³ is independently —CCl₃. In embodiments, R³ is independently unsubstituted alkyl or unsubstituted heteroalkyl. In embodiments, R³ is independently unsubstituted alkyl. In embodiments, R³ is independently unsubstituted heteroalkyl. In embodiments, R³ is independently unsubstituted C₁-C₆ alkyl. In embodiments, R³ is independently unsubstituted C₁-C₅ alkyl. In embodiments, R³ is independently unsubstituted C₁-C₄ alkyl. In embodiments, R³ is independently unsubstituted C₁-C₃ alkyl. In embodiments, R³ is independently unsubstituted C₁-C₂ alkyl. In embodiments, R³ is independently unsubstituted methyl. In embodiments, R³ is independently unsubstituted 2 to 6 membered heteroalkyl. In embodiments, R³ is independently unsubstituted 2 to 5 membered heteroalkyl. In embodiments, R³ is independently unsubstituted 2 to 4 membered heteroalkyl. In embodiments, R³ is independently unsubstituted 2 to 3 membered heteroalkyl. In embodiments, R³ is independently unsubstituted 2 membered heteroalkyl.

In embodiments, the symbol n is independently 0. In embodiments, the symbol n is independently 1. In embodiments, the symbol n is independently 2. In embodiments, the symbol n is independently 3. In embodiments, the symbol n is independently 4. In embodiments, the symbol n is independently 5.

In embodiments, the compound is in a pharmaceutical composition including a pharmaceutically acceptable excipient. In embodiments, the compound is in a pharmaceutically acceptable salt. In embodiments, the compound is co-administered with a second agent (e.g. therapeutic agent). In embodiments, the second agent is administered in a therapeutically effective amount. In embodiments, the compound and a second agent (e.g. therapeutic agent) are in a pharmaceutical composition including a pharmaceutically acceptable excipient. In embodiments, the second agent is a PI3K inhibitor. In embodiments, the second agent is an mTOR inhibitor. In embodiments, the second agent is a BRD4-based bromodomain inhibitor. In embodiments, the compound is co-administered with one or more additional agents selected from the group consisting of an anti-cancer agent as known in the art, a PI3K inhibitor, an mTOR inhibitor, and a BRD4-based bromodomain inhibitor.

In embodiments, the compound is a compound described in the Examples, an example, a table, the figures, a figure, included herein. In embodiments, the compound is a compound described in the method sections herein below.

In embodiments, the compound is 1-(4-((4-((5-cyclopentyl-1H-pyrazol-3-yl)amino)pyrimidin-2-yl)amino)phenyl)-3-(3-(trifluoromethyl)phenyl)urea (CD532). In embodiments, the compound is 3-[4-({4-[(5-cyclopentyl-1H-pyrazol-3-yl)amino]pyrimidin-2-yl}amino)phenyl]-1-phenylurea (JM25, p183, CD25). In embodiments, the compound is 3-[4-({4-[(5-cyclopentyl-1H-pyrazol-3-yl)amino]pyrimidin-2-yl}amino)phenyl]-1-[2-fluoro-5-(trifluoromethyl)phenyl]urea (JM192, CD192). In embodiments, the compound is 1-(4-((4-((5-cyclopentyl-1H-pyrazol-3-yl)amino)-6-methylpyrimidin-2-yl)amino)phenyl)-3-(3-(trifluoromethyl)phenyl)urea (CD15). In embodiments, the compound is 3-[4-({4-[(5-cyclohexyl-1H-pyrazol-3-yl)amino]-6-methylpyrimidin-2-yl}amino)phenyl]-1-[3-(trifluoromethyl)phenyl]urea (CD22). In embodiments, the compound is 3-[4-({4-[(5-cyclohexyl-1H-pyrazol-3-yl)amino]-6-methylpyrimidin-2-yl}amino) phenyl]-1-phenylurea (CD24). In embodiments, the compound is 1-(4-((4-((5-(furan-2-yl)-1H-pyrazol-3-yl)amino)pyrimidin-2-yl)amino)phenyl)-3-(3-(trifluoromethyl)phenyl)urea (JM134).

III. Pharmaceutical Compositions

Also provided herein are pharmaceutical compositions. In one aspect, the pharmaceutical composition includes a pharmaceutically acceptable excipient and a compound, or pharmaceutically acceptable salt thereof, as described herein, including embodiments (e.g. compound of formula (I), or any embodiment thereof), including compounds described for use in a method herein or in the Compounds section above or in an example, table, figure, or claim.

In embodiments of the pharmaceutical compositions, the pharmaceutical composition includes a compound, or pharmaceutically acceptable salt thereof, as described herein (e.g. compound of formula (I), or any embodiment thereof) in a therapeutically effective amount. In embodiments of the pharmaceutical compositions, the pharmaceutical composition includes a second agent (e.g. therapeutic agent). In embodiments of the pharmaceutical compositions, the pharmaceutical composition includes a second agent in a therapeutically effective amount. In embodiments of the pharmaceutical compositions, the second agent is an agent for treating cancer.

Thus, in embodiments, the compound has the formula:

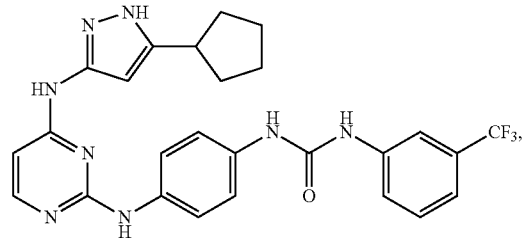

(CD532)

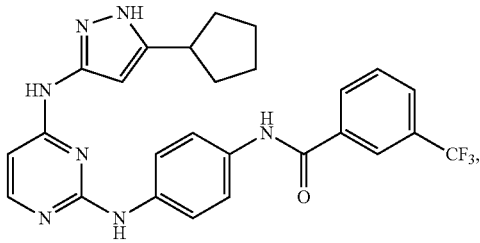

(CD12)

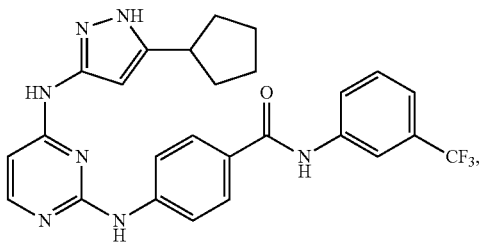

(CD13)

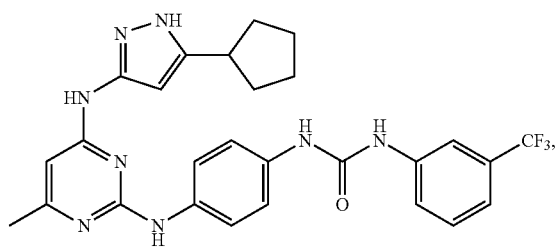
(CD15)
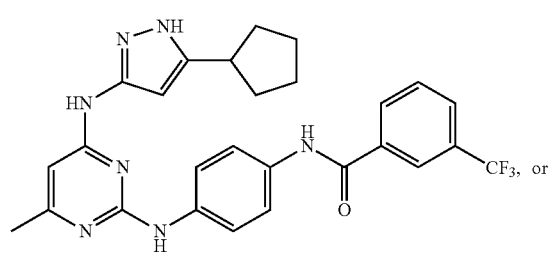
(CD16)
(CD17)
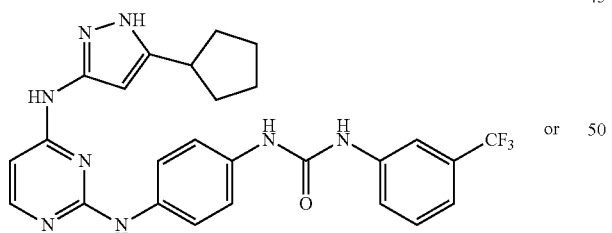
The compound may have the formula:
(CD532)
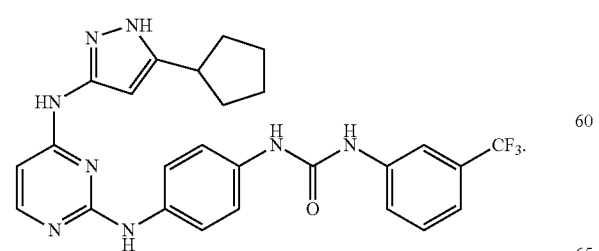
or
(CD15)
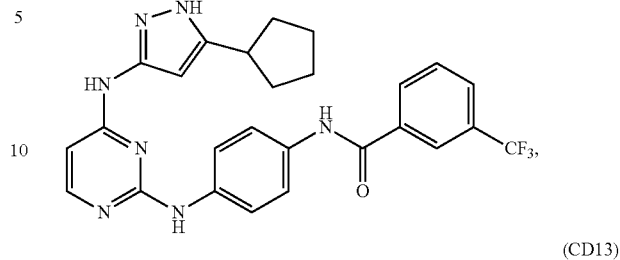
(CD12)
(CD13)
(CD16)
(CD17)
The compound may have the formula:
(CD532)
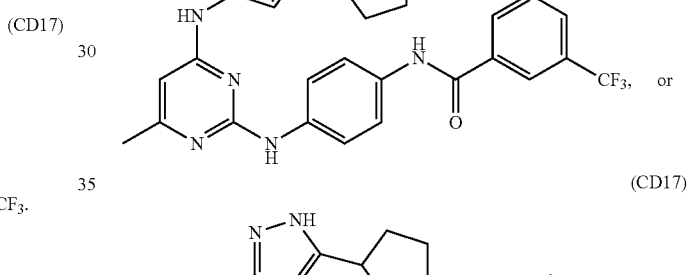
IV. Methods of Modulating Enzymatic Activity
Provided herein are methods of modulating the level of activity of Aurora A kinase. In one aspect, the method includes contacting the Aurora A kinase with an effective amount of a compound, or a pharmaceutically acceptable salt thereof, as described herein, including embodiments or in any examples, tables, or figures (e.g. compound of formula (I)). The effective amount may be a therapeutically effective amount.

In embodiments, the method of modulating is a method of inhibiting. In embodiments, the method of modulating is a method of increasing. In embodiments, the Aurora A kinase is in vitro. In embodiments, the Aurora A kinase is in a subject. In embodiments, the activity is Aurora A kinase enzymatic activity. In embodiments, the activity is Aurora A kinase protein binding activity. In embodiments, the Aurora A kinase protein binding activity is Aurora A kinase-Myc family (e.g. c-Myc, N-Myc, L-Myc, or human Myc) protein binding activity (i.e. Aurora A kinase binding to a Myc family protein). In embodiments, a Myc family protein is c-Myc. In embodiments, a Myc family protein is N-Myc. In embodiments, a Myc family protein is MYCN. In embodiments, a Myc family protein is L-Myc. In embodiments, a Myc family protein is a human Myc family protein. In embodiments, the Aurora A kinase-Myc family protein binding activity is Aurora A kinase-MYCN protein binding activity. In embodiments, the Aurora A kinase-Myc family protein binding activity is Aurora A kinase-N-Myc protein binding activity. In embodiments, the Aurora A kinase-Myc family protein binding activity is Aurora A kinase-c-Myc protein binding activity. In embodiments, the Aurora A kinase-Myc family protein binding activity is Aurora A kinase-L-Myc protein binding activity. In embodiments, the activity is Aurora A kinase stabilization of a Myc family (e.g. c-Myc, N-Myc, L-Myc, or human Myc) protein. In embodiments, the activity is Aurora A kinase protection of a Myc family (e.g. c-Myc, N-Myc, L-Myc, or human Myc) protein from protein degradation. In embodiments, the activity is stabilization of a conformation of a Myc family (e.g. c-Myc, N-Myc, L-Myc, or human Myc) protein. In embodiments, the activity is stabilization of a conformation of the Aurora A kinase protein. In embodiments, the activity is Aurora A kinase phosphorylation of p53. In embodiments, the activity is Aurora A kinase phosphorylation of BRCA1. In embodiments, the activity is Aurora A kinase phosphorylation of Histone H3. In embodiments, the activity is phosphorylation of p53. In embodiments, the activity is phosphorylation of BRCA1. In embodiments, the activity is phosphorylation of Histone H3.

In embodiments, the compound is in a pharmaceutical composition including a pharmaceutically acceptable excipient. In embodiments, the compound is in a pharmaceutically acceptable salt. In embodiments of the method, the compound is co-administered with a second agent (e.g. therapeutic agent). In embodiments of the method, the second agent is administered in a therapeutically effective amount.

Also provided herein are methods of modulating the level of activity of a Myc family (e.g. c-Myc, N-Myc, or L-Myc, or human Myc) protein in a cell. In one aspect, the method includes contacting the cell with an effective amount of a compound, or a pharmaceutically acceptable salt thereof, as described herein, including embodiments or in any examples, tables, or figures (e.g. compound of formula (I)). The effective amount may be a therapeutically effective amount.

In embodiments, the method of modulating is a method of inhibiting. Thus, in embodiments, the method of modulating is a method of modulating degradation of a Myc family protein (e.g. c-Myc, N-Myc, L-Myc, or human Myc). In embodiments, the method of modulating (e.g. inhibiting) the level of activity of a Myc family protein is a method of modulating (e.g. increasing) the rate of degradation of the Myc family protein. In embodiments, the method of modulating (e.g. inhibiting) the level of activity of a Myc family (e.g. c-Myc, N-Myc, or L-Myc, or human Myc) protein is a method of modulating (e.g. inhibiting) the protein-protein interaction (e.g. with Aurora A kinase) of the Myc family (e.g. c-Myc, N-Myc, or L-Myc, or human Myc) protein. The method of modulating may include modulating degradation of c-Myc. The method of modulating may include modulating degradation of N-Myc. The method of modulating may include modulating degradation of L-Myc. The method of modulating may include modulating degradation of human Myc.

In embodiments, the level of activity of a Myc family (e.g. c-Myc, N-Myc, L-Myc, or human Myc) protein is an amount of the Myc family (e.g. c-Myc, N-Myc, or L-Myc, or human Myc) protein. In embodiments, the level of activity of a Myc family (e.g. c-Myc, N-Myc, L-Myc, or human Myc) protein is an amount of the Myc family (e.g. c-Myc, N-Myc, L-Myc, or human Myc) protein in the cell. The terms "amount of a protein in a cell" and "protein level" are used interchangeably and have the same meaning. In embodiments, a Myc family protein is c-Myc. In embodiments, a Myc family protein is N-Myc. In embodiments, a Myc family protein is MYCN. In embodiments, a Myc family protein is L-Myc. In embodiments, a Myc family protein is a human Myc family protein.

In embodiments, the compound is in a pharmaceutical composition including a pharmaceutically acceptable excipient. In embodiments, the compound is in a pharmaceutically acceptable salt. In embodiments of the method, the compound is co-administered with a second agent (e.g. therapeutic agent). In embodiments of the method, the second agent is administered in a therapeutically effective amount.

V. Methods of Treatment

Provided herein are methods of treating a Myc family (e.g. c-Myc, N-Myc, L-Myc, or human Myc) protein pathway associated cancer in a patient in need of such treatment. In one aspect, the method includes administering to a subject in need thereof, a therapeutically effective amount of a compound, or a pharmaceutically acceptable salt thereof, as described herein, including embodiments or in any examples, tables, or figures (e.g. compound of formula (I)).

In embodiments, the cancer is an Aurora A kinase associated cancer. In embodiments, the cancer is associated with an increase in the level of activity of Aurora A kinase in a cell (e.g. kinase activity or binding activity). In embodiments, the cancer is associated with an increase in the amount of Aurora A kinase. In embodiments, the cancer is associated with an increase in the amount of Aurora A kinase protein. In embodiments, the cancer is associated with an increase in the amount of Aurora A kinase in a cell. In embodiments, the cancer is associated with an increase in the amount of Aurora A kinase protein in a cell. In embodiments, the cancer is associated with an increase in the level of activity of Aurora A kinase. The increase in the level of activity of Aurora A kinase is as described herein, including embodiments thereof.

Thus, in another aspect is a method of treating an Aurora A kinase associated cancer in a patient in need of such treatment by administering to a subject in need thereof, a therapeutically effective amount of a compound, or a pharmaceutically acceptable salt thereof, as described herein, including embodiments thereof (e.g. compound of formula (I)). In embodiments, the compound is CD532.

In embodiments, the cancer is a Myc family protein (e.g. c-Myc, N-Myc, L-Myc, or human Myc) associated cancer. In embodiments, the cancer is an N-Myc associated cancer. In embodiments, the cancer is a c-Myc associated cancer. In embodiments, the cancer is an L-Myc associated cancer.

In embodiments, the cancer is associated with an increase in the level of activity of N-Myc. In embodiments, the cancer is associated with an increase in the level of activity of c-Myc. In embodiments, the cancer is associated with an increase in the level of activity of L-Myc.

In embodiments, the cancer is associated with an increase in the level of activity of N-Myc in a cell. In embodiments, the cancer is associated with an increase in the level of activity of c-Myc in a cell. In embodiments, the cancer is associated with an increase in the level of activity of L-Myc in a cell.

In embodiments, the cancer is associated with an increase in the amount of N-Myc. In embodiments, the cancer is associated with an increase in the amount of c-Myc. In embodiments, the cancer is associated with an increase in the amount of L-Myc. In embodiments, the cancer is associated with an increase in the amount of N-Myc protein. In embodiments, the cancer is associated with an increase in the amount of c-Myc protein. In embodiments, the cancer is associated with an increase in the amount of L-Myc protein.

In embodiments, the cancer is associated with an increase in the amount of N-Myc in a cell. In embodiments, the cancer is associated with an increase in the amount of c-Myc in a cell. In embodiments, the cancer is associated with an increase in the amount of L-Myc in a cell. In embodiments, the cancer is associated with an increase in the amount of N-Myc protein in a cell. In embodiments, the cancer is associated with an increase in the amount of c-Myc protein in a cell. In embodiments, the cancer is associated with an increase in the amount of L-Myc protein in a cell.

In embodiments, the cancer is associated with an increased amount of a Myc family (e.g. c-Myc, N-Myc, L-Myc, or human Myc) protein relative to the same type of cell that expresses a non-disease or natural amount of a Myc family (e.g. c-Myc, N-Myc, L-Myc, or human Myc) protein.

In embodiments, the cancer is associated with an increased amount of a protein in a Myc family protein pathway. In embodiments, the cancer is associated with a decreased amount of a protein in a Myc family protein pathway. In embodiments, the cancer is associated with an increased level (e.g. of activity or amount) of a protein in a Myc family (e.g. c-Myc, N-Myc, L-Myc, or human Myc) protein pathway. In embodiments, the cancer is associated with a decreased level (e.g. of activity or amount) of a protein in a Myc family (e.g. c-Myc, N-Myc, L-Myc, or human Myc) protein pathway. In embodiments, the cancer is associated with an increased level of activity of a protein in a Myc family (e.g. c-Myc, N-Myc, L-Myc, or human Myc) protein pathway. In embodiments, the cancer is associated with a decreased level of activity of a protein in a Myc family (e.g. c-Myc, N-Myc, L-Myc, or human Myc) protein pathway.

In embodiments, the cancer is associated with an increased level of a protein, the expression of which is increased by a Myc family (e.g. c-Myc, N-Myc, L-Myc, or human Myc) protein relative to the expression level of the protein in the absence of the Myc family protein (e.g. proteins with expression increased by a Myc family protein). The cancer may be associated with the binding activity of Aurora A Kinase and a Myc family protein (e.g. (e.g. c-Myc, N-Myc, L-Myc, or human Myc). Thus, in embodiments, the cancer is associated with the binding activity of Aurora A Kinase and N-Myc.

Provided herein are methods of treating a cancer in a patient in need of such treatment. In one aspect, the method includes administering to a subject in need thereof, a therapeutically effective amount of a compound, or a pharmaceutically acceptable salt thereof, as described herein, including embodiments or in any examples, tables, or figures (e.g. compound of formula (I)).

In embodiments, the cancer (e.g. Aurora A kinase associated cancer or Myc family protein associated cancer) is thyroid cancer, endocrine system cancer, brain cancer, breast cancer, cervical cancer, colon cancer, head & neck cancer, liver cancer, kidney cancer, lung cancer, non-small cell lung cancer, melanoma, mesothelioma, ovarian cancer, sarcoma, stomach cancer, uterine cancer, neuroblastoma, Medulloblastoma, colorectal cancer, prostate cancer or pancreatic cancer.

The cancer (e.g. Aurora A kinase associated cancer or Myc family protein associated cancer) may be neuroblastoma. The cancer may be Medulloblastoma. The cancer may be breast cancer. The cancer may be cervical cancer. In embodiments, the cancer is colon cancer. The cancer may be lung cancer. The cancer may be stomach cancer. The cancer may be pancreatic cancer. The cancer may be prostate cancer.

In embodiments, the increased characteristic described above (e.g. level of activity, amount, amount of protein, level of activity in a cell, amount in a cell, or amount of protein in a cell) is increased relative to a control (e.g. non-disease cell(s), non-cancer cell(s), average level or amount determined for non-disease or non-cancer cell or sample, non-disease sample, non-cancer sample).

In embodiments, the compound of the methods described herein is in a pharmaceutical composition including a pharmaceutically acceptable excipient. The compound may be CD532. In embodiments, the compound of the methods described herein is in a pharmaceutically acceptable salt. In embodiments of the method, the compound is co-administered with a second agent (e.g. therapeutic agent). In embodiments of the method, the second agent is administered in a therapeutically effective amount. In embodiments, the second agent is an anti-cancer agent. Suitable anti-cancer agents for co-administration in a method described herein may be determined by one of ordinary skill in the art.

In embodiments, the administration of the therapeutically effective amount of a compound, or a pharmaceutically acceptable salt thereof decreases (i.e. inhibits) the activity of Aurora A Kinase or a Myc family protein (e.g. c-Myc, N-Myc, L-Myc, or human Myc). The therapeutically effective amount of a compound or a pharmaceutically acceptable salt thereof may decrease (i.e. inhibit) the activity (e.g. kinase activity or binding activity) of Aurora A kinase. The therapeutically effective amount of a compound or a pharmaceutically acceptable salt thereof may decrease (i.e. inhibit) the binding activity Aurora A kinase with a Myc family protein (e.g. c-Myc, N-Myc, L-Myc, or human Myc). The Myc family protein may be c-Myc. The Myc family protein may be N-Myc. The Myc family protein may be L-Myc. In embodiments, the administration of the therapeutically effective amount of a compound, or a pharmaceutically acceptable salt thereof modulates (i.e. increases) the degradation of a Myc family protein (e.g. c-Myc, N-Myc, L-Myc, or human Myc). The increased degradation may occur from modulation (e.g. inhibition) of the binding of Myc family protein (e.g. c-Myc, N-Myc, L-Myc, or human Myc) with another protein (e.g. Aurora A Kinase). C-Myc degradation may be modulated. L-Myc degradation may be modulated. N-Myc degradation may be modulated.

In another aspect is a method of treating neuroblastoma. The method includes administering to a subject in need thereof a therapeutically effective amount of a compound having formula (I). In embodiments, the compound of formula (I) has formula CD532.

VI. Embodiments

Embodiment 1 A method of inhibiting the level of activity of Aurora A kinase comprising contacting the Aurora A kinase with an effective amount of a compound, or a pharmaceutically acceptable salt thereof, wherein the compound has the formula:

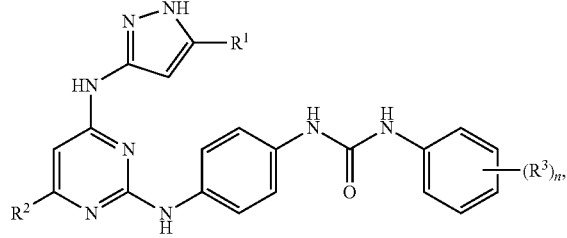

wherein, $R^1$ is a substituted or unsubstituted $C_5$ cycloalkyl, substituted or unsubstituted heterocycloalkyl, or substituted or unsubstituted 5 to 6 membered heteroaryl; $R^2$ is hydrogen, halogen, —$CF_3$, —$CCl_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCH_3$, —$OCF_3$, —$OCHF_2$, —C(O)$CH_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently halogen, —$CF_3$, —$CCl_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCH_3$, —$OCF_3$, —$OCHF_2$, —C(O)$CH_3$, unsubstituted alkyl, or unsubstituted heteroalkyl; and n is independently an integer from 0 to 5

Embodiment 2 The method of embodiment 1, wherein the Aurora A kinase is in vitro.

Embodiment 3 The method of embodiment 1, wherein the Aurora A kinase is in a subject.

Embodiment 4 The method of any one of embodiments 1 to 3, wherein the activity is Aurora A kinase enzymatic activity.

Embodiment 5 The method of any one of embodiments 1 to 3, wherein the activity is Aurora A kinase protein binding activity.

Embodiment 6 The method of embodiment 5, wherein the Aurora A kinase protein binding activity is Aurora A kinase-Myc family protein binding activity.

Embodiment 7 The method of embodiment 6, wherein the Aurora A kinase-Myc family protein binding activity is Aurora A kinase-MYCN protein binding activity.

Embodiment 8 The method of embodiment 6, wherein the Aurora A kinase-Myc family protein binding activity is Aurora A kinase-c-Myc protein binding activity.

Embodiment 9 A method of treating a Myc family protein pathway associated cancer in a patient in need of such treatment, the method comprising administering a therapeutically effective amount of a compound, or a pharmaceutically acceptable salt thereof, to the patient, wherein the compound has the formula:

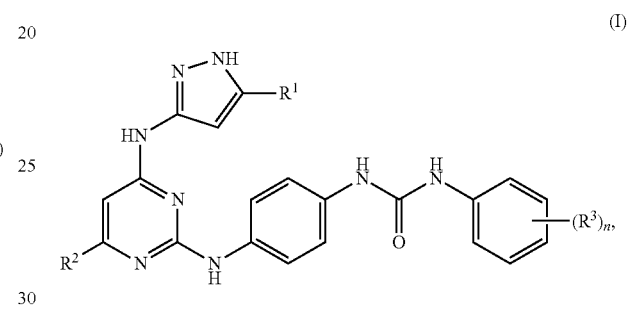

wherein, $R^1$ is a substituted or unsubstituted $C_5$ cycloalkyl, substituted or unsubstituted heterocycloalkyl, or substituted or unsubstituted 5 to 6 membered heteroaryl; $R^2$ is hydrogen, halogen, —$CF_3$, —$CCl_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCH_3$, —$OCF_3$, —$OCHF_2$, —C(O)$CH_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently halogen, —$CF_3$, —$CCl_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCH_3$, —$OCF_3$, —$OCHF_2$, —C(O)$CH_3$, unsubstituted alkyl, or unsubstituted heteroalkyl; and n is independently an integer from 0 to 5.

Embodiment 10 The method of embodiment 9, wherein the cancer is a Myc family protein associated cancer.

Embodiment 11 The method of any one of embodiments 9 to 10, wherein the cancer is an Aurora A kinase associated cancer.

Embodiment 12 The method of any one of embodiments 9 to 11, wherein the cancer is neuroblastoma.

Embodiment 13 The method of any one of embodiments 9 to 11, wherein the cancer is breast cancer.

Embodiment 14 A method of inhibiting the level of activity of a Myc family protein in a cell comprising contacting the cell with an effective amount of a compound, or a pharmaceutically acceptable salt thereof, wherein the compound has the formula:

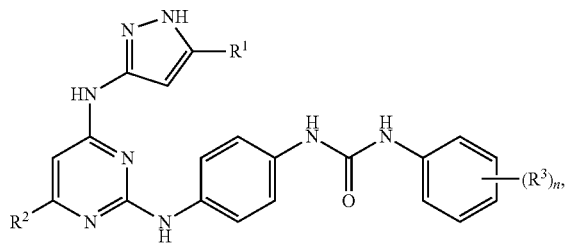

(I)

wherein, R¹ is a substituted or unsubstituted C₅ cycloalkyl, substituted or unsubstituted heterocycloalkyl, or substituted or unsubstituted 5 to 6 membered heteroaryl; R² is hydrogen, halogen, —CF₃, —CCl₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCH₃, —OCF₃, —OCHF₂, —C(O)CH₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R³ is independently halogen, —CF₃, —CCl₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCH₃, —OCF₃, —OCHF₂, —C(O)CH₃, unsubstituted alkyl, or unsubstituted heteroalkyl; and n is independently an integer from 0 to 5.

Embodiment 15 The method of embodiment 14, wherein the level of activity of a Myc family protein is an amount of the Myc family protein.

Embodiment 16 The method of any one of embodiments 14 to 15, wherein the Myc family protein is MYCN protein.

Embodiment 17 The method of any one of embodiments 14 to 15, wherein the Myc family protein is c-Myc protein.

Embodiment 18 The method of any one of embodiments 1 to 17, wherein R¹ is a substituted or unsubstituted C₅ cycloalkyl, substituted or unsubstituted 5 to 6 membered heterocycloalkyl, or substituted or unsubstituted 5 to 6 membered heteroaryl.

Embodiment 19 The method of any one of embodiments 1 to 17, wherein R¹ is an unsubstituted C₅ cycloalkyl, unsubstituted 5 to 6 membered heterocycloalkyl, or unsubstituted 5 to 6 membered heteroaryl.

Embodiment 20 The method of any one of embodiments 1 to 17, wherein R¹ is an unsubstituted C₅ cycloalkyl.

Embodiment 21 The method of any one of embodiments 1 to 17, wherein R¹ is unsubstituted 5 to 6 membered heterocycloalkyl.

Embodiment 22 The method of any one of embodiments 1 to 17, wherein R¹ is an unsubstituted 5 to 6 membered heteroaryl.

Embodiment 23 The method of any one of embodiments 1 to 17, wherein R¹ is an unsubstituted cyclopentyl.

Embodiment 24 The method of any one of embodiments 1 to 17, wherein R¹ is an unsubstituted furanyl.

Embodiment 25 The method of any one of embodiments 1 to 24, wherein R² is hydrogen, halogen, —CF₃, —CCl₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCH₃, —OCF₃, —OCHF₂, —C(O)CH₃, substituted or unsubstituted C₁-C₈ alkyl, substituted or unsubstituted 2 to 8 membered heteroalkyl, substituted or unsubstituted C₃-C₈ cycloalkyl, substituted or unsubstituted 3 to 8 membered heterocycloalkyl, substituted or unsubstituted C₆-C₁₀ aryl, or substituted or unsubstituted 5 to 10 membered heteroaryl.

Embodiment 26 The method of any one of embodiments 1 to 24, wherein R² is hydrogen, halogen, —CF₃, —CCl₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCH₃, —OCF₃, —OCHF₂, —C(O)CH₃, substituted or unsubstituted C₁-C₄ alkyl, substituted or unsubstituted 2 to 4 membered heteroalkyl, substituted or unsubstituted C₃-C₅ cycloalkyl, substituted or unsubstituted 3 to 5 membered heterocycloalkyl, substituted or unsubstituted C₆-C₁₀ aryl, or substituted or unsubstituted 5 to 9 membered heteroaryl.

Embodiment 27 The method of any one of embodiments 1 to 24, wherein R² is hydrogen, halogen, —CF₃, —CCl₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCH₃, —OCF₃, —OCHF₂, or —C(O)CH₃.

Embodiment 28 The method of any one of embodiments 1 to 24, wherein R² is hydrogen, substituted or unsubstituted C₁-C₄ alkyl, substituted or unsubstituted 2 to 4 membered heteroalkyl, substituted or unsubstituted C₃-C₅ cycloalkyl, substituted or unsubstituted 3 to 5 membered heterocycloalkyl, substituted or unsubstituted C₆-C₁₀ aryl, or substituted or unsubstituted 5 to 9 membered heteroaryl.

Embodiment 29 The method of any one of embodiments 1 to 24, wherein R² is hydrogen, unsubstituted C₁-C₄ alkyl, unsubstituted 2 to 4 membered heteroalkyl, unsubstituted C₃-C₅ cycloalkyl unsubstituted 3 to 5 membered heterocycloalkyl, unsubstituted C₆-C₁₀ aryl, or unsubstituted 5 to 9 membered heteroaryl.

Embodiment 30 The method of any one of embodiments 1 to 24, wherein R² is hydrogen or unsubstituted C₁-C₄ alkyl.

Embodiment 31 The method of any one of embodiments 1 to 24, wherein R² is hydrogen or unsubstituted methyl.

Embodiment 32 The method of any one of embodiments 1 to 24, wherein R² is hydrogen.

Embodiment 33 The method of any one of embodiments 1 to 32, wherein R³ is independently halogen, —CF₃, —CCl₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCH₃, —OCF₃, —OCHF₂, —C(O)CH₃, unsubstituted C₁-C₄ alkyl, or unsubstituted 2 to 4 membered heteroalkyl.

Embodiment 34 The method of any one of embodiments 1 to 32, wherein R³ is independently halogen, —CF₃, —CCl₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHOH, —OCH₃, —OCF₃, —OCHF₂, —C(O)CH₃, or unsubstituted methyl.

Embodiment 35 The method of any one of embodiments 1 to 32, wherein R³ is independently —CF₃.

Embodiment 36 The method of any one of embodiments 1 to 35, wherein n is 1.

Embodiment 37 The method of any one of embodiments 1 to 35, wherein n is 0.

Embodiment 38 The method of any one of embodiments 1 to 35, wherein n is 2.

Embodiment 39 The method of any one of embodiments 1 to 35, wherein n is 3.

Embodiment 40 The method of any one of embodiments 1 to 35, wherein n is 4.

Embodiment 41 The method of any one of embodiments 1 to 35, wherein n is 5.

Embodiment 42 The method of any one of embodiments 1 to 36, wherein the compound has the formula:

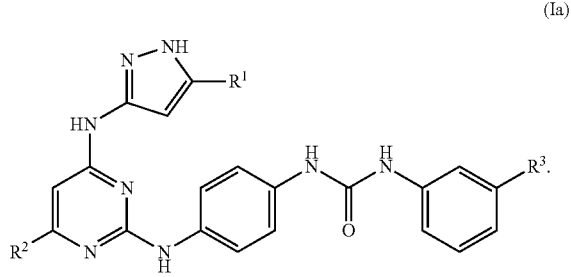

(Ia)

Embodiment 43 The method of embodiment 42, wherein the compound is

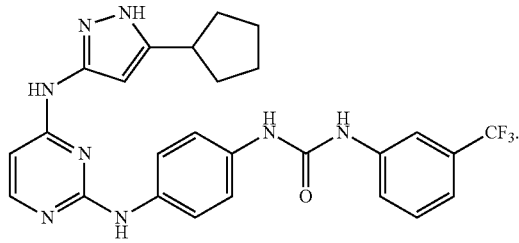 [SMILES: O=C(Nc1ccc(Nc2nccc(Nc3cc(C4CCCC4)[nH]n3)n2)cc1)Nc1cccc(C(F)(F)F)c1]

Embodiment 44 A compound, or a pharmaceutically acceptable salt thereof, having the formula:

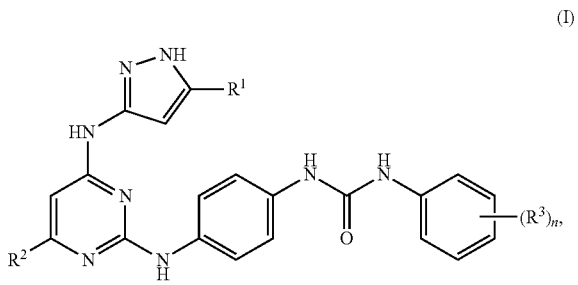

(I)

wherein, $R^1$ is a substituted or unsubstituted $C_5$ cycloalkyl, substituted or unsubstituted heterocycloalkyl, or substituted or unsubstituted 5 to 6 membered heteroaryl; $R^2$ is hydrogen, halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCH$_3$, —OCF$_3$, —OCHF$_2$, —C(O)CH$_3$, substituted or unsubstituted alkyl, substituted or unsubstituted cycloalkyl, substituted or unsubstituted heterocycloalkyl, substituted or unsubstituted aryl, or substituted or unsubstituted heteroaryl; $R^3$ is independently halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCH$_3$, —OCF$_3$, —OCHF$_2$, —C(O)CH$_3$, unsubstituted alkyl, or unsubstituted heteroalkyl; and n is independently an integer from 0 to 5.

Embodiment 45 A pharmaceutical composition comprising a pharmaceutically acceptable excipient and a compound, or a pharmaceutically acceptable salt thereof, of embodiment 44.

Embodiment 46 The pharmaceutical composition of embodiment 45 comprising a second agent.

Embodiment 47 The pharmaceutical composition of embodiment 46, wherein the second agent is an anti-cancer agent.

Embodiment 48 The compound of embodiment 49, wherein $R^1$ is a substituted or unsubstituted $C_5$ cycloalkyl, substituted or unsubstituted 5 to 6 membered heterocycloalkyl, or substituted or unsubstituted 5 to 6 membered heteroaryl.

Embodiment 49 The compound of any one of embodiments 44 or 48, wherein $R^1$ is an unsubstituted $C_5$ cycloalkyl.

Embodiment 50 The compound of any one of embodiments 44 or 48-49, wherein $R^1$ is unsubstituted 5 to 6 membered heterocycloalkyl.

Embodiment 51 The compound of any one of embodiments 44 or 48-50, wherein $R^1$ is an unsubstituted 5 to 6 membered heteroaryl.

Embodiment 52 The compound of any one of embodiments 44 or 48-51, wherein $R^1$ is an unsubstituted cyclopentyl.

Embodiment 53 The compound of any one of embodiments 44 or 48-52, wherein $R^1$ is an unsubstituted furanyl.

Embodiment 54 The compound of any one of embodiments 44 or 48-53, wherein $R^2$ is hydrogen, halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCH$_3$, —OCF$_3$, —OCHF$_2$, —C(O)CH$_3$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

Embodiment 55 The compound of any one of embodiments 44 or 48-54, wherein $R^2$ is hydrogen, halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCH$_3$, —OCF$_3$, —OCHF$_2$, or —C(O)CH$_3$.

Embodiment 56 The compound of any one of embodiments 44 or 48-55, wherein $R^2$ is hydrogen, substituted or unsubstituted $C_1$-$C_4$ alkyl, substituted or unsubstituted 2 to 4 membered heteroalkyl, substituted or unsubstituted $C_3$-$C_5$ cycloalkyl, substituted or unsubstituted 3 to 5 membered heterocycloalkyl, substituted or unsubstituted $C_6$-$C_{10}$ aryl, or substituted or unsubstituted 5 to 9 membered heteroaryl.

Embodiment 57 The compound of any one of embodiments 44 or 48-56, wherein $R^2$ is hydrogen or unsubstituted $C_1$-$C_4$ alkyl.

Embodiment 58 The compound of any one of embodiments 44 or 48-57, wherein $R^2$ is hydrogen or unsubstituted methyl.

Embodiment 59 The compound of any one of embodiments 44 or 48-58, wherein $R^2$ is hydrogen.

Embodiment 60 The compound of any one of embodiments 44 or 48-59, wherein $R^3$ is independently halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCH$_3$, —OCHF$_2$, —C(O)CH$_3$, unsubstituted C$_1$-C$_4$ alkyl, or unsubstituted 2 to 4 membered heteroalkyl.

Embodiment 61 The compound of any one of embodiments 44 or 48-60, wherein $R^3$ is independently halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHOH, —OCH$_3$, —OCHF$_2$, —C(O)CH$_3$, or unsubstituted methyl.

Embodiment 62 The compound of any one of embodiments 44 or 48-61, wherein said compound has the formula:

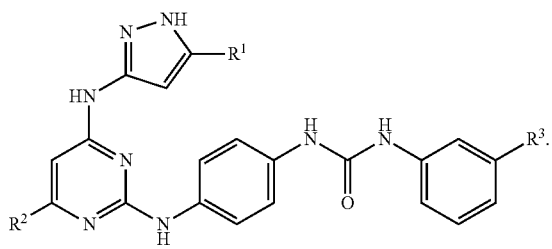

(Ia)

Embodiment 63 The compound of any one of embodiments 46 or 62, wherein said compound has the formula:

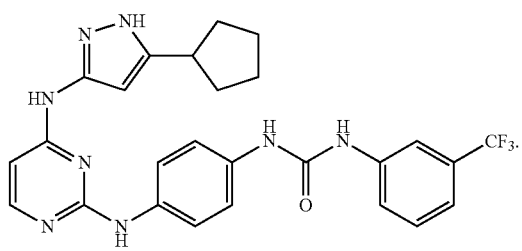 [SMILES: O=C(Nc1ccc(Nc2nccc(Nc3cc(C4CCCC4)[nH]n3)n2)cc1)Nc1cccc(C(F)(F)F)c1]

VII. Examples

The MYC family member MYCN, named based on its association with amplification in the childhood tumor neuroblastoma, is stabilized by Aurora Kinase A (Aurora A, Aurora A kinase) in a kinase-independent fashion involving protein-protein interaction (Otto et al., 2009). Independent of its effects on MYCN, Aurora Kinase A is an attractive cancer target, as it regulates entry into mitosis, maturation of centrosomes, cytokinesis, and formation of the bipolar spindle, in part through phosphorylation of key regulators of proliferation and survival such as p53, BRCA1, and Histone H3 (Scrittori et al., 2001; Crosio et al., 2002; Liu et al., 2004; Ouchi, 2004; Zhao et al., 2008).

To identify conformation-disrupting compounds to drug MYCN, a set of candidate inhibitors predicted to induce a large structural shift in Aurora A were synthesized by appending a range of type II (inactive state-binding) pharmacophores to two different kinase inhibitor scaffolds. Candidate compounds were used to treat MYCN-amplified neuroblastoma cell lines. Levels of MYCN were assayed by immunoblot, and a lead compound, CD532, was identified. CD532 inhibited Aurora A at low nanomolar concentrations, and induced potent degradation of MYCN and blockade of p-Histone H3, the latter a measure of Aurora kinase inhibition. Co-crystal structures of Aurora A with and without CD532 show that CD532 induced a pronounced shift of structural features in the kinase domain of Aurora A, as compared to Aurora A alone, or bound to either ATP or to the clinical inhibitors VX-680 or MLN8054. CD532 represents an active site-binding allosteric inhibitor of Aurora Kinase A that blocks a stabilizing function of Aurora A for MYCN protein.

It is hypothesized that the kinase-independent stabilization of MYCN requires a distinct conformation of this protein kinase, and that conformation-disrupting inhibitors (CDs) of Aurora Kinase A will perturb these protein-protein interactions, effecting MYCN degradation. An allosteric inhibitor is generally defined as one that binds an enzyme outside the active site to effect a change in activity at the active site. Herein this definition is extended in the reverse direction, whereby an allosteric inhibitor binds an enzyme at the active site to effect a change in activity outside the active site. In this context, an ATP-mimetic ligand that binds the active site of Aurora Kinase A to alter its kinase-independent stabilization of MYCN is described herein. There are several recent examples of allosteric inhibitors for the treatment of cancer including arsenic trioxide, an anti-leukemic which binds to zinc fingers within the PML-RARα fusion protein of acute promyelocytic leukemia to induce a conformational change favoring oligomerization and eventual degradation (Zhang et al., 2010) and biculutamide which binds to the androgen receptor to block transcription in prostate cancer (Osguthorpe and Hagler, 2011). Enzymes, including but not exclusive to kinases like Aurora A, have numerous non-enzymatic activities including scaffolding, regulation, and localization of other proteins. The general approach outlined here, targeting an enzyme's active site to effect an allosteric change outside of the enzymatic active site, also has potential for targeting other undruggable oncoprotein targets, such as the RAS superfamily of GTPases.

Neuroblastoma is the most common extracranial solid tumor of childhood and MYCN amplification is the best-described genetic lesion marking high-risk, chemotherapy resistant disease. Targeted expression of MYCN drives neuroblastoma in systems from mice to zebrafish (Weiss et al., 1997; Zhu et al., 2012). It has been possible to finesse destabilization of MYCN through blockade of upstream PI3K/mTOR inhibition (Chesler et al., 2006; Chanthery et al., 2012). An alternative approach to block MYCN and its transcriptional targets is through use of BRD4-based bromodomain inhibitors ((Mertz et al., 2011), Frumm et al, Cancer Discovery). Herein is described a different strategy to block MYCN in cancer. These interventions, at distinct nodes in the same oncogenic pathway, present a unique opportunity for combinatorial, targeted therapeutics to block emergent resistance, while maximizing the blockade of MYCN in neuroblastoma and potentially in other MYCN- and MYC-driven cancers.

Cell Culture, Inhibitors, and Western Blotting

Neuroblastoma tumor cell lines were obtained from the University of California San Francisco Cell Culture Facility (Kelly, SK-N-BE2, and SH-EP). SMS-KCN, SHEP MYCN$^{wt}$ and MYCN$^{T58A/S62A}$ cells were obtained. All cells were grown in RPMI with 10% FBS. Neuroblastoma cells were harvested and lysed with Cell Signaling Lysis buffer+ 1% SDS, sonicated and supernatants boiled in LDS sample buffer (Invitrogen). Western blots were performed as described previously (Chanthery et al., 2012), with primary antibodies to MYCN (ab24193, Abcam), Histone H3, P-Histone H3 (S10), Aurora A (Cell signaling), and GAPDH (Millipore). Western blot quantitation performed with ImageJ software. VX-680 (S1048) and MLN8237 (S1133) were obtained from Selleck chemicals.

Flow Cytometry and Viability

Neuroblastoma cells were treated for the indicated time, trypsinized, washed, stained with Dylight 800 at 0.3 µg/mL (Pierce, 46421), fixed with 1.5% PFA, and permeabilized with 100% methanol. Cells were then stained with antibodies against p-MPM2 (Millipore, 16-155), p-pan-Aurora (Cell Signaling, 2914), MYCN (Thermo, PA5-17403), rabbit IgG (Invitrogen, A10542), or mouse IgG (BioLegend, 405307). Cells were stained with DAPI at 0.3 µg/mL (Invitrogen, D21490) and analyzed on the BD LSR II flow cytometer. For cell cycle analysis, cells were stimulated with EdU for 2 hours prior to harvest, then probed using the Click-iT EdU Flow Cytometry Assay Kit (Invitrogen, C10424). Cells were stained with propidium iodide (BD, 556547) and analyzed on the BD FACSCalibur flow cytometer. Data was gated using Cytobank. For viability studies, neuroblastoma cells were plated in 96-well plates at a density of 1,000 cells/well for SHEP or 4,000 cells/well for Kelly or SK-N-BE2 cells, then incubated with indicated concentrations of drug for 72 hours at 37° C. Plates were frozen at −80° C. to induce cell lysis. CyQUANT reagent mixture (Invitrogen, C7026) was added to thawed plates, then fluorescence was measured. Alternatively, resazurin (Sigma-Aldrich, R7017) was added directly to wells following drug treatment then incubated for 4 hours at 37° C. prior to measuring fluorescence. Data was analyzed using GraphPad Prism software.

Pulldowns

Cells were pretreated with MG-132 (Calbiochem, 474790) at 5 µg/ml for 4 hours and with drug (CD532, MLN8237, or VX-680) for 2 hours before lysis with TNN lysis buffer in the presence of protease inhibitor (Sigma-Aldrich, P8849). Pulldowns were performed with anti-N-Myc antibody (Santa Cruz, SC-53993) and Protein G sepharose beads (Sigma-Aldrich, P3296). Immunoblots were performed as described above.

Chemical Synthesis

Starting materials were purchased from Sigma-Aldrich or Alfa Aesar. Unless otherwise noted, reactions were performed in dry, argon-charged, glass roundbottom flasks and monitored by thin layer chromatography (TLC) or liquid chromatography-mass spectrometry (LCMS). Compounds were characterized by LCMS and nuclear magnetic resonance (NMR) spectroscopy. LCMS retention times (RT) are reported in minutes based on a gradient of 5-95% ACN/H$_2$O from t=0.1-1.9 min. NMR shifts (δ) are reported in ppm as singlets (s), doublets (d), quartets (q), quintets (quin), or multiplets (m). High-performance liquid chromatography (HPLC) was conducted using a Waters 2545 binary gradient module, Waters 2767 sample manager, and Waters 2998 photodiode array detector running MassLynx v4.1. Flash/ silica gel chromatography was performed on an AnaLogix Intelliflash using SuperFlash Si50 columns (Agilent).

3-cyclopentyl-3-oxopropanenitrile (JM2)

To a dried, argon-charged roundbottom flask with large stir bar was added anhydrous tetrahydrofuran (160 ml), which was then cooled to −78° C. before addition of 2.5 M n-Butyllithium in hexanes (64 mL, 160 mmol). Reaction was stirred for 5 minutes before addition of anhydrous acetonitrile (8.48 mL, 160 mmol) dropwise over 5 minutes. Reaction was stirred for 90 minutes at −78° C., followed by dropwise addition methylcyclopentane carboxylate (10.28 ml, 80.4 mmol) over 10 minutes. Reaction was allowed to stir for another 2 hours at −78° C., allowed to warm to room temperature, and stirred for an additional 30 minutes. Reaction was quenched with 240 ml H$_2$O and stirred until all solids dissolved. Aqueous layer was washed with ether (3×120 ml), and aqueous layer was slowly brought to pH 3.0 with dropwise addition of HCl, forming visible precipitate of product, which was extracted from aqueous with ether (3×120 ml), dried with MgSO$_4$, filtered, and evaporated under reduced pressure to afford 10.4 g (75.9 mmol, 94.4% yield) of a viscous yellow oil. Purity of product was sufficient to carry on to next step. LCMS (RT=1.35): 137.2 (100%); 138.2 (10%); 139.2 (3%).

5-cyclopentyl-1H-pyrazol-3-amine (JM3)

3-cyclopentyl-3-oxopropanenitrile (10.4 g, 75.9 mmol) and hydrazine monohydrate 65% (7.8 ml, 152 mmol) were dissolved in 95% EtOH (85 ml). Reaction was heated to reflux for 2.5 hours and followed to completion by thin layer chromatography. Excess hydrazine and ethanol were evaporated under reduced pressure, crude product dissolved in CHCl$_3$, and purified by flash chromatography with 0-10% MeOH in CHCl$_3$. Recovered 8.93 g (59 mmol, 77.7% yield). LCMS (RT=0.64): 151.3 (100%); 152.4 (14%); 153.4 (4%). NMR, $^1$H, DMSO (400 MHz): 11.07 (s, 1H), 5.18 (s, 1H), 4.42 (s, 2H), 2.86 (quin, 1H), 1.91-1.48 (m, 8H).

2-chloro-N-(5-cyclopentyl-1H-pyrazol-3-yl)pyrimidin-4-amine (JM5)

5-cyclopentyl-1H-pyrazol-3-amine (1.51 g, 10.0 mmol) and 2,4-dichloropyrimidine (1.49 g, 10 mmol) were dissolved in a 1:1 mixture of THF:H$_2$O (70 ml), and KOAc (98.15 g, 300 mmol) was added to the mixture. Reaction was stirred vigorously at 55° C. for 48 hours. Organic layer was separated and evaporated under reduced pressure, dissolved in CH$_2$Cl$_2$ (45 ml), and kept at −20° C. for 3 hours. Precipitated solid was filtered, washed with cold CH$_2$Cl$_2$ (15 ml), and dried to yield 0.46 g of N2-(4-aminophenyl)-N4-(5-cyclopentyl-1H-pyrazol-3-yl)pyrimidine-2,4-diamine (1.74 mmol, 17.4% yield). LCMS (RT=1.31): 262.9 (100%); 264.9 (60%); 263.9 (25%); 265.8 (10%). NMR, $^1$H, DMSO (400 MHz): 12.15 (s, 1H), 10.26 (s, 1H), 8.12 (s, 1H), 2.99 (quin, 1H), 1.98-1.50 (m, 8H).

N2-(4-aminophenyl)-N4-(5-cyclopentyl-1H-pyrazol-3-yl)pyrimidine-2,4-diamine (JM8)

JM5 (78 mg, 0.3 mmol) and p-phenylenediamine (35.6 mg, 0.33 mmol) were dissolved in n-butanol and stirred at 90° C. for 3 hrs. Solvent was evaporated under reduced pressure and crude product was purified by HPLC (10-75% ACN/H$_2$O) and lyophilized to give 32 mg of JM8 (0.096 mmol, 32% yield). LCMS (RT=0.84): 335.3 (100%); 336.3 (25%); 337.4 (4%). NMR, $^1$H, DMSO (400 MHz): 9.62 (s, 1H), 8.75 (s, 1H), 8.11 (s, 1H), 7.83 (d, 1H), 7.23 (d, 2H), 6.50 (m, 2H), 6.26 (s, 1H), 6.17 (s, 1H), 2.94 (quin, 1H), 1.94-1.53 (m, 8H).

1-(4-((4-((5-cyclopentyl-1H-pyrazol-3-yl)amino)pyrimidin-2-yl)amino)phenyl)-3-(3-(trifluoromethyl)phenyl)urea (CD532)

JM8 (13.5 mg, 40.3 µmol) was dissolved in DMF (2 ml) in a dry, argon-charged roundbottom flask. 3-(trifluoromethyl)phenyl isocyanate (6.23 µl, 44.3 µmol) was added and reaction was stirred overnight under argon gas. Crude product was purified by HPLC (10-75% ACN/H$_2$O) and 3.6 mg of NHC53-2 (6.89 µmol, 17% yield) was recovered as a white powder. LCMS (RT=1.32): 522.2 (100%); 523.3 (30%); 524.4 (5%). NMR, $^1$H, DMSO (400 MHz): 9.69 (s, 1H), 9.51 (s, 1H), 9.29 (s, 1H), 8.94 (s, 1H), 8.25 (s, 1H), 8.04 (s, 1H), 7.91 (d, 1H), 7.65-7.51 (m, 3H), 7.45 (quin, 1H), 7.40-7.32 (m, 2H), 7.23 (d, 1H), 6.32 (s, 1H), 6.19 (s, 1H), 2.93 (quin, 1H), 2.06-1.39 (m, 8H).

3-[4-({4-[(5-cyclopentyl-1H-pyrazol-3-yl)amino]pyrimidin-2-yl}amino)phenyl]-1-phenylurea (JM25, p183)

JM8 (3.0 mg, 8.95 µmol) was dissolved in dry DMF (3 ml) in a dry, argon-charged flask, and isocyanatobenzene (1.07 µl, 9.84 µmol) was added. Reaction was stirred at ambient temperature for 1 hour under positive pressure. Solvent was evaporated under reduced pressure, and product was purified by HPLC (30-70% ACN/H$_2$O) to recover 0.7 mg (17% yield) of a white powder. LCMS (RT=1.22): 454.3 (100%), 455.4 (30%), 456.4 (4%). NMR, $^1$H DMSO (400 MHz): 9.51 (s, 1H), 8.94 (s, 1H), 8.68 (s, 1H), 8.58 (s, 1H), 8.14 (s, 1H), 7.92 (s, 1H), 7.57 (d, 2H), 7.42 (m, 2H), 7.32 (d, 2H), 7.24 (d, 2H), 6.91 (s, 1H), 6.33 (s, 1H), 6.18 (s, 1H), 3.70 (s, 1H), 2.96 (s, 1H), 1.98-1.43 (m, 8H).

3-[4-({4-[(5-cyclopentyl-1H-pyrazol-3-yl)amino]pyrimidin-2-yl}amino)phenyl]-1-[2-fluoro-5-(trifluoromethyl)phenyl]urea (JM192)

JM8 (5 mg, 14.9 µmol) and 1-fluoro-2-isocyanato-4-(trifluoromethyl)benzene (2.37 µl, 16.4 µmol) were reacted and purified in a manner similar to JM25 to recover 2.5 mg (31% yield) of a white powder. LCMS (RT=1.37): 540.3 (100%), 541.3 (30%), 542.3 (4%). NMR, $^1$H, DMSO (400 MHz): 9.53 (s, 1H), 9.31 (s, 1H), 9.08 (s, 1H), 8.98 (s, 1H), 8.60 (d, 1H), 8.29 (s, 1H), 7.91 (d, 1H), 7.60 (d, 2H), 7.46-7.31 (m, 4H), 6.32 (s, 1H), 6.20 (s, 1H), 2.95 (quin, 1H), 1.98-1.44 (m, 8H).

2-chloro-N-(5-cyclopentyl-1H-pyrazol-3-yl)-6-methylpyrimidin-4-amine (JM4)

5-cyclopentyl-1H-pyrazol-3-amine (1.51 g, 10 mmol) and 2,4-dichloro-6-methylpyrimidine (1.63 g, 10 mmol) were dissolved in a 1:1 mixture of THF:H$_2$O (70 ml) and treated with KOAc (29.45 g, 300 mmol). Reaction was stirred vigorously at 55° C. for 48 hrs. Layers were separated, organic layer was evaporated under reduced pressure, and resulting solid was purified by flash chromatography (2-10% MeOH/CHCl$_3$) to afford 1.69 g (61% yield) of a white powder. LCMS (RT=1.26): 277.2 (100%); 279.2 (60%); 278.3 (25%); 280.2 (8%). NMR, $^1$H, DMSO (400 MHz): 8.28 (s, 1H), 7.35 (s, 1H), 6.64 (s, 1H), 5.25 (s, 1H), 2.05 (s, 3H), 1.72-1.51 (m, 8H).

N2-(4-aminophenyl)-N4-(5-cyclopentyl-1H-pyrazol-3-yl)-6-methylpyrimidine-2,4-diamine (JM14)

2-chloro-N-(5-cyclopentyl-1H-pyrazol-3-yl)-6-methylpyrimidin-4-amine (73 mg, 0.26 mmol) and p-phenylenediamine (56.2 mg, 0.52 mmol) were dissolved in n-BuOH (3 mL) and stirred at 90° C. for 5 hours. Reaction was allowed to cool to ambient temperature, solvent was evaporated under reduced pressure, and product was purified by HPLC (10-75% ACN/H$_2$O) to afford 33 mg (36% yield) of JM14. LCMS (RT=0.84): 349.3 (100%); 350.3 (22%); 351.3 (4%). NMR, $^1$H, CDCl$_3$: 8.54 (s, 1H), 7.20 (d, 2H), 6.62 (d, 2H), 2.90 (quin, 1H), 2.22 (s, 3H), 1.98-1.93 (m, 2H), 1.75-1.43 (m, 6H).

1-(4-((4-((5-cyclopentyl-1H-pyrazol-3-yl)amino)-6-methylpyrimidin-2-yl)amino)phenyl)-3-(3-(trifluoromethyl)phenyl)urea (CD15)

To a dry, argon-charged roundbottom flask with stir bar was added JM14 (17 mg, 0.049 mmol) and dry DMF. 3-(trifluoromethyl)phenyl isocyanate (13.3 µL, 1.1 eq) was added by syringe and reaction was stirred under argon until depletion of JM14 by LCMS (2 hours). Solvent was evaporated under reduced pressure and solid was dissolved in minimal DMSO for purification by HPLC (10-90% ACN/H$_2$O) to afford 4.2 mg (16% yield) of a white powder. LCMS (RT=1.33): 536.3 (100%); 537.3 (40%); 538.3 (8%). NMR, $^1$H, DMSO (400 MHz): 9.39 (s, 1H), 9.28 (s, 1H), 8.93 (s, 1H), 8.89 (s, 1H), 8.17 (s, 1H), 8.03 (s, 1H), 7.61 (d, 2H), 7.54 (d, 1H), 7.44 (t, 1H), 7.32 (d, 2H), 7.24 (d, 1H), 6.28-6.09 (b, 2H), 2.94 (quin, 1H), 2.14 (s, 3H), 2.02-1.88 (m, 2H), 1.77-1.45 (m, 6H).

3-cyclohexyl-3-oxopropanenitrile (JM18)

To a dried, argon-charged roundbottom flask with large stir bar was added anhydrous tetrahydrofuran (80 ml), which was cooled to −78° C. before addition of 2.5 M n-Butyllithium in hexanes (32 mL, 80 mmol). Reaction was stirred for 5 minutes before addition of anhydrous acetonitrile (4.23 mL, 80 mmol) dropwise over 5 minutes. Reaction was stirred for 90 minutes at −78° C., followed by dropwise addition of methylcyclohexane carboxylate (5.72 ml, 40 mmol) over 15 minutes. Reaction was allowed to stir for another 2 hours at −78° C., allowed to warm to room temperature, and stirred for an additional 30 minutes. Reaction was quenched with 100 ml H$_2$O and stirred until all solids dissolved. Aqueous layer was washed with ether (2×100 ml), and aqueous layer was slowly brought to pH 3.0 with dropwise addition of HCl, forming visible precipitate of product, which was extracted from aqueous with ether (3×100 ml), dried with MgSO$_4$, filtered, and evaporated under reduced pressure to yield 5.3 g (87.6% yield) of a viscous yellow oil. Purity of product was sufficient to carry on to next step. LCMS (RT=1.36): 151.2 (100%), 152.2 (12%), 153.2 (3%).

5-cyclohexyl-1H-pyrazol-3-amine (JM19)

3-cyclohexyl-3-oxopropanenitrile (5.3 g, 35 mmol) was dissolved in 95% EtOH (45 ml), to which was added hydrazine monohydrate (3.5 ml, 70 mmol). Reaction was stirred under reflux for 2.5 hrs, solvent was evaporated under reduced pressure, and product was purified by flash chromatography (0-10% MeOH/CHCl$_3$) to give 3.52 g (61% yield) of a viscous reddish oil. LCMS (RT=0.89): 165.3 (100%), 166.3 (20%), 167.3 (8%). NMR, $^1$H, DMSO (400 MHz): 10.97 (s, 1H), 5.13 (s, 1H), 4.34 (s, 2H), 2.39 (m, 1H), 1.80-1.15 (m, 10H).

2-chloro-N-(5-cyclohexyl-1H-pyrazol-3-yl)-6-methylpyrimidin-4-amine (JM20)

5-cyclohexyl-1H-pyrazol-3-amine (1.65 g, 10 mmol) and 2,4-dichloro-6-methylpyrimidine (1.63 g, 10 mmol) were dissolved in a 1:1 mixture of THF/H$_2$O (70 ml) in a roundbottom flask with stir bar. Reaction was treated with KOAc (30 eq, 29.45 g) and stirred vigorously for 48 hours at 55° C. Organic layer was separated and evaporated under reduced pressure, and crude product was dissolved in CHCl$_3$ (10 ml) and purified by flash column chromatography (0-10% MeOH/CHCl$_3$) to recover 1.14 g (39% yield) of a white powder. LCMS (RT=1.51): 291.3 (100%), 293.2 (60%), 292.3 (28%), 294.2 (10%). NMR, $^1$H, DMSO (400 MHz): 9.87 (s, 1H), 9.09 (s, 1H), 6.85 (s, 1H), 6.01 (s, 1H), 2.61 (quin, 1H), 2.27 (s, 3H), 1.79-1.21 (m, 10H).

2-N-(4-aminophenyl)-4-N-(5-cyclohexyl-1H-pyrazol-3-yl)-6-methylpyrimidine-2,4-diamine (JM21)

JM20 (231 mg, 0.79 mmol) and p-phenylenediamine (94.0 mg, 0.87 mmol) were dissolved in n-butanol (6 ml) and stirred at 85° C. for 2.5 hrs under argon gas. Solvent was evaporated under reduced pressure, crude solid was dissolved with DMSO (1 ml) and 1:1 ACN/H$_2$O (8 ml) and purified by HPLC (5-25% ACN/H$_2$O) to yield 74 mg (20% yield) of a grey powder. LCMS (RT=0.99): 364.3 (100%), 365.3 (20%), 366.3 (4%). NMR, $^1$H, CDCl$_3$: 8.41 (s, 1H), 7.18 (d, 2H), 6.60 (d, 2H), 6.04 (s, 1H), 5.97 (s, 1H), 3.95 (s, 2H), 3.76 (m, 3H), 2.22 (s, 3H), 1.94-1.09 (m, 10H).

3-[4-({4-[(5-cyclohexyl-1H-pyrazol-3-yl)amino]-6-methylpyrimidin-2-yl}amino)phenyl]-1-[3-(trifluoromethyl)phenyl]urea (CD22)

JM21 (3.9 mg, 10.7 μmol) was dissolved in DMF (3 ml) in a dry, argon-charged roundbottom flask. 3-(trifluoromethyl)phenyl isocyanate (1.65 μl, 11.8 μmol) was added and reaction was stirred for 4 hours under argon gas. Product was purified by HPLC (20-75% ACN/H$_2$O) and 3.05 mg of a white powder (5.54 μmol, 52% yield) was recovered. LCMS (RT=1.40): 550.3 (100%), 551.4 (30%), 552.4 (4%). NMR, $^1$H, DMSO (400 MHz): 9.40 (s, 1H), 9.14 (s, 1H), 8.95 (s, 1H), 8.75 (s, 1H), 8.14 (s, 1H), 8.04 (s, 1H), 7.61 (d, 2H), 7.52-7.42 (m, 2H), 7.33 (d, 2H), 7.25 (d, 1H), 6.17 (b, 2H), 2.53 (quin, 1H), 2.14 (s, 3H), 1.94-1.81 (m, 2H), 1.79-1.65 (m, 2H), 1.59-1.55 (m, 1H), 1.37-1.18 (m, 5H).

3-[4-({4-[(5-cyclohexyl-1H-pyrazol-3-yl)amino]-6-methylpyrimidin-2-yl}amino)phenyl]-1-phenylurea (CD24)

JM21 (3.9 mg, 10.7 μmol) was dissolved in DMF (3 ml) in a dry, argon-charged roundbottom flask. Phenyl isocyanate (1.28 μl, 11.8 μmol) was added and reaction was stirred for 4 hours under argon gas. Product was purified by HPLC (30-75% ACN/H$_2$O) and 2.15 mg of a white powder (4.46 μmol, 42% yield) was recovered. LCMS (RT=1.27): 482.3 (100%), 483.3 (28%), 484.3 (7%). NMR, $^1$H, DMSO (400 MHz): 9.40 (s, 1H), 8.92 (s, 1H), 8.86 (s, 1H), 8.74 (s, 1H), 8.19 (s, 1H), 7.59 (d, 2H), 7.42 (d, 2H), 7.31 (d, 2H), 7.23 (t, 2H), 6.90 (t, 1H), 6.22 (s, 1H), 6.14 (s, 1H), 2.53 (m, 1H), 2.14 (s, 3H), 1.86 (m, 2H), 1.72 (m, 2H), 1.59 (m, 1H), 1.35-1.18 (m, 5H).

2-chloro-N-(5-(furan-2-yl)-1H-pyrazol-3-yl)pyrimidin-4-amine (JM137)

5-(furan-2-yl)-1H-pyrazol-3-amine (0.75 g, 5 mmol) and 2,4-dichloropyrimidine (0.74 g, 5 mmol) were dissolved in a 1:1 mixture of THF/H$_2$O (35 mL). KOAc (30 eq, 14.7 g) were added and reaction was stirred at 55° C. for 72 hours. Layers were separated and organic layer was evaporated completely under reduced pressure. Solid was dissolved in CH$_2$Cl$_2$ (25 mL) and allowed to recrystallize at −20° C. for 2 hours. Precipitate was filtered and washed with cold CH$_2$Cl$_2$ to yield 0.726 g (55.4%) of 2-chloro-N-(5-(furan-2-yl)-1H-pyrazol-3-yl)pyrimidin-4-amine that was carried on to next step. LCMS: 261.1 (100%), 262.3 (12%), 263.1 (33%), 264.3 (2%).

N2-(4-aminophenyl)-N4-(5-(furan-2-yl)-1H-pyrazol-3-yl)pyrimidine-2,4-diamine (JM135)

JM137 (130.5 mg, 0.5 mmol) and p-phenylenediamine (94.5 mg, 0.87 mmol) were dissolved in BuOH (5 mL) and reaction was stirred for 24 hours at 95° C. Upon depletion of JM135 (by LCMS), stir bar was removed and reaction was cooled to −20° C. for 2 hours. Precipitate was filtered and washed with cold BuOH (5 mL) and cold CH$_2$Cl$_2$ (2 mL) to afford 94.6 mg (58%) of JM135 that was carried on directly to the next step. LCMS: 333.3 (100%), 334.3 (20%), 335.4 (2%).

1-(4-((4-((5-(furan-2-yl)-1H-pyrazol-3-yl)amino)pyrimidin-2-yl)amino)phenyl)-3-(3-(trifluoromethyl)phenyl)urea (JM134)

JM135 (30 mg, 0.09 mmol) was dissolved in DMF (0.5 mL) in a dried, argon-charged flask. 3-(trifluoromethyl)phenyl isocyanate (1.1 eq, 14.1 μL) was added and reaction was stirred at ambient temperature for 1 hour. Reaction was diluted in 50% ACN/H$_2$O, precipitate was removed by filtration, and eluate was purified by HPLC to afford 19.9 mg (42%) of JM134. LCMS: 520.3 (100%), 521.2 (33%), 522.1 (4%). NMR, $^1$H, DMSO (400 MHz): 9.90 (s, 1H), 9.17 (s, 1H), 9.12 (s, 1H), 8.77 (s, 1H), 8.14 (s, 1H), 8.02 (s, 1H), 7.98 (d, 1H), 7.71 (s, 1H), 7.62 (d, 2H), 7.55 (d, 1H), 7.48 (t, 1H), 7.37 (d, 2H), 7.26 (d, 1H), 6.72 (d, 1H), 6.55 (d, 1H), 6.54 (d, 1H), 6.31 (s, 1H). NMR, $^{13}$C, DMSO (100 MHz): 164.07, 160.28, 159.87, 156.82, 153.33, 143.10, 141.58, 136.24, 133.79, 130.52, 130.32, 130.01, 129.69, 126.29, 123.58, 122.30, 120.36, 119.78, 118.41, 114.61, 112.21, 106.70, 98.59.

4-nitro-N-[3-(trifluoromethyl)phenyl]benzamide (JM6)

3-(trifluoromethyl)aniline (7.55 ml, 60 mmol) was dissolved in pyridine (200 ml) at ambient temperature under argon gas. 4-nitrobenzoyl chloride (12.25 g, 66 mmol) was added and mixture was refluxed for 4 hrs at 115° C. Reaction was cooled to ambient temperature, poured into ice/water (500 ml), and resulting precipitate was collected by filtration. Precipitate was resuspended in CH$_2$Cl$_2$, left at −20° C. for 2 hrs, and collected by filtration to yield 18 g (96.7%) of a white powder. LCMS (RT=1.69): 310.1 (100%), 311.2 (15%), 312.1 (3%).

4-amino-N-[3-(trifluoromethyl)phenyl]benzamide (JM7)

4-nitro-N-[3-(trifluoromethyl)phenyl]benzamide (1.55 g, 5 mmol) was dissolved in THF (50 ml) containing powdered Zn (30 eq). Glacial acetic acid (20 eq) was added and reaction was stirred vigorously overnight under argon gas. Reaction was filtered with celite and solvent was evaporated under reduced pressure. Resulting solid was recrystallized from $CH_2Cl_2$ to give 0.78 g (55%) of an orange crystalline solid. LCMS (RT=1.44): 280.1 (100%), 281.1 (10%), 282.1 (3%). NMR, $^1H$, DMSO (400 MHz): 10.05 (s, 1H), 8.24 (s, 1H), 8.02 (d, 1H), 7.73 (d, 2H), 7.54 (t, 1H), 7.37 (d, 1H), 6.61 (d, 2H), 5.82 (s, 2H).

N-(4-nitrophenyl)-3-(trifluoromethyl)benzamide (JM9)

4-nitroaniline (2.07 g, 15 mmol) and 3-(trifluoromethyl) benzoyl chloride (3.44 g, 16.5 mmol) were used to generate the title compound in a manner similar to JM6 to afford 3.95 g (84.7%) of a yellow crystalline solid. LCMS (RT=2.04): 310.1 (100%), 311.2 (10%), 312.2 (3%).

N-(4-aminophenyl)-3-(trifluoromethyl)benzamide (JM10) was generated in a manner similar to JM7 to afford 0.58 g (41%) of a beige crystalline powder. LCMS (RT=1.03): 280.2 (100%), 281.3 (25%), 282.3 (3%). NMR, $^1H$, DMSO (400 MHz): 10.10 (s, 1H), 8.25 (s, 1H), 8.23 (d, 1H), 7.92 (d, 1H), 7.75 (t, 1H), 7.37 (d, 2H), 6.55 (d, 2H), 4.97 (s, 2H).

4-({4-[(5-cyclopentyl-1H-pyrazol-3-yl)amino]pyrimidin-2-yl}amino)-N-[3-(trifluoromethyl)phenyl] benzamide (CD12)

JM5 (52.7 mg, 0.2 mmol) and 4-amino-N-[3-(trifluoromethyl)phenyl]benzamide (56.0 mg, 0.2 mmol) were dissolved in n-butanol and heated to 90° C. HCl (30 µl) was added and reaction was stirred under argon gas overnight. Reaction was cooled to ambient temperature, stirbar was removed, and reaction was left at –20° C. for 2 h. Resulting precipitate was filtered and washed with n-butanol (5 ml) and cold ether (5 ml) to afford a white crystalline powder, which was further purified by HPLC (10-65% ACN/$H_2O$) to afford 26.9 mg (24%) of product. LCMS (RT=1.33): 507.3 (100%), 508.4 (25%), 509.4 (5%). NMR, $^1H$, DMSO (400 MHz): 9.65 (s, 1H), 9.57 (s, 1H), 8.23 (s, 1H), 8.15 (s, 1H), 8.04-7.98 (m, 2H), 7.91-7.75 (m, 5H), 7.56 (t, 1H), 7.40 (d, 1H), 6.48 (s, 1H), 6.23 (s, 1H), 2.98 (quin, 1H), 2.02-1.93 (m, 2H), 1.73-1.51 (m, 6H).

N-[4-({4-[(5-cyclopentyl-1H-pyrazol-3-yl)amino] pyrimidin-2-yl}amino)phenyl]-3-(trifluoromethyl) benzamide (CD13)

N-(4-aminophenyl)-3-(trifluoromethyl)benzamide (56 mg, 0.20 mmol) and 2-chloro-N-(5-cyclopentyl-1H-pyrazol-3-yl)pyrimidin-4-amine (52.7 mg, 0.20 mmol) were dissolved in n-butanol (3 ml) and heated to 100° C. HCl (33 µl) was added and precipitate observed to form. Reaction was allowed to proceed overnight, cooled to ambient temperature, and precipitate was filtered and washed with cold butanol (5 ml). Product was purified by HPLC (10-75% ACN/$H_2O$) to yield 19.2 mg of a white powder. LCMS (RT=1.42): 507.3 (100%), 508.2 (35%), 509.2 (4%). NMR, $^1H$, DMSO (400 MHz): 10.37 (s, 1H), 9.58 (s, 1H), 9.12 (s, 1H), 8.29 (s, 1H), 8.26 (d, 1H), 8.14 (s, 1H), 7.98-7.95 (m, 2H), 7.78 (t, 1H), 7.73-7.65 (m, 4H), 6.42 (s, 1H), 6.22 (s, 1H), 2.98 (quin, 1H), 2.05-1.93 (m, 2H), 1.77-1.51 (m, 6H).

4-({4-[(5-cyclopentyl-1H-pyrazol-3-yl)amino]-6-methylpyrimidin-2-yl}amino)-N-[3-(trifluoromethyl) phenyl]benzamide (CD16)

2-chloro-N-(5-cyclopentyl-1H-pyrazol-3-yl)-6-methylpyrimidin-4-amine (83.3 mg, 0.30 mmol) and 4-amino-N-[3-(trifluoromethyl)phenyl]benzamide (84.1 mg, 0.30 mmol) were dissolved in n-butanol (6 ml) and heated to 100° C. HCl was added (50 µl) and reaction allowed to proceed overnight. Mixture was cooled to –20° C. for 2 h and precipitate was filtered and washed with cold butanol (3 ml) and cold ether (5 ml). Product was purified by HPLC (10-65% ACN/$H_2O$) and 18.1 mg (11%) of a white powder was recovered. LCMS (RT=1.33): 521.3 (100%), 522.4 (28%), 523.3 (4%). NMR, $^1H$, DMSO (400 MHz): 10.30 (s, 1H), 9.53 (s, 1H), 9.47 (s, 1H), 8.23 (s, 1H), 8.17 (s, 1H), 8.01 (d, 1H), 7.93-7.87 (m, 4H), 7.55 (t, 1H), 7.39 (d, 1H), 6.38 (s, 1H), 6.17 (s, 1H), 2.97 (quin, 1H), 2.20 (s, 3H), 2.01-1.92 (m, 2H), 1.69-1.51 (m, 6H).

N-[4-({4-[(5-cyclopentyl-1H-pyrazol-3-yl)amino]-6-methylpyrimidin-2-yl}amino)phenyl]-3-(trifluoromethyl)benzamide (CD17)

2-chloro-N-(5-cyclopentyl-1H-pyrazol-3-yl)-6-methylpyrimidin-4-amine (41.7 mg, 0.15 mmol) and N-(4-aminophenyl)-3-(trifluoromethyl)benzamide (43 mg, 0.15 mmol) were dissolved in butanol (2 ml), heated to 95° C., and HCl (20 µl) was added. Reaction was allowed to proceed overnight, and cooled to –20° C. for 2 h. Precipitated was filtered and washed with cold butanol (3 ml) and cold ether (5 ml). Crude solid was purified by HPLC (10-65% ACN/$H_2O$) to give 31.5 mg (40%) of a white solid. LCMS (RT=1.26): 521.3 (100%), 522.4 (28%), 523.4 (4%). NMR, $^1H$, DMSO (400 MHz): 10.34 (s, 1H), 9.43 (s, 1H), 9.08 (s, 1H), 8.25 (s, 1H), 8.23 (d, 1H), 8.19 (s, 1H), 7.92 (d, 1H), 7.75 (t, 1H), 7.72 (s, 1H), 7.69 (s, 1H), 7.64-7.59 (m, 2H), 6.29 (s, 1H), 6.15 (s, 1H), 2.95 (quin, 1H), 2.17 (s, 3H), 2.00-1.91 (m, 2H), 1.70-1.51 (m, 6H).

CD532 (Large Scale)

3-(4-aminophenyl)-1-[3-(trifluoromethyl)phenyl]urea (JM149). P-phenylenediamine (4.33 g, 40 mmol) was dissolved in 100 ml CH2Cl2 in a dried, argon-charged round-bottom flask with stirbar. Mixture was cooled to 0° C. before dropwise addition of 3-(trifluoromethyl)phenyl isocyanate (5.64 ml, 40 mmol). Reaction was allowed to warm to ambient temperature over 3 hours, and precipitate was filtered and washed with cold CH2Cl2 (50 ml) to yield a white solid. LCMS (RT=1.10): 295.2 (100%), 296.2 (30%), 297.3 (5%). 1-(4-((4-((5-cyclopentyl-1H-pyrazol-3-yl) amino)pyrimidin-2-yl)amino)phenyl)-3-(3-(trifluoromethyl)phenyl)urea (CD532) 2-chloro-N-(5-cyclopentyl-1H-pyrazol-3-yl)pyrimidin-4-amine (JM5; 1.98 g, 1 mmol) and JM149 (2.21 g, 1 mmol) were dissolved in BuOH 40 ml and stirred at 85° C. before dropwise addition of HCl (120 µl). Product formed immediately, and reaction was cooled to ambient temperature and filtered to yield 3.4 g (6.51 mmol, 87%) of a light purple solid. 0.51 g of crude product was purified by HPLC to yield 332 mg of a white solid (65.2% recovery). LCMS (RT=1.32): 522.2 (100%); 523.3 (28%); 524.4 (4%). NMR, 1H, DMSO (400 MHz): 9.69 (s, 1H), 9.51 (s, 1H), 9.29 (s, 1H), 8.94 (s, 1H), 8.25 (s, 1H), 8.04 (s, 1H), 7.91 (d, 1H), 7.65-7.51 (m, 3H), 7.45 (quin, 1H), 7.40-7.32 (m, 2H), 7.23 (d, 1H), 6.32 (s, 1H), 6.19 (s, 1H), 2.93 (quin, 1H), 2.06-1.39 (m, 8H).

Expression and Purification of Aurora A Kinase

Purification and expression of Aurora A was performed as described previously (Martin et al., 2012), with the following modifications. Aurora A (residues 123-390, T287D) was cloned into a pET28a plasmid providing fusion with a PreScission Protease-cleavable hexahistidine tag. The protein was overexpressed in BL-21(DE3) cells at 18° C. Digestion with PreScission protease was performed overnight at 4° C. in a 10 kD MWCO dialysis cartridge (Thermo Scientific, Inc) with dialysis buffer containing 50 mM MES (pH 6.5), 300 mM NaCl, and 1 mM DTT, followed by 4 hours of dialysis with buffer containing 50 mM MES (pH 6.5) and 1 mM DTT before loading onto ion exchange column. Pooled fractions were concentrated to 5 mg/mL (Amicon Ultra 10 kD MWCO, Millipore) and loaded onto a HiLoad Prep Grade Superdex 200 column (GE Healthcare) equilibrated with 50 mM HEPES (pH 7.4) and 1 mM DTT to yield monomeric enzyme for use in both kinase assays and crystallization.

Gene Set Enrichment Analysis (GSEA)

Normalized gene expression (Affymetrix HT-HGU133A) was downloaded from the Genomics of Drug Sensitivity in Cancer website and log-transformed. 87 cell lines had both unambiguous EC50 (calculated using four-parameter non-linear regression within GraphPad Prism) and gene expression data.

GSEA software (Subramanian et al., 2005) was used to identify groups of functionally related genes correlated with sensitivity to CD-532. GSEA was run on these 87 cell lines using the collections of 4,722 curated gene sets (C2) and 615 transcription factor targets (C3) from MSigDB (v4.0). Using the individual EC50 of each cell line as a continuous phenotype, genes were ranked using Pearson's correlation, and P values were calculated using 1,000 gene set permutations. Gene sets with less than 15 genes or more than 500 genes were excluded from the analysis. Gene sets with an FDR≤0.05 and a nominal P≤0.05 were considered significant.

Cell-line status for MYCN amplification and drug sensitivity data for VX-680 were downloaded from the Genomics of Drug Sensitivity in Cancer website. Cell-line sensitivity to JQ1 has been previously published (Puissant et al., 2013). Amplified cells possessed MYCN copy number ≥8. The significance of sensitivity of CD-532 (EC50 calculated using the four-parameter log-logistic function in R using the "drc" package), JQ1, and VX-680 in relation to MYCN amplification status was assessed using the Wilcoxon Rank Sum test in R.

In Vivo Studies

CD532 was formulated at 20 mg/ml in 7.5% DMSO and 92.5% PEG300. LC-MS/MS detection of CD532 for pharmacokinetic studies was performed using a Waters 2545 binary gradient module, Waters 2767 sample manager, and Waters 2998 photodiode array detector running MassLynx v4.1. Mice were injected intraperitoneally as described. For determining tumor volume, for example in medulloblastoma model mice, mice were euthanized once maximum tumor length exceeded 2.0 cm, per IACUC protocol (IACUC, Institutional Animal Care and Use Committee).

In Vitro Kinase Assays

Kinase assays for Aurora A were performed in 10 mM HEPES pH 7.5, 10 mM $MgCl_2$, 0.01% Triton, 4% v/v DMSO, 5 nM kinase, and either 4 μM histone H3 or 30 μM synthetic peptide AKRRRLSSLRA (Elim Biopharmaceuticals, Inc). Drug concentration ranged from 2000-5 nM. Reactions were preincubated with inhibitor for ten minutes before initiation by addition of 100 μM nonradioactive ATP supplemented with $^{32}P$ ATP (1 mCi in 200 μL, Perkin-Elmer, 0.8 μCi per reaction). Reactions were quenched at 10 min by spotting 3 μL quantity onto P81 phosphocellulose (Whatman), which were washed 5×5' in 0.1% phosphoric acid and dried. Radioactivity was measured by phosphorimaging and recorded on a Typhoon fluorescence imager (Molecular Dynamics). Data were quantified using Spot (Knight et al., 2007) and fit to a sigmoidal dose-response curve using Prism software (GraphPad Software, Inc) to obtain $IC_{50}$ values.

Crystallization and Data Collection

After gel separation, purified fractions of Aurora A were pooled and concentrated in the presence of drug to a final concentration of 20 mg/ml Aurora A and 1 mM drug. All crystallization reagents were obtained from Hampton Research (Aliso Viejo, Calif.). Crystals were generated by hanging drop vapor diffusion at room temperature using a 1:1 mixture of protein solution and well solution. For Aurora A apo, well solution consisted of 10% Tacsimate (pH 7.0) and 20% PEG 3350. For Aurora A with CD532, well solution consisted of 0.2 M magnesium acetate tetrahydrate, 0.1 M sodium cacodylate trihydrate and 20% w/v PEG8000 at pH 6.0. Crystals did not grow in the Apo conditions in the presence of drug, or in the drug conditions in the absence of compound. CD532-bound and apo crystals were cryoprotected with well solution supplemented with 10% and 25% ethylene glycol, respectively, and stored in liquid nitrogen. Diffraction data were recorded on Beamline 8.2.2 at the Lawrence-Berkeley Advanced Light Source at a temperature of 100 K and wavelength of 1.0088 nm. Data were indexed using HKL2000 (HKL Research, Inc). The drug-bound crystals belong to the $C222_1$ space group with one monomer in the asymmetric unit, and apo crystals belong to the $P3_1$ space group with four monomers in the asymmetric unit. Molecular replacement and refinement were performed using Phaser-MR and phenix.refine in PHENIX (Adams et al., 2010), model building was performed using Coot (Emsley et al., 2010), and figures were drawn using MacPYMOL 1.5.0 (Schrodinger, LLC). Data and refinement statistics are shown in Table 1. Atomic coordinates and structure factors for CD532-bound and Apo Aurora A have been deposited in the PDB as 4J8M and 4J8N, respectively.

Initial Screen for Conformation-Disrupting Aurora A Inhibitors

To construct a diverse panel of potential Aurora A inhibitors that might disrupt the native conformation of Aurora A, the panel was started with both diaminopyrimidine (VX-680-like) and pyrazolopyrimidine (PP-1-like) scaffolds (FIG. 1A) respectively). Derivatives of each of these scaffolds were known to bind to Aurora Kinase A, structural data were available on both scaffolds bound to related kinases, and routes to their synthesis were tractable. To these scaffolds were fused biphenyl urea and amide moieties which were predicted, based on published structures, to stabilize distinct conformations of Aurora A, including those that might lead to MYCN instability (Dietrich et al., 2010; Filomia et al., 2010).

Figure 1B:
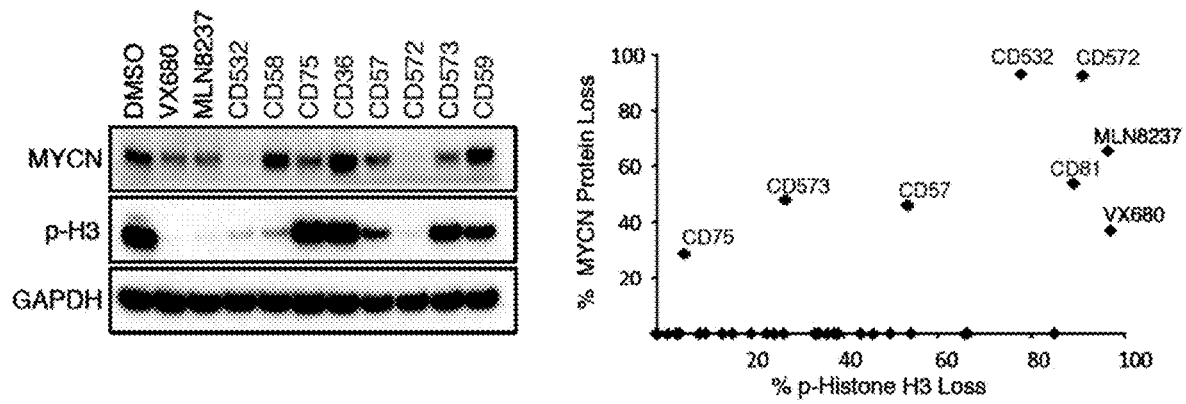
Figure 1C:
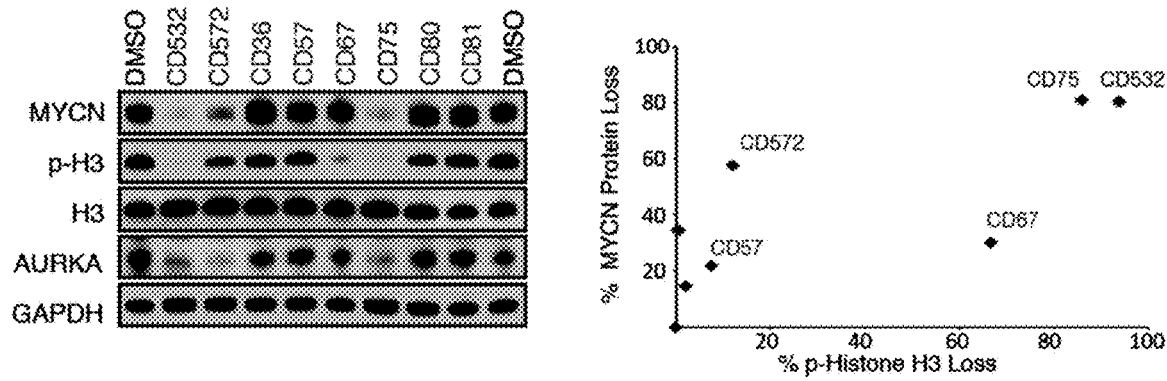

To test whether this panel of 32 putative conformation-disrupting Aurora A inhibitors would destabilize MYCN, initially Kelly MYCN-amplified neuroblastoma cells were treated with candidate inhibitors and MYCN protein was measured by western blot. Phosphorylation of Histone H3, a known substrate for Aurora A and B and a marker for mitosis, was also assessed. FIGS. 1B and 5 show decreased levels of both MYCN protein and p-Histone H3 in response to several members of the screening panel (quantitated in FIG. 1B). CD532 and CD572 treatment decreased levels of both MYCN and p-Histone H3 proteins (FIG. 1B). In contrast, and as predicted, known inhibitors of Aurora A, VX-680 and MLN8237, blocked Histone H3 phosphorylation at 1 μM yet demonstrated much more modest effects on levels of MYCN protein. Candidate CDs were subsequently screened against a second MYCN-amplified neuroblastoma cell line, SK-N-BE(2) (FIG. 1C), substantiating CD532 as the most active lead compound.

Figure 1D:
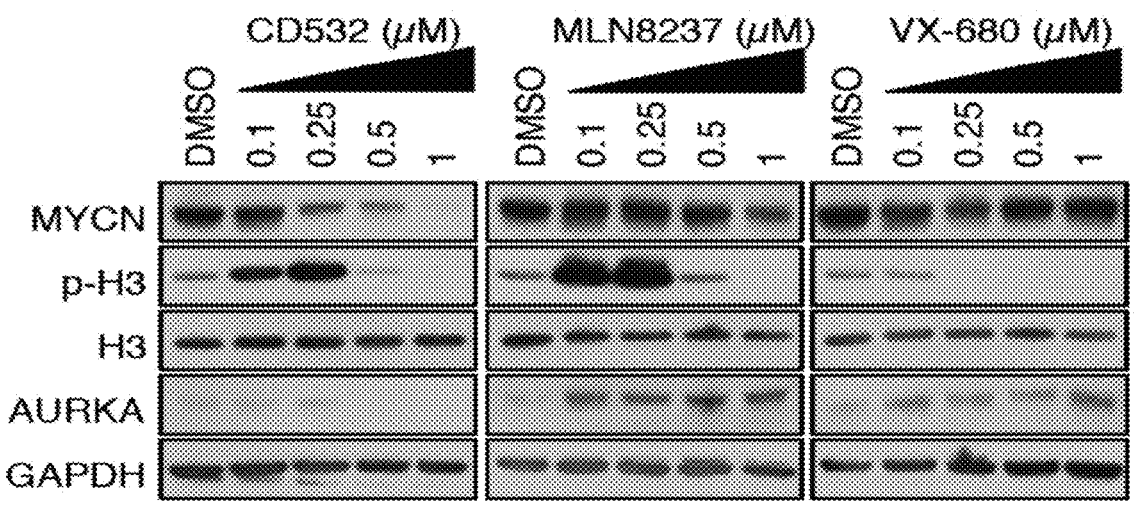
Figure 7A:
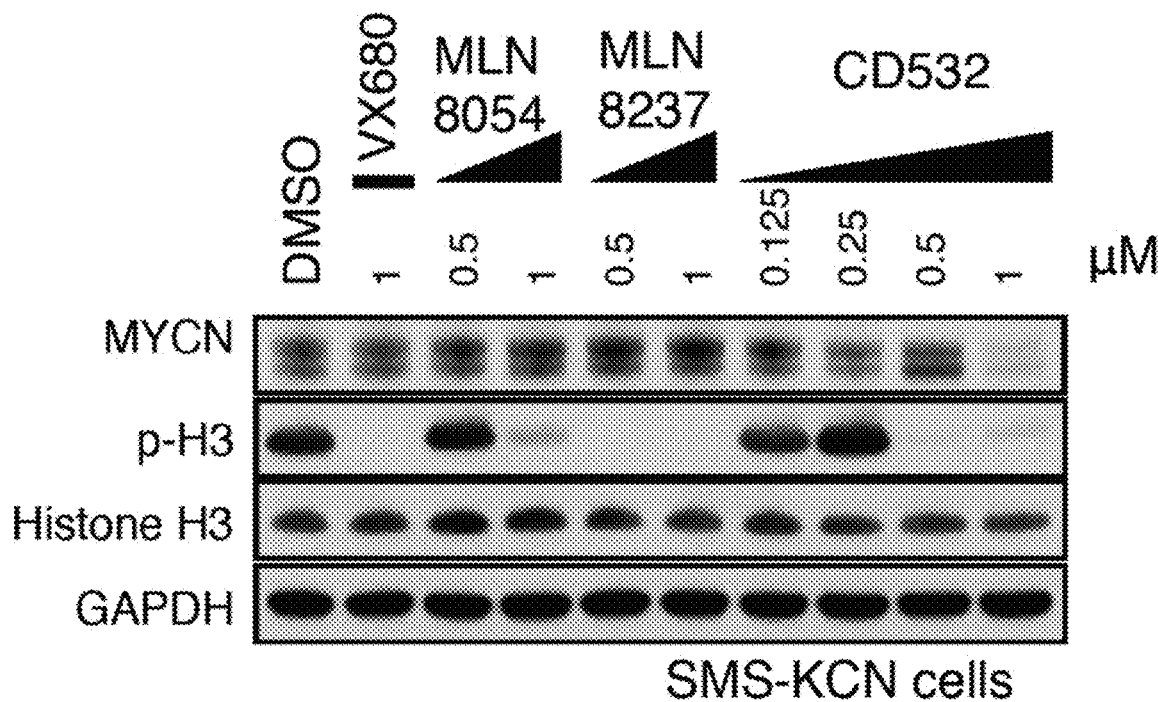
FIGS. 7A-B. Dose response of CD532 in other MYCN amplified neuroblastoma cell lines.
Figure 7B:
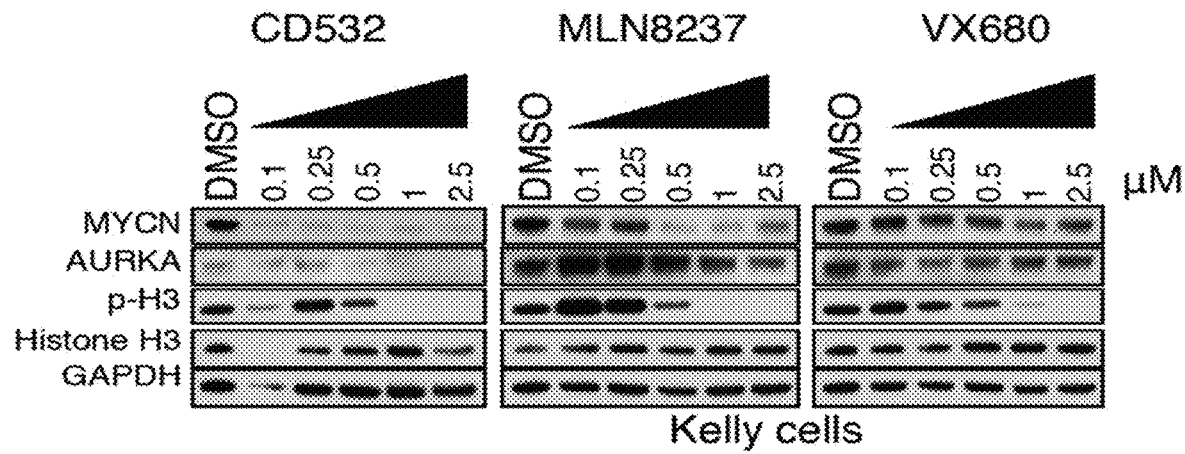
Figure 8:
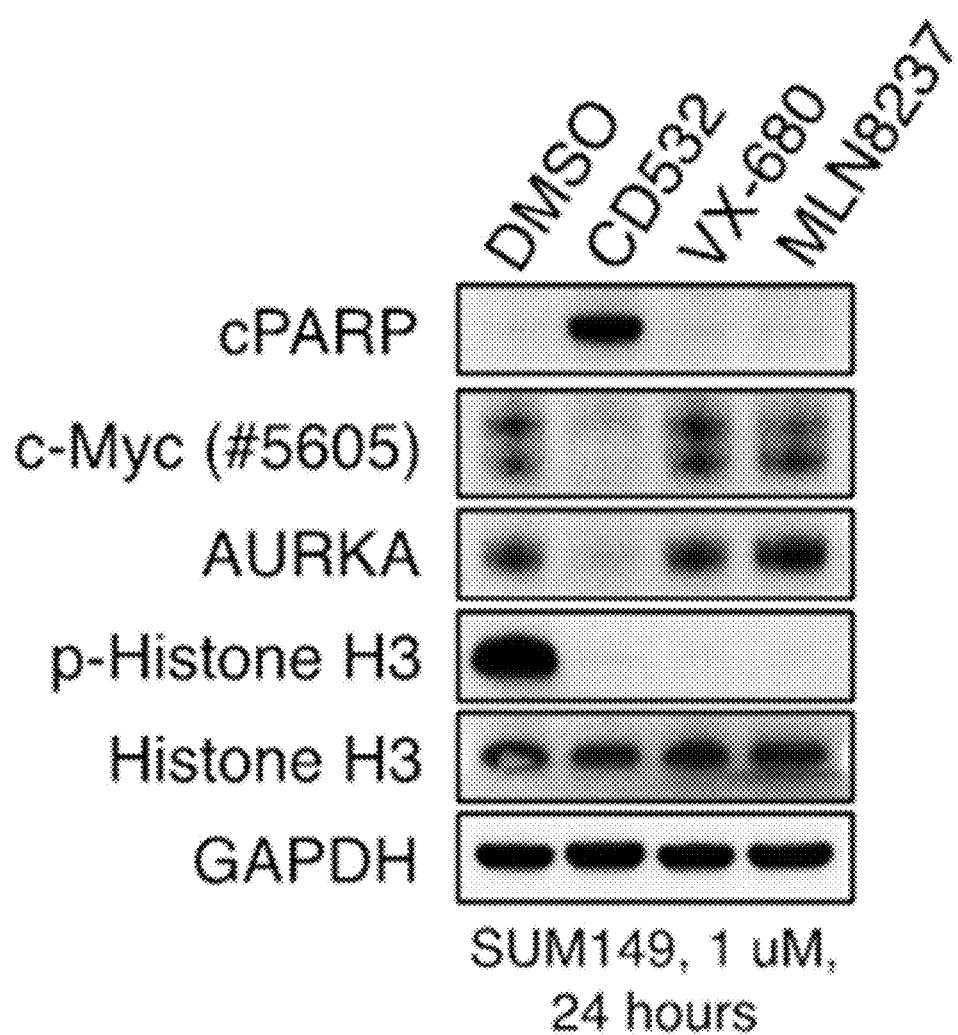
FIG. 8. CD532 and related compounds are also effective against c-Myc: The MYCN-related protooncogene MYC is prevalent in many cancer types, including breast cancer; Treatment of the c-Myc-expressing breast cancer cell line SUM149 (ER-/PR-) demonstrated loss of c-Myc, similar to what we observe in MYCN-expressing cell lines.
Figure 9:
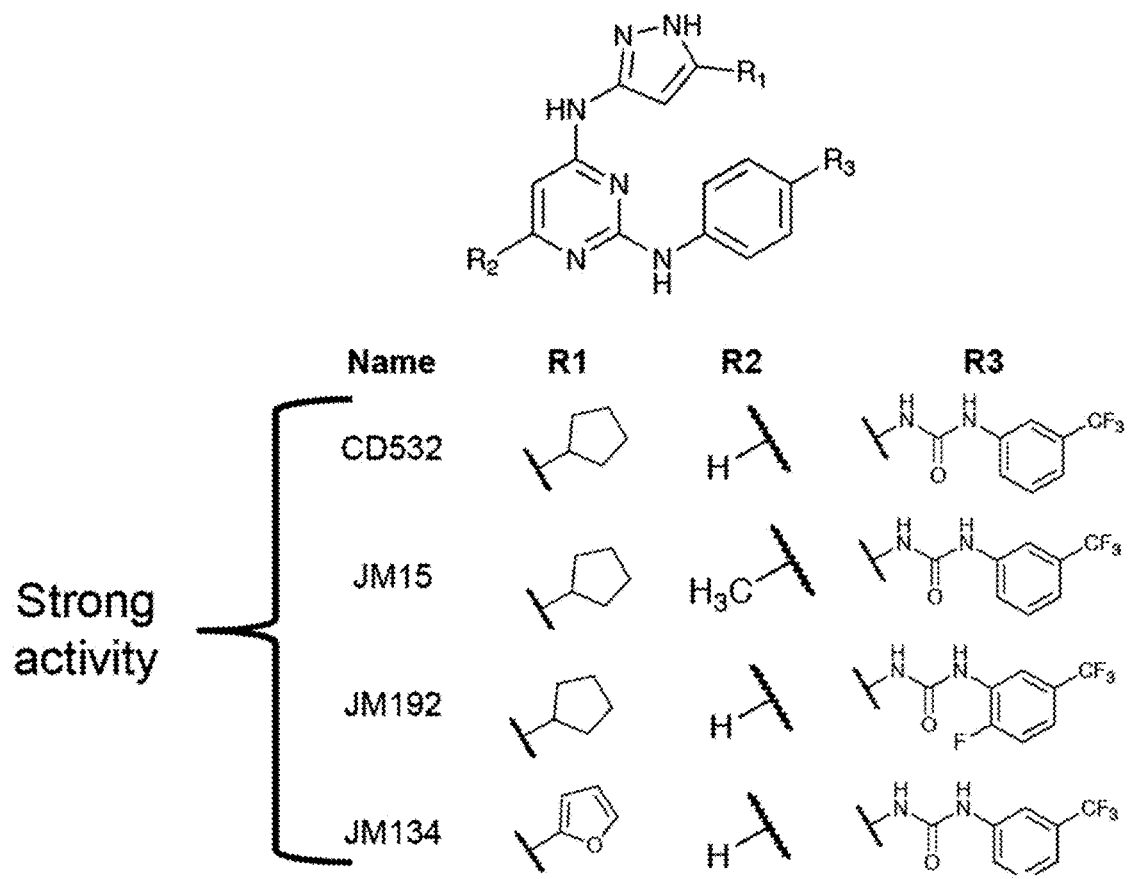
FIG. 9. List of compounds generated and biochemical activity against MYCN protein levels.
Figure 9:
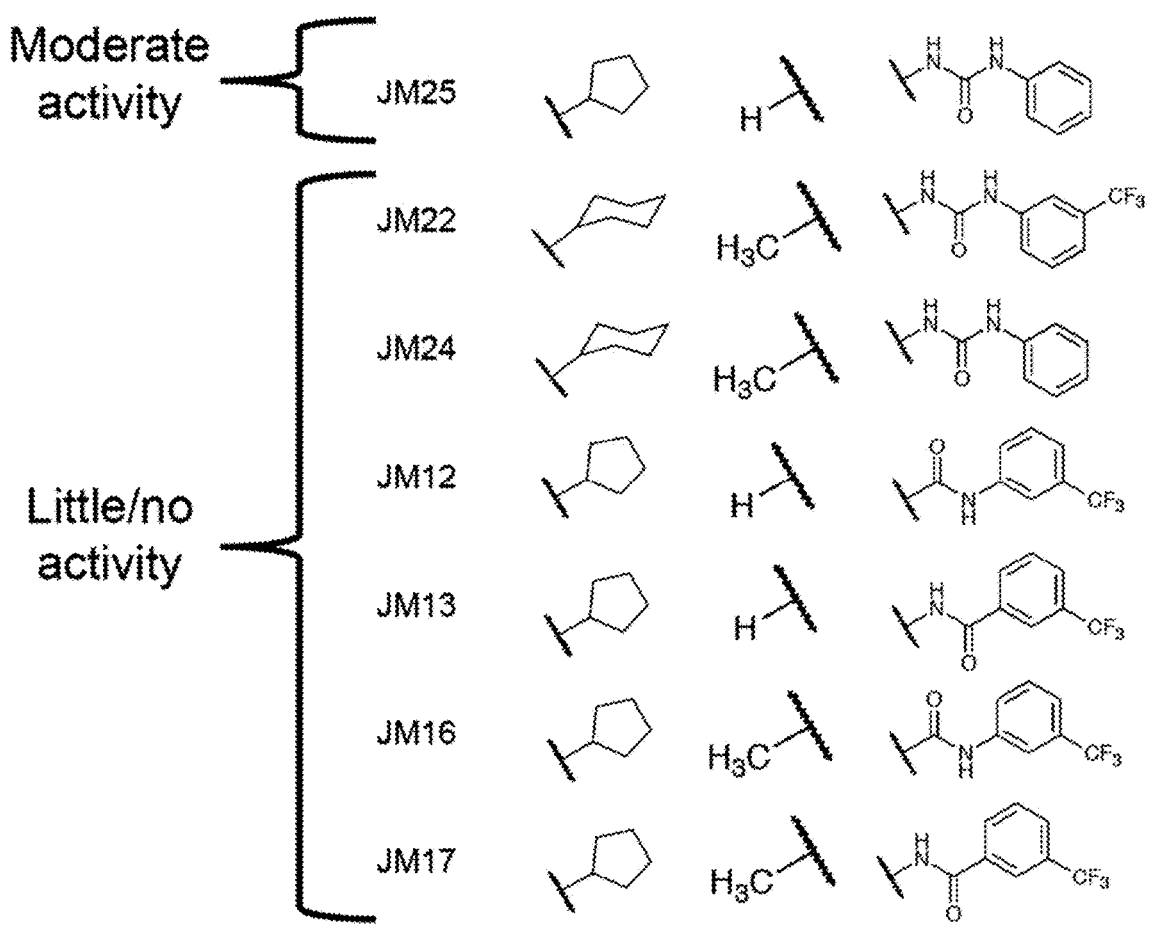
Figure 10A:
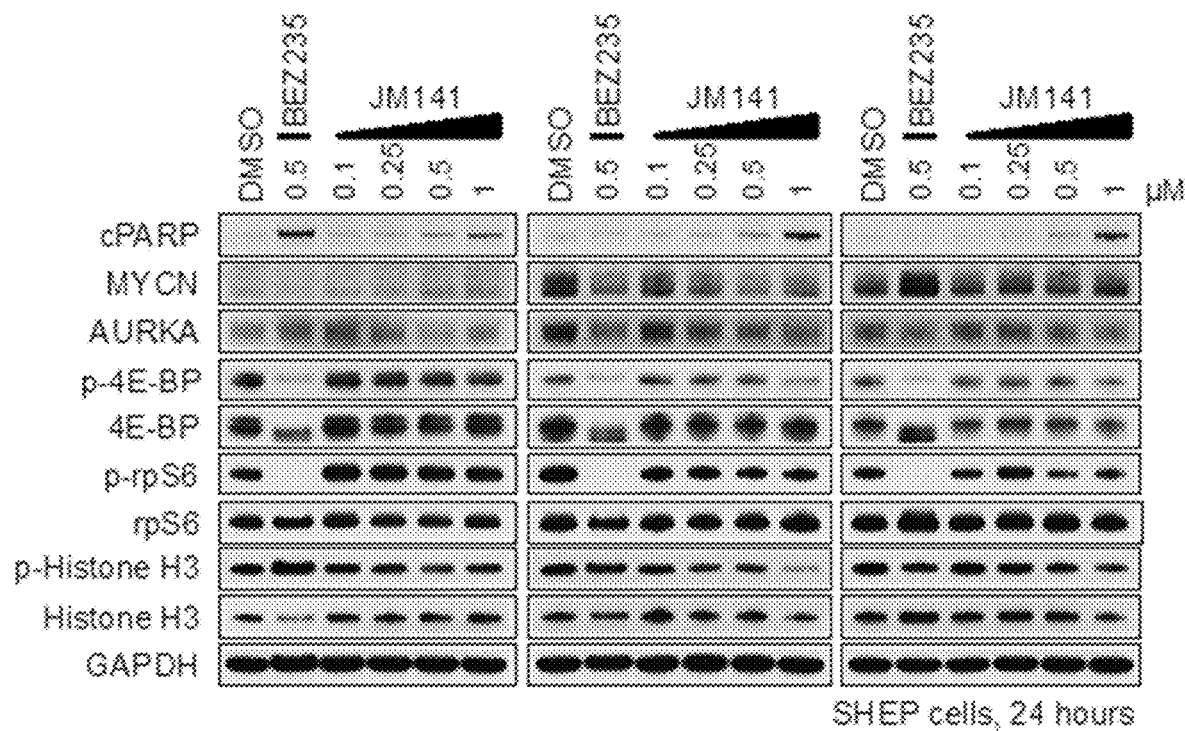
FIGS. 10A-C. Functional data for compounds (FIG. 10A) JM141 causes dose-dependent loss of MYCN that requires MYCN phosphorylation, and does not act through the PI3K/mTOR pathway: Immunoblot: Dose-dependent loss of MYCN and cytotoxicity in MYCN-expressing SHEP cells (middle panel), but not in SHEP cells without MYCN (left) or with degradation-resistant $MYCN^{T58A}$ (right); Graph: Quantification of MYCN protein demonstrating that degradation-resistant $MYCN^{T58A}$ protects against JM141-induced loss of MYCN.
Figure 10B:
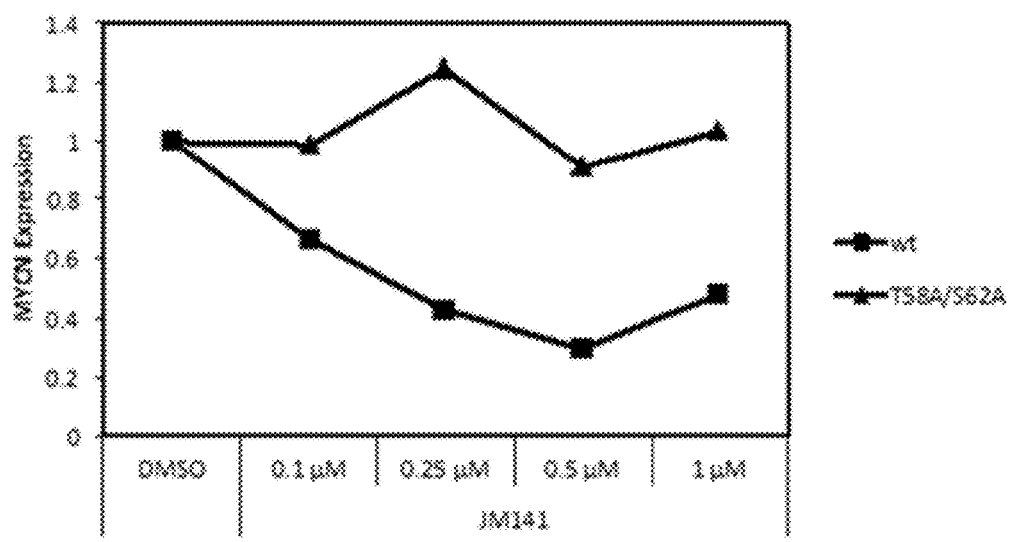
Figure 10C:
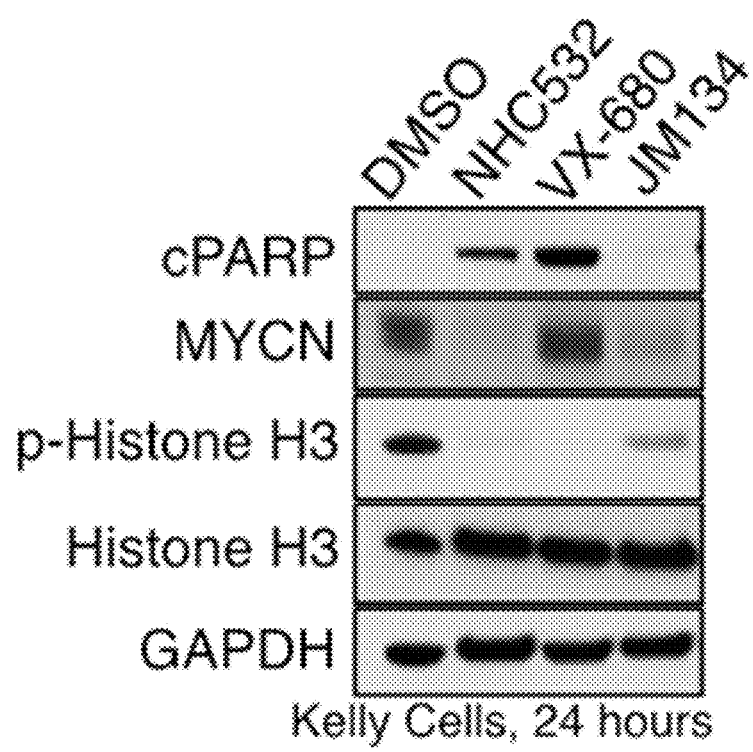

CD532 Potently Inhibits Aurora A, Causes Loss of MYCN, and is Cytotoxic in MYCN-Amplified Neuroblastoma Cells To determine the biochemical potency of CD532 dose response against purified Aurora A protein were measured, revealing potent Aurora Kinase A inhibition, with an $IC_{50}$ of 45 nM. Similar dose response curves with VX-680 and MLN8237 were consistent with published in vitro $IC_{50}$ values (FIG. 6A). Treatment of multiple cell lines with CD532, MLN8237, and VX-680 showed dose dependent loss of MYCN protein with CD532, and little or no response to high concentrations of MLN8237 (FIGS. 1D and 7A-B).

MLN8237 is a relatively selective inhibitor of Aurora A with $IC_{50}$ values of 1.2 nM and 396.5 nM for Aurora A and B respectively, while VX-680 is potent against both Aurora A and Aurora B, with IC50s of 0.6 nM and 18 nM respectively (Harrington et al., 2004; Lin et al., 2012; Manfredi et al., 2011; Nie et al., 2012; Otto et al., 2009). Notably, the in vitro (cell line) activity of CD532 against MYCN paralleled its cell-free in vitro IC50 for Aurora A by approximately 10 fold (FIGS. 1D and 7). By contrast MLN8237 and VX-680 treatment effected little loss of MYCN protein even at doses 100 to 1000 times greater than their $IC_{50}$ values for Aurora A. MLN8237 and VX-680 upregulated or had little effect on Aurora A protein. CD532, in contrast, downregulated Aurora A protein across cell lines (at higher concentrations) consistent with distinct mechanisms of binding underlying these differential effects (FIGS. 1D and 7). At low concentrations of CD532 and short time points however, loss of MYCN was apparent while levels of Aurora A protein were unaffected (FIGS. 1D, 7, and 12). These observations are consistent with degradation of MYCN resulting from CD532 binding, rather than from loss of Aurora A protein.

Histone H3 is a known substrate for both Aurora A and B. Accordingly, dual inhibition of Aurora AB with VX-680 abrogates phosphorylation of Histone H3 at S10. In contrast, MLN8237 caused an initial increase in S10 phosphorylation at lower concentrations, followed by a sharp drop at higher concentrations (FIGS. 1D and 7). This increase in phosphorylation of Histone H3 in response to MLN8237 has been described previously, and results from Aurora A inhibition with feedback increase in Aurora B activity (Crosio et al., 2002; Delmore et al., 2011; Filippakopoulos et al., 2010; Görgün et al., 2010; Liu et al., 2004; Mertz et al., 2011; Ouchi, 2004; Scrittori et al., 2001; Wen et al., 2012). CD532 behaves similarly to MLN8237 with regard to Histone H3 phosphorylation, consistent with an Aurora A-specific effect.

Figure 1E:
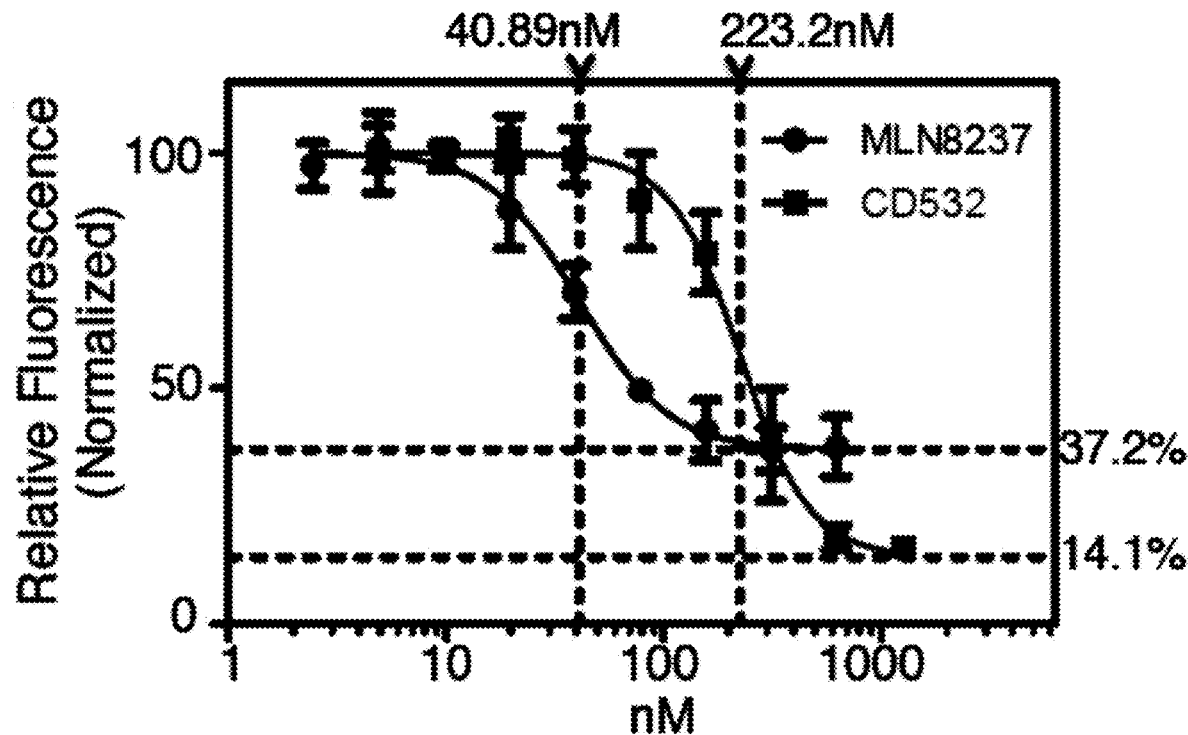
Figure 1F:
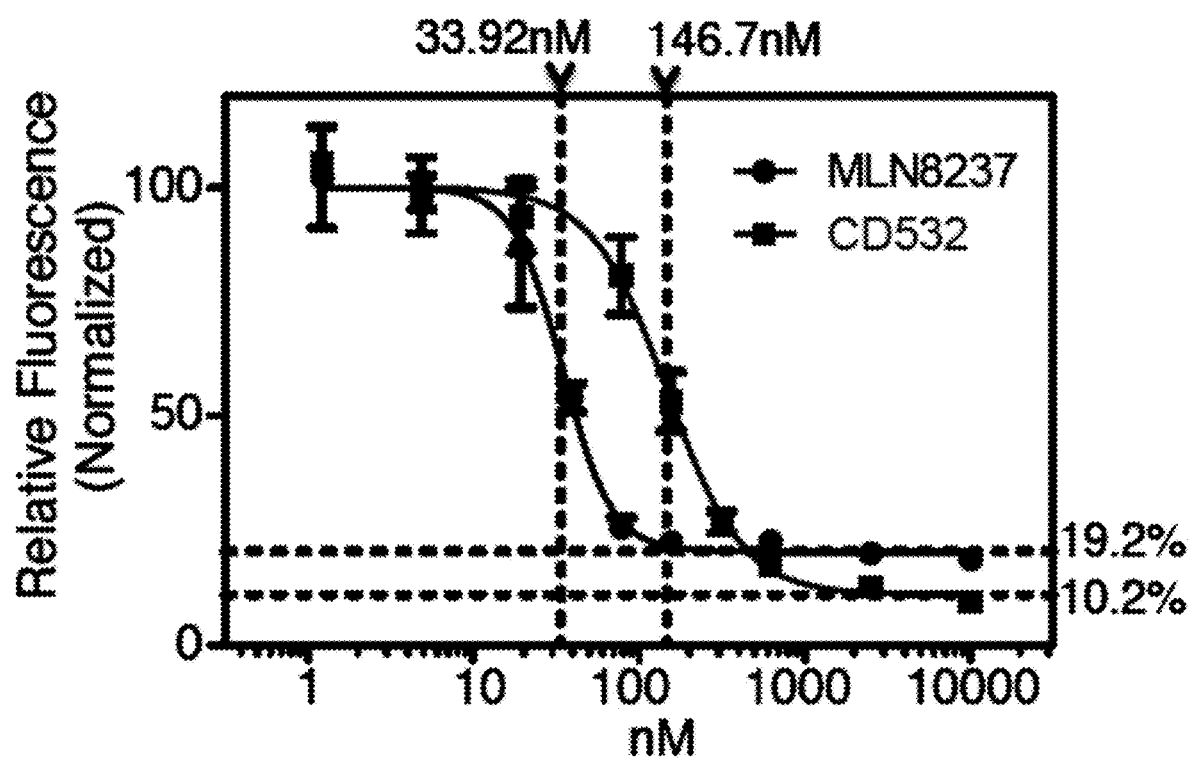

The cellular $EC_{50}$ at 72 hrs against two different MYCN-amplified neuroblastoma cell lines for both CD532 (223.2 nM and 146.7 nM) and MLN8237 (40.89 nM and 33.92 nM) was measured. These values are directly proportionate to the cell-free IC50 for Aurora A inhibition by CD532 (45 nM) and MLN8237 (4 nM) by ~10 fold (FIGS. 1E and F). Additionally, the $IC_{50}$ of CD532 for on-target MYCN knockdown in SK-N-BE(2) cells (~250 nM—FIG. 1D) is consistent with the cellular $EC_{50}$ (223.2 nM—FIG. 1E). Notably the maximal cytotoxicity ($E_{max}$) for each compound is proportionate to the degree of MYCN knockdown (and not to the degree of Aurora A inhibition) in MYCN-amplified neuroblastoma lines. These data argue for an Aurora A-dependent effect on inhibition of cell growth, and a MYCN-dependent effect on loss of viability.

Figure 12A:
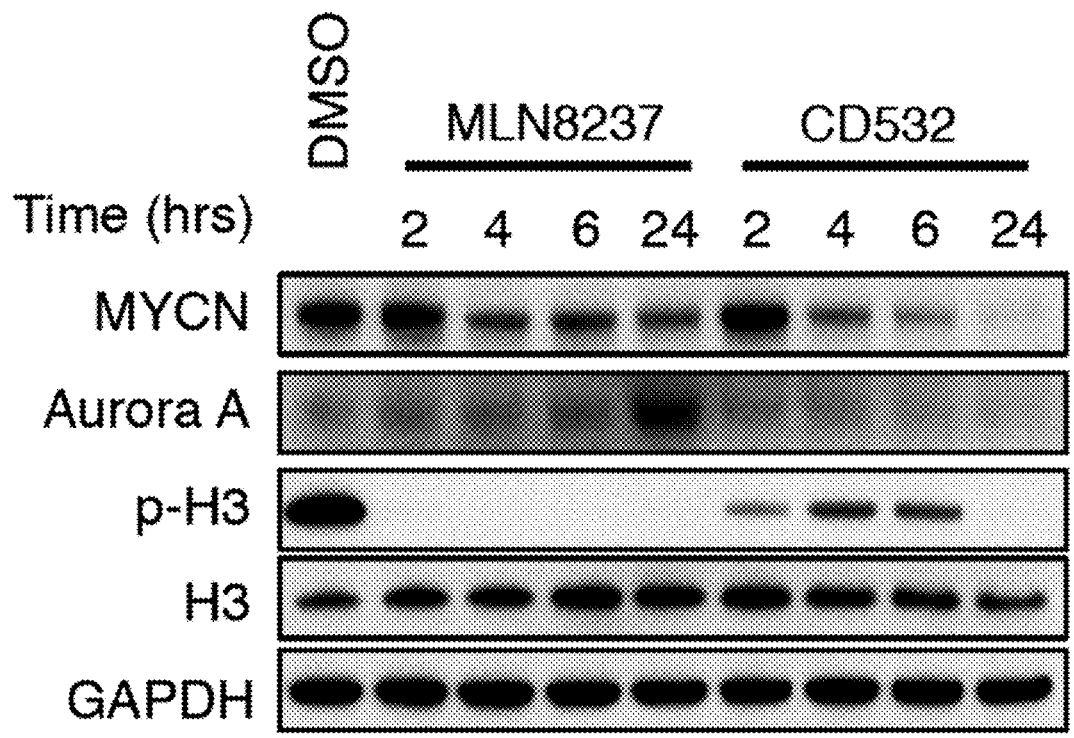
Figure 12B:
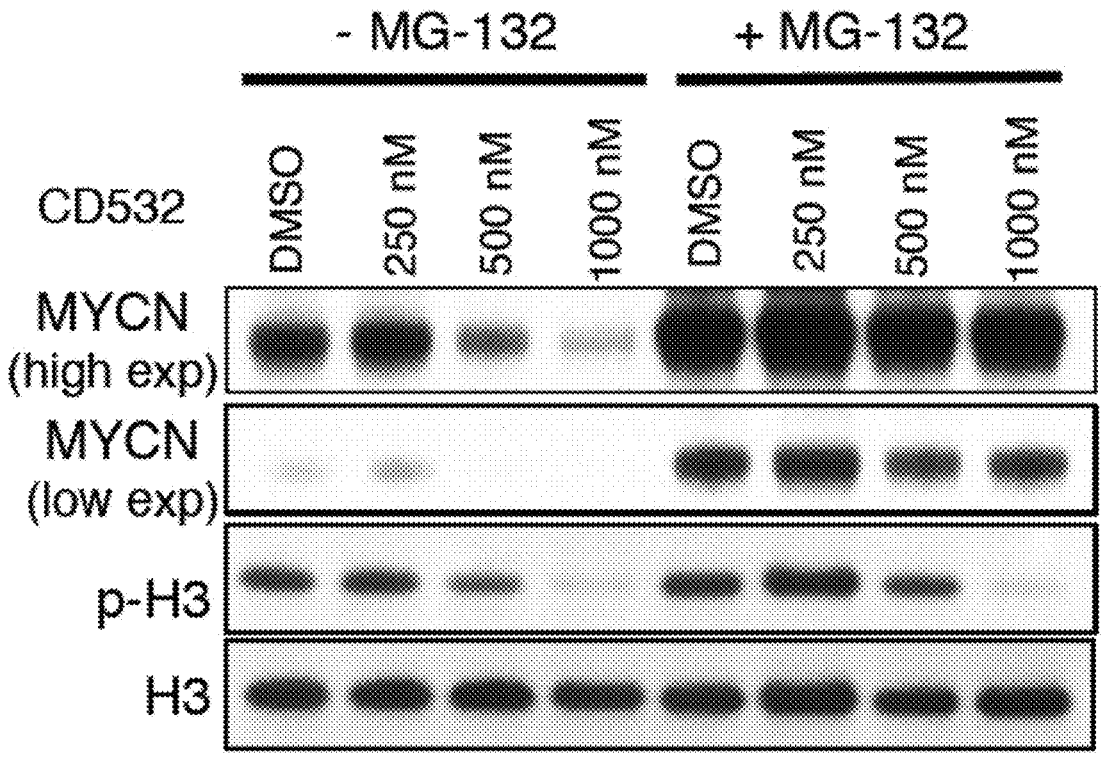

Degradation of MYCN Requires Phosphorylation and Proteasomal Degradation of MYCN The loss of Aurora A scaffolding function by siRNA knockdown, causes MYCN degradation through canonical ubiquitination and proteasomal degradation (Harrington et al., 2004; Manfredi et al., 2011; Otto et al., 2009; Prochownik and Vogt, 2010). As such, the expected rapid degradation of MYCN protein occurs within hours of dissociation of the MYCN-Aurora A complex. In fact, a clear and time-dependent loss of MYCN protein was observed at time points as short as 4 hrs of treatment with CD532 (FIG. 12A). In contrast, treatment with MLN8237 results in similarly rapid, but much more modest decrease in levels of MYCN protein that does not change over time (FIG. 12A). MYCN-amplified SK-N-BE(2) and IMR32 cells were also treated with increasing concentrations of CD532 in the presence of the proteasome inhibitor MG-132. While MG-132 had no effect on inhibition of H3 phosphorylation in response to CD532, proteasomal inhibition protected MYCN from degradation in response to CD532 (FIG. 12B).

MYCN is believed to be sequentially phosphorylated at S62/T58 before it is targeted for degradation by ubiquitination, and only phosphorylated, ubiquitinated MYCN is protected from degradation by Aurora A (Gustafson and Weiss, 2010; Otto et al., 2009). To test whether the activity of CD532 is dependent on these phospho-residues, SHEP MYCN-non-amplified neuroblastoma cells, engineered to express either MYCNWT or a non-phosphorylatable mutant of MYCN (MYCNT58A/S62A) were treated with increasing concentrations of CD532. FIG. 12C shows a dose-dependent decrease in wild-type MYCN protein. In contrast, MYCNT58A/S62A was partially protected from degradation, suggesting that CD532 potentiates loss of MYCN through the canonical phosphorylation and ubiquitination pathway. Notably, even high concentrations of the conventional type I inhibitor VX-680, which stabilizes Aurora A in the active conformation (Otto et al., 2009; Zhao et al., 2008), had little effect on MYCN protein levels in this system (FIG. 12C).

Histone H3 is a known substrate for both Aurora A and B. Accordingly, dual inhibition of Aurora AB with VX-680 abrogates phosphorylation of Histone H3 at S10. In contrast, MLN8237 causes an initial increase in S10 phosphorylation at lower concentrations, followed by a sharp drop at higher concentrations (FIGS. 1D and 7A-B). This increase in phosphorylation of Histone H3 in response to MLN8237 has been described by others, and may result from Aurora A inhibition with feedback increase in Aurora B activity (Gorgun et al., 2010; Wen et al., 2012). CD532 behaves similarly to MLN8237 with regard to Histone H3 phosphorylation, consistent with an Aurora A-specific effect.

CD532 Stabilizes a DFG-in, Inactive Conformation of Aurora A

Figure 2A:
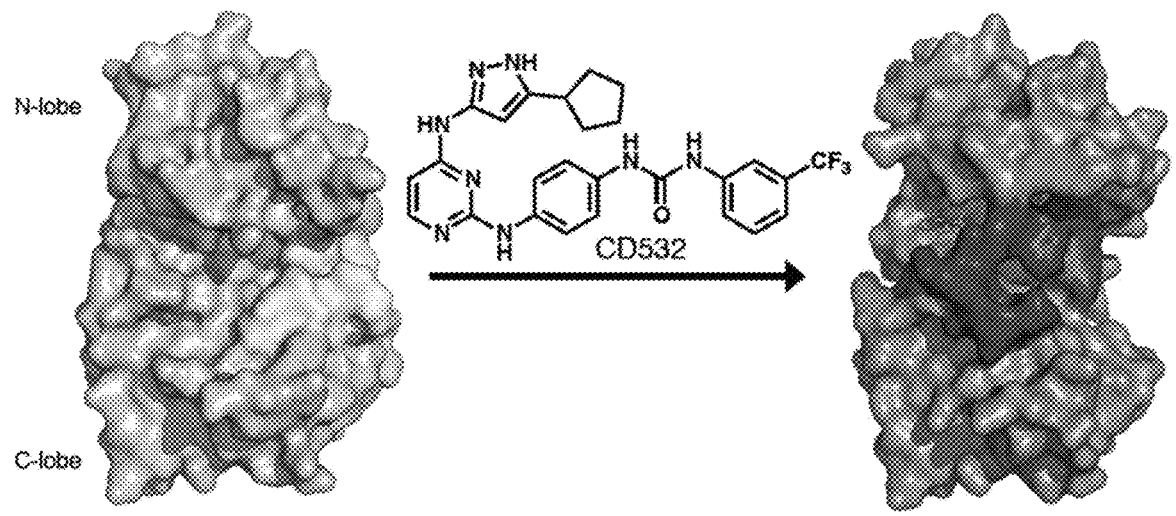
FIGS. 2A-G. CD532 stabilizes an inactive, DFG-in conformation of Aurora A.
Figure 2B:
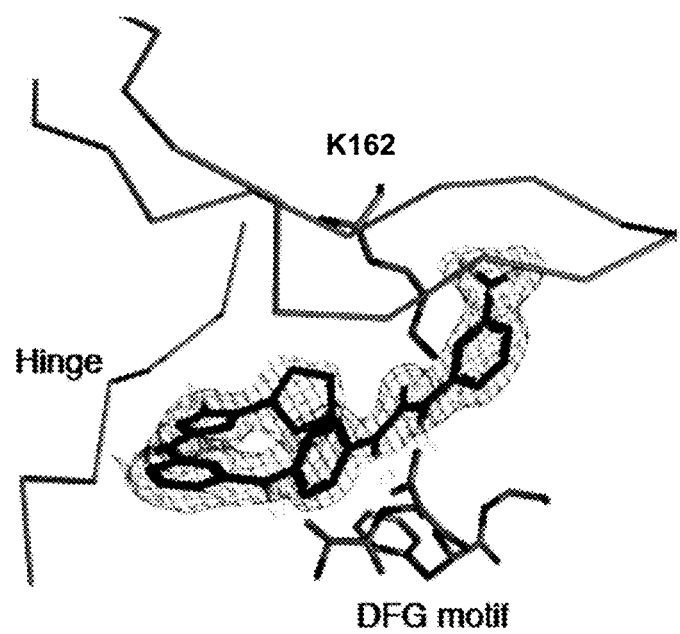
Figure 2C:
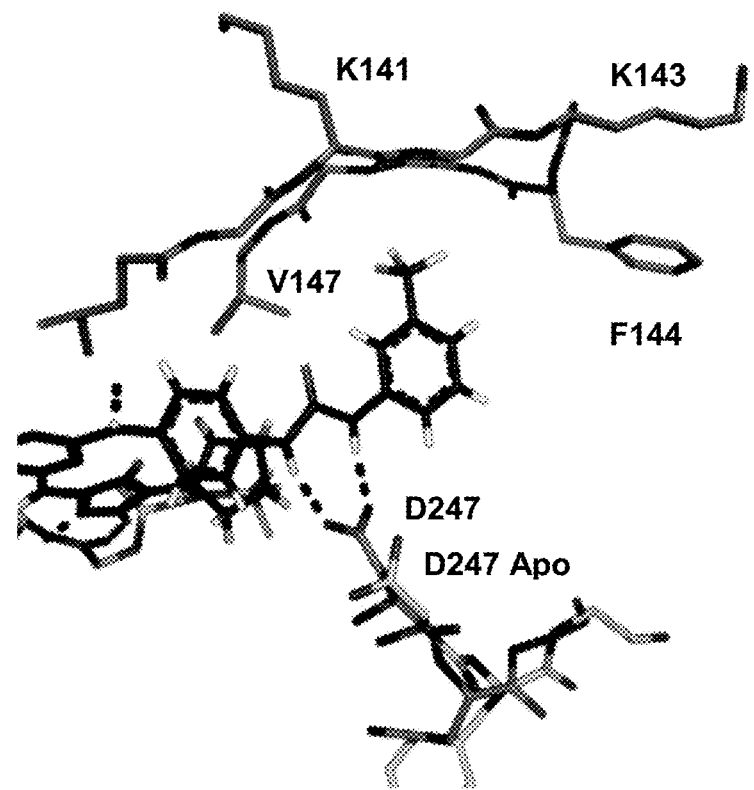
Figure 2D:
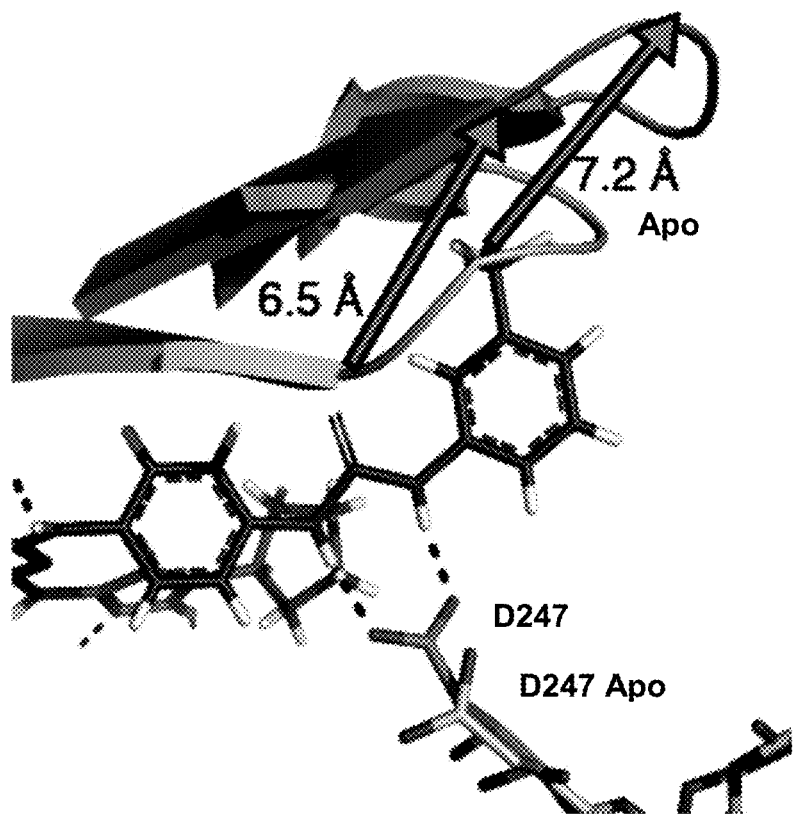
Figure 2E:
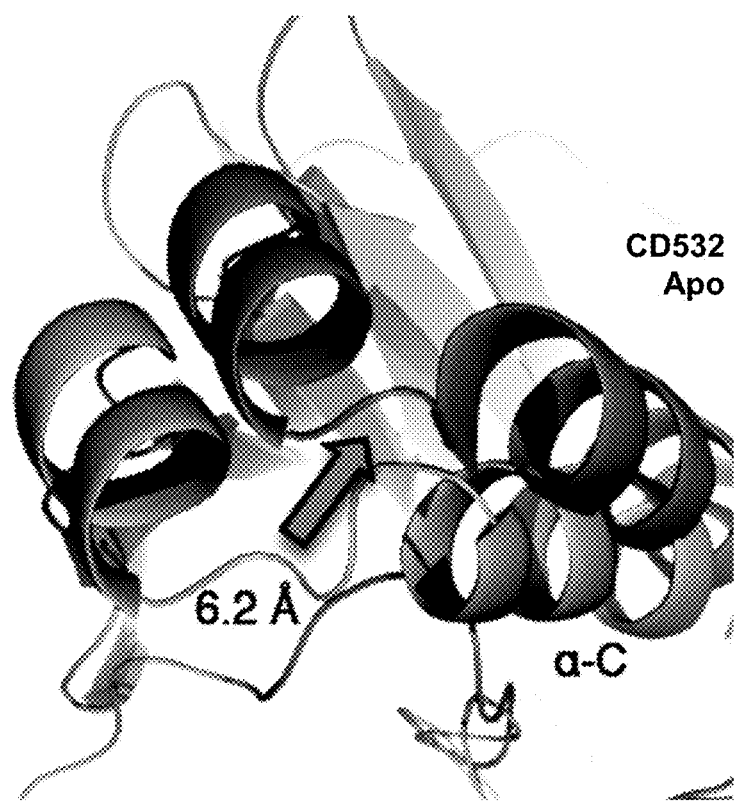
Figure 2F:
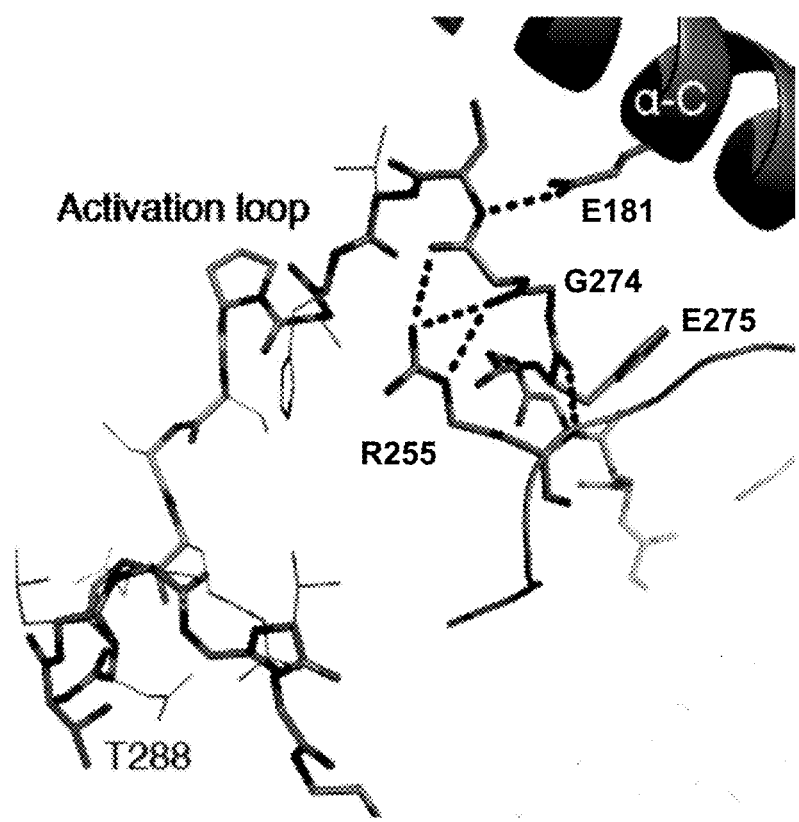
Figure 2G:
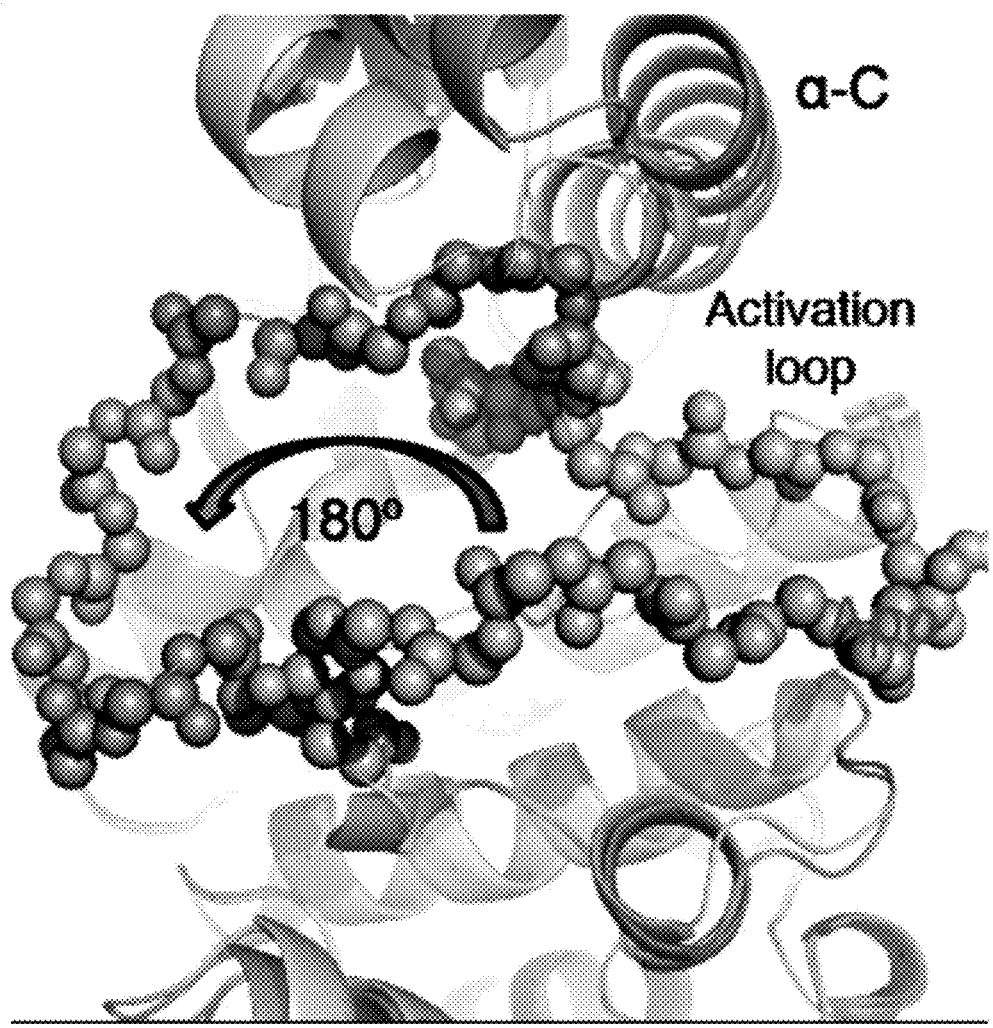
Figure 3A:
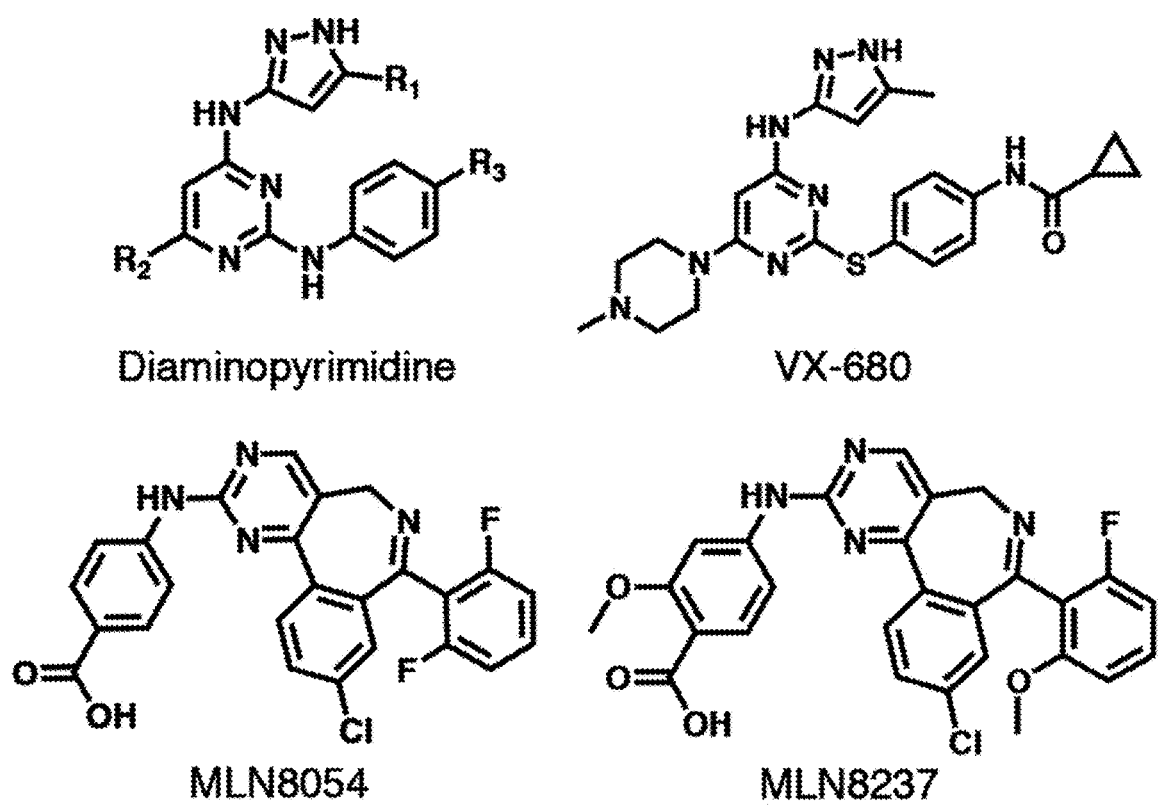
FIGS. 3A-D. Structure-activity relationships activity against Aurora A and loss of MYCN.
Figure 15A:
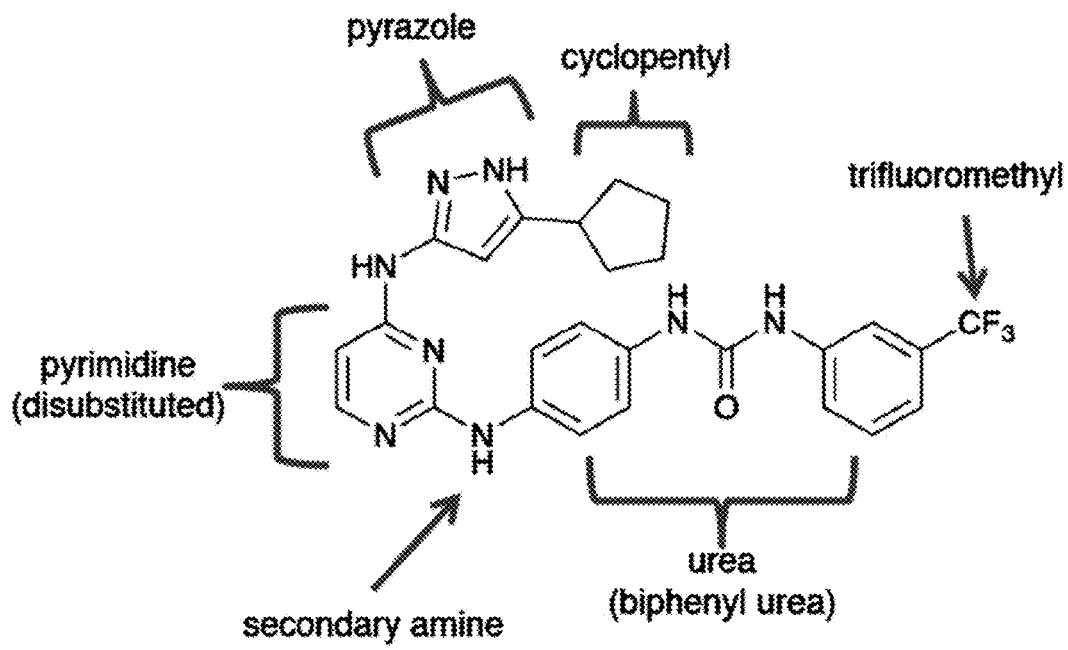
FIGS. 15A-B. Demonstration of structure-activity relationships of conformation disrupting Aurora inhibitors in Kelly neuroblastoma cells: Cells were treated with 1 uM of the indicated compounds for 24 hrs.
Figure 15B:
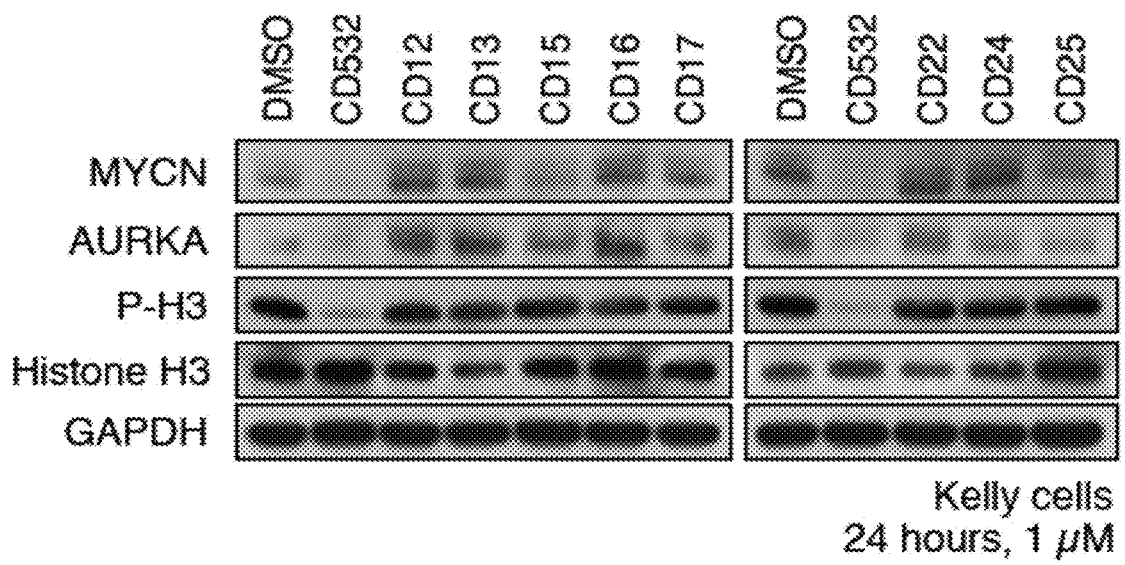

CD532 consists of an aminopyrazole-pyrimidine ATP-mimetic backbone, similar to VX-680, but includes a 3-trifluoromethyl-biphenyl urea as its conformation-disrupting pharmacophore (FIGS. 2 and 15). To determine how CD532 binding affects the conformation of Aurora A, we solved the crystal structure of the catalytic domain of Aurora A (residues 123-390) both alone (Apo) and bound to CD532, to resolutions of 3.14 Å and 1.85 Å, respectively (FIG. 3A, statistics in Table 1). This Apo structure is the first published structure of Aurora A without ligand. While the B-factor of the relatively disordered activation loop in both structures is high, the tracing of the polypeptide backbone was unambiguous. Electron density for CD532 within the active site was well defined (FIG. 2).

The ATP-binding hinge region of the Aurora A active site makes polar contacts with the aminopyrazole portion of CD532, consistent with a choice of ATP-mimetic scaffold. The catalytic residue D274 appears to have polar contacts with the urea moiety of CD532. This may stabilize the biphenyl urea in its orientation towards the N-terminal β1 and β2 strands forming part of the ATP binding pocket (FIG. 2B-C). The polar contacts between the urea moiety and CD532 allow for a ~7 Å displacement of the β1 and β2 strands in the N-terminal domain, via steric clash with the trifluoromethylphenyl moiety of CD532 (FIG. 2D). These β1 and β2 strands form part of a β-sheet that is the core of the relatively rigid N-terminal domain. Thus displacement of these strands by CD532 disrupts the conformation of Aurora Kinase A (Apo), rotating and shifting the N-terminal domain by 6.2 Angstroms, relative to the C-terminal domain (FIG. 2).

The highly conserved HRD sequence across many kinases is located at the lip of the active site. Coordination between this conserved HRD arginine and a phosphothreonine in the activation loop (R255 and T288 respectively, in the case of Aurora A) orients the HRD catalytic aspartic acid to be primed for catalysis. By this mechanism, the catalytic activity of HRD-containing kinases can be regulated through phosphorylation of their activation loop. In the presence of CD532, R255 and T288 of Aurora A are displaced by a considerable distance (FIG. 2F). CD532-bound Aurora sequesters R255 in a manner that displaces the catalytic HRD aspartic acid from its catalytically functional orientation, disengaging HRD regulation and stabilizing the kinase in a catalytically inactive conformation.

Indeed, the displaced α-C helix and R255 together trap the most N-terminal portion of the activation loop in a network of hydrogen bonds (FIG. 2F). This surprising interaction positions the activation loop backbone in a manner that stabilizes the entire activation loop in its inactive orientation, flipped 180° relative to its active state (FIG. 2G). Thus, CD532 stabilizes Aurora Kinase A in a novel conformation, associated with a 6.2 Å shift in the position of the N-terminal domain relative to the C-terminal domain, a disengaged state of the regulatory HRD motif, and a 180° flip in the activation loop.

Figure 3B:
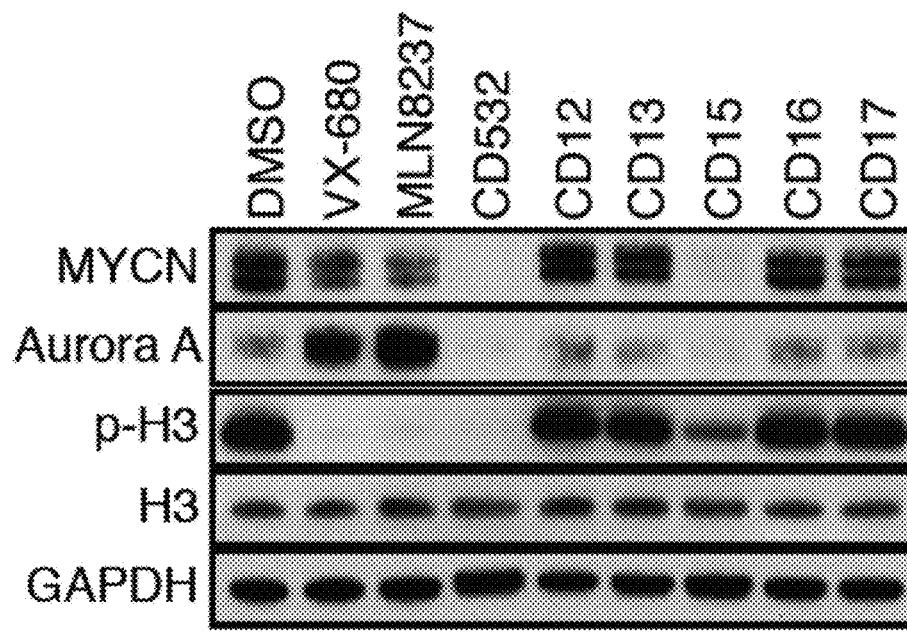
Figure 16:
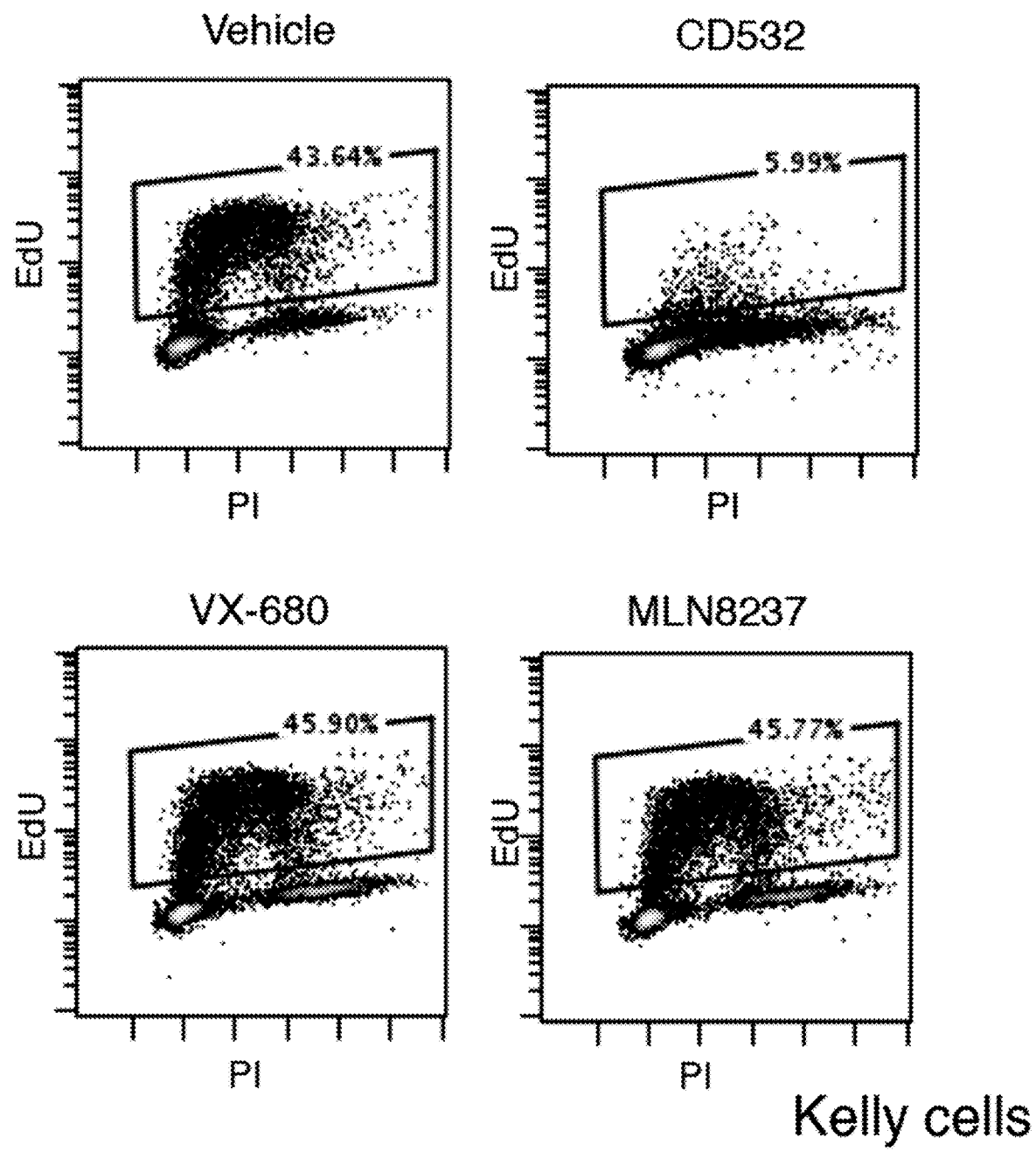
FIG. 16. Cell cycle analysis of MYCN amplified Kelly neuroblastoma cells treated with 1 uM of the indicated compound for 6 hrs.

Degradation of MYCN Requires Conformation-Specific Inhibition of Aurora A and Phosphorylation of MYCN Although both VX-680 and CD532 bind to the ATP-binding kinase 'hinge' in an identical manner through their aminopyrazole-pyrimidine core, each contains distinct chemical components that produce highly divergent effects on MYCN in cells (FIGS. 3A and 15A). Crystallographic data suggest that several chemical moieties of CD532 were critical for its ability to destabilize MYCN. As expected, altering the urea moiety of CD532 decreased biochemical potency against Aurora A, as well as efficacy against MYCN in neuroblastoma cell lines (FIG. 3B). Structural data also shows that the 6-position of the pyrimidine backbone is oriented towards solvent, and addition of a methyl group to this position (CD15) maintained both cell-free potency and efficacy against MYCN (FIGS. 3B and 16B). These data are consistent with degradation of MYCN occurring as a consequence of on-target Aurora A Kinase conformation-disrupting activity of CD532.

Figure 3C:
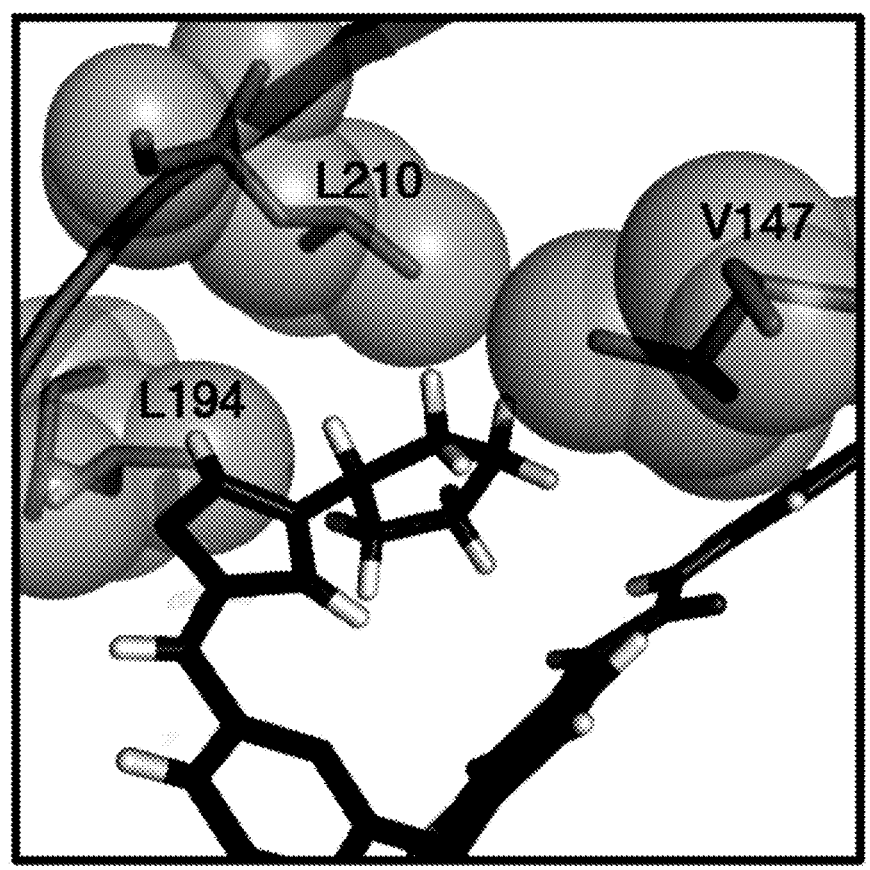
Figure 3D:
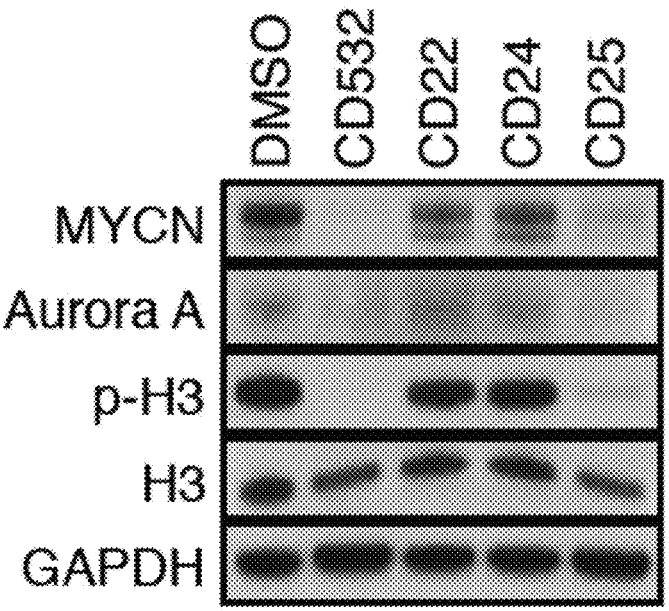

The cyclopentyl moiety of CD532 packs neatly in a hydrophobic pocket made by V147, L194, and the leucine gatekeeper (L210) (FIG. 3C). Thus our crystallographic data suggests that an additional methylene and adoption of the resulting six-membered ring into a chair conformation would preclude binding to Aurora A without abrogating binding to other kinases with a less bulky gatekeeper. Indeed, compounds CD22 and CD24 lost both potency against Aurora A and efficacy against MYCN (FIGS. 3D and 16B).

The sterically bulky trifluoromethyl interacts with and displaces the β1 and β2 strands, which stabilizes a global conformational change in Aurora A that is unable to protect MYCN from degradation (FIG. 2D). We hypothesized that replacement of this group with a hydrogen would decrease the magnitude of the N-terminal displacement of Aurora A without altering binding affinity. Indeed, CD25 retained potency against Aurora Kinase A activity as demonstrated biochemically and by loss of Histone H3 phosphorylation. However, CD25 was less effective than CD532 in driving MYCN loss, suggesting that the magnitude of the N-terminal shift of Aurora A contributes to MYCN destabilization (FIG. 3D).

CD532 Blocks S-Phase Entry and Reduces MYCN in a Mouse Model of MYCN Amplified Neuroblastoma Both Aurora A and MYCN are critical to different phases of the cell cycle, and the functional consequences of Aurora A kinase inhibition and MYCN loss are distinct. Inhibition of Aurora A blocks mitosis, causing a G2/M arrest (Manfredi et al., 2011). In contrast, MYC family proteins drive S-phase entry. Knockdown of MYCN protein blocks entry into S-phase causing a subsequent G0/G1 arrest (Gogolin et al., 2013). To compare functional differences between conventional Aurora A kinase inhibition (MLN8237 or VX-680) with conformation disrupting Aurora A kinase inhibition, we treated MYCN amplified neuroblastoma cells and measured cell cycle by flow cytometry (FIGS. 6, 13, 16 and 17). Treatment with MLN8237 or VX-680 resulted in G2/M arrest (FIGS. 6A and 16), consistent with inhibition of Aurora A kinase without a significant inhibition of MYCN. By contrast, CD532 resulted in potent loss of S-phase entry even after only 4 or 6 hrs of treatment, a result expected in response to inhibition of MYCN (FIGS. 6A, 13A, 16 and 17). This loss of S-phase was concomitant with loss of p-Histone H3 (FIGS. 12A and 6C), loss of p-pan-Aurora Kinase (FIG. 6C), and with loss of MYCN protein (FIGS. 12B and 6D). As Aurora kinase inhibitors, MLN8237, VX-680 and CD532 all caused loss of phospho-pan-Aurora, detectable in a small fraction of cells by flow cytometry (FIG. 6C). However, only CD532 also caused a loss of Sphase and MYCN (FIGS. 6A and 6D).

Figure 13A:
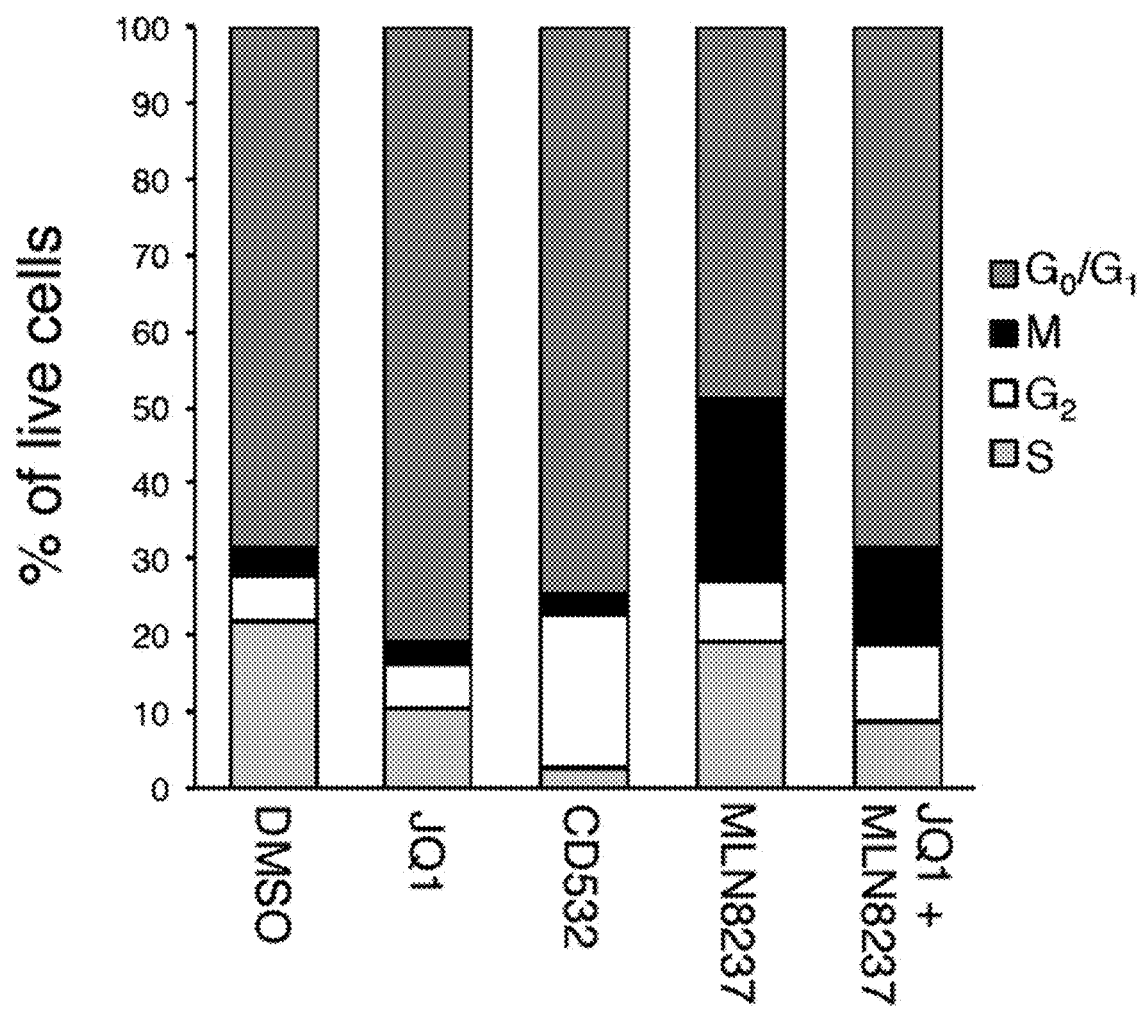
FIGS. 13A-F. CD532 acts as a MYCN inhibitor in cell lines and downregulates MYCN in vivo.

CD532 has the dual effect of blocking Aurora A kinase activity and driving degradation of MYCN. To further characterize the effects of CD532 on the cell cycle, CD532 was compared to the bromodomain inhibitor JQ1, which has been shown to block MYCN downstream transcriptional activity, as well as MYCN gene transcription in neuroblastoma (Puissant et al., 2013). MYCN amplified neuroblastoma cells were treated for 24 hrs with JQ1 to allow time for transcriptional events to occur. Treatment and resultant downregulation of MYCN in response to JQ1 (FIG. 17B) resulted in blockade of S-phase entry and accumulation of cells in G0/G1 (FIG. 13A). Treatment with CD532 for 4 hrs resulted in a rapid and potent loss of S-phase (consistent with the rapid and potent loss of MYCN protein) and accumulation in both G0/G1 and G2, consistent with a mixed Aurora A/MYCN effect. Treatment with MLN8237 for 4 hrs resulted in a modest downregulation of MYCN and accumulation of cells in G2 and M phase, which has been described previously (Manfredi et al., 2011). When JQ1 for 24 hr (blocking MYCN) and MLN8237 for 4 hr (blocking Aurora A kinase activity) were combined, an additive loss of S-phase and accumulation in G2/M was observed, similar to CD532.

That the cell cycle and viability activity of CD532 but not MLN8237 is related to degradation of MYCN suggests that expression of MYCN might confer sensitivity to CD532.

Figure 13B:
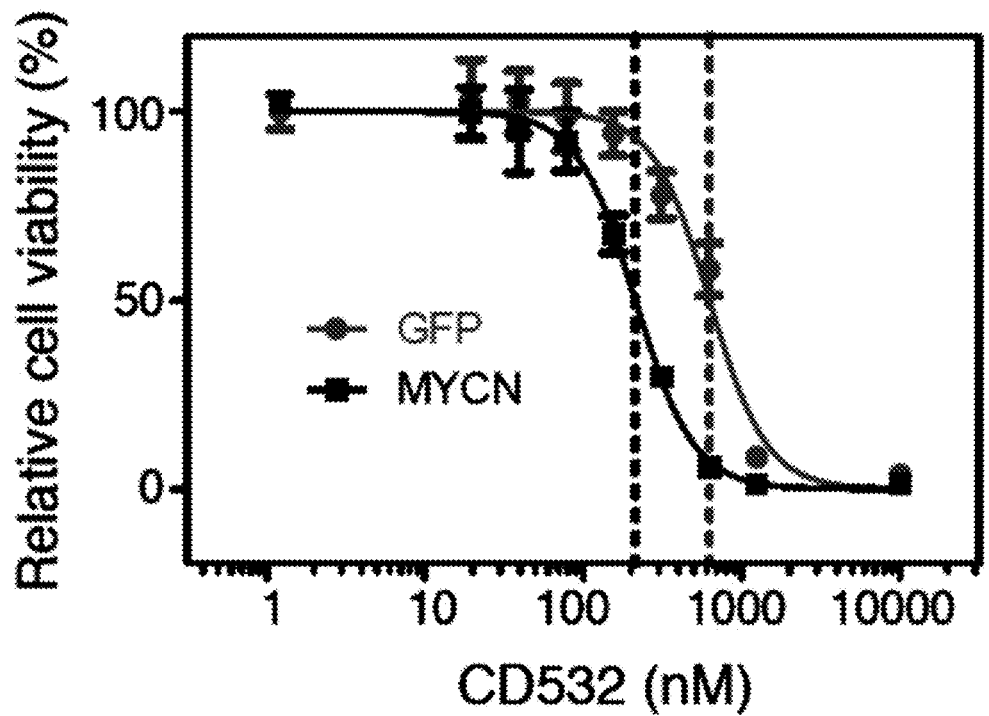
Figure 13C:
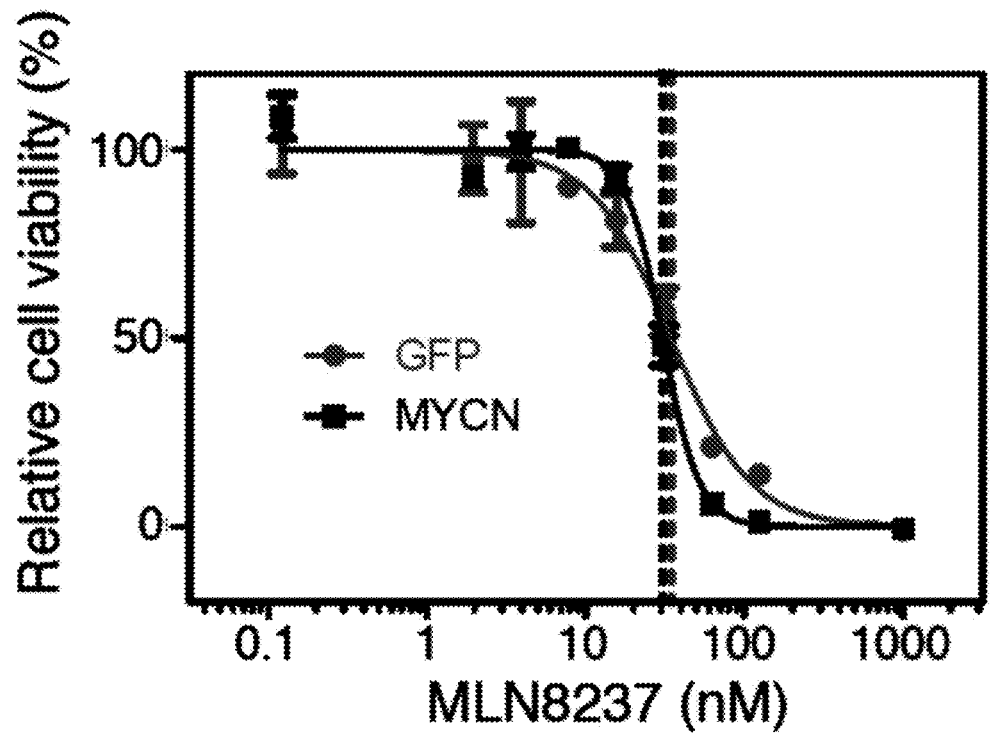
Figure 17A:
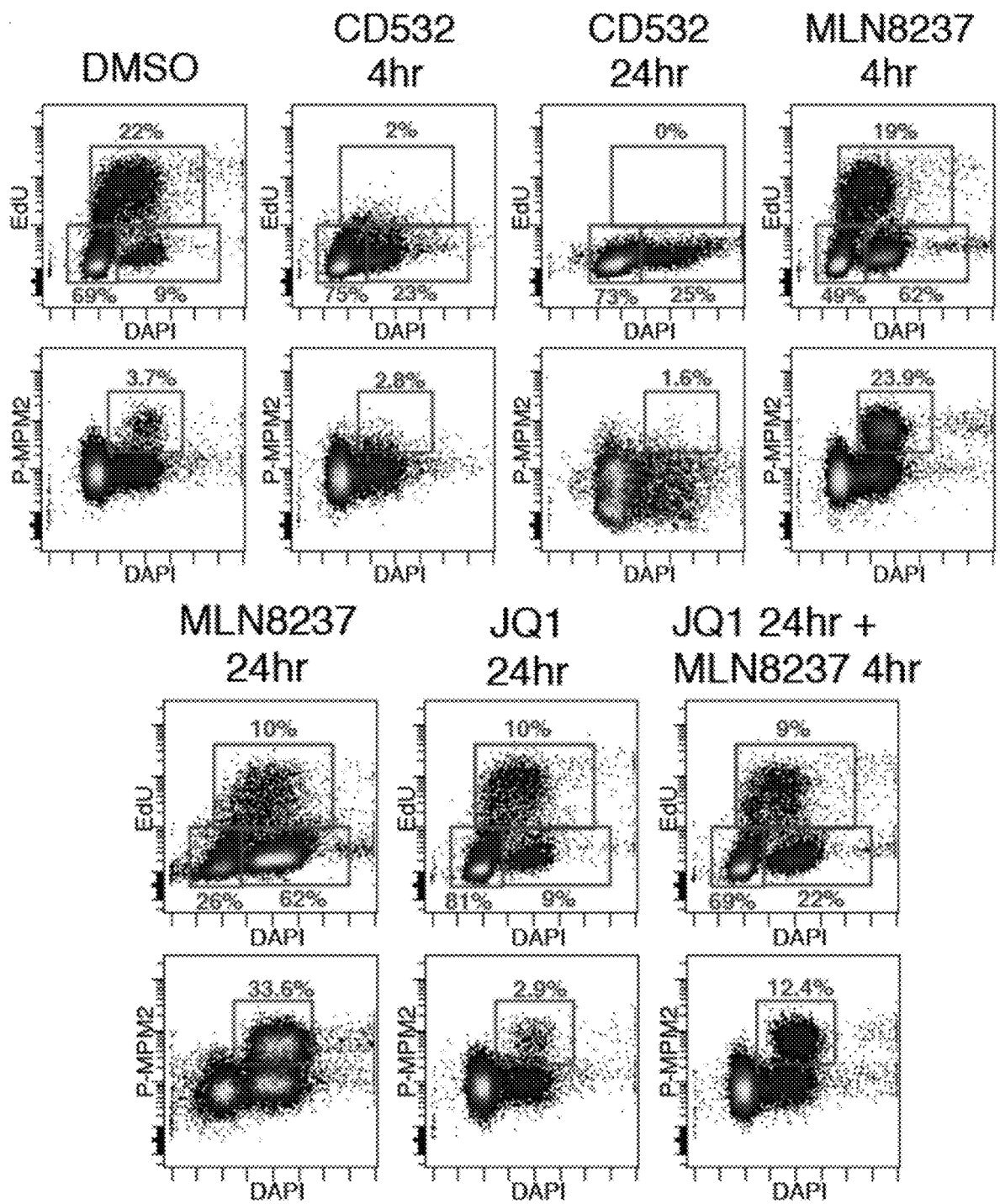
FIGS. 17A-E. CD532 cellular effect is through MYCN inhibition.
Figure 17B:
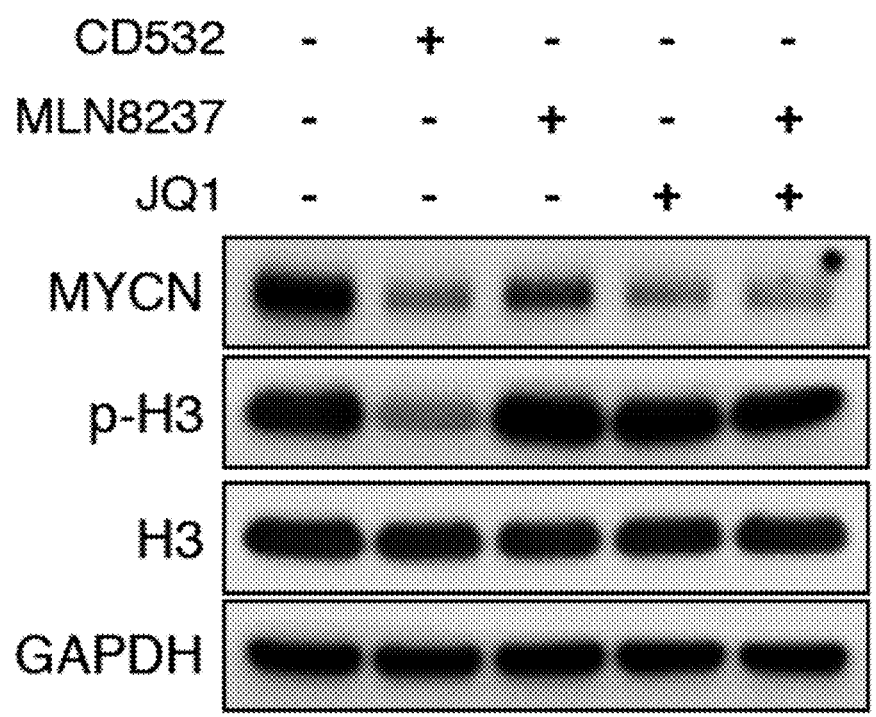
Figure 17C:
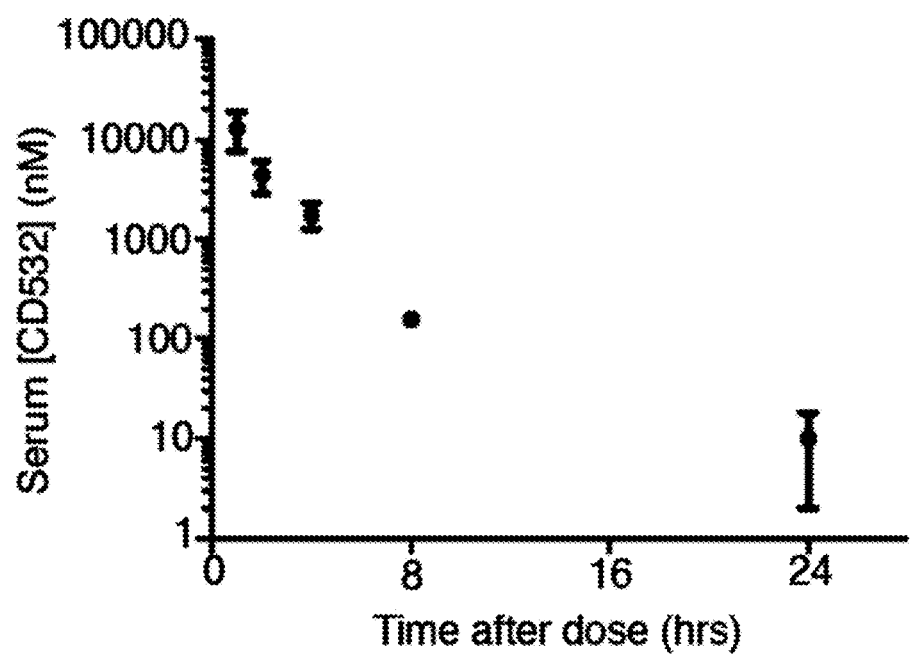
Figure 17D:
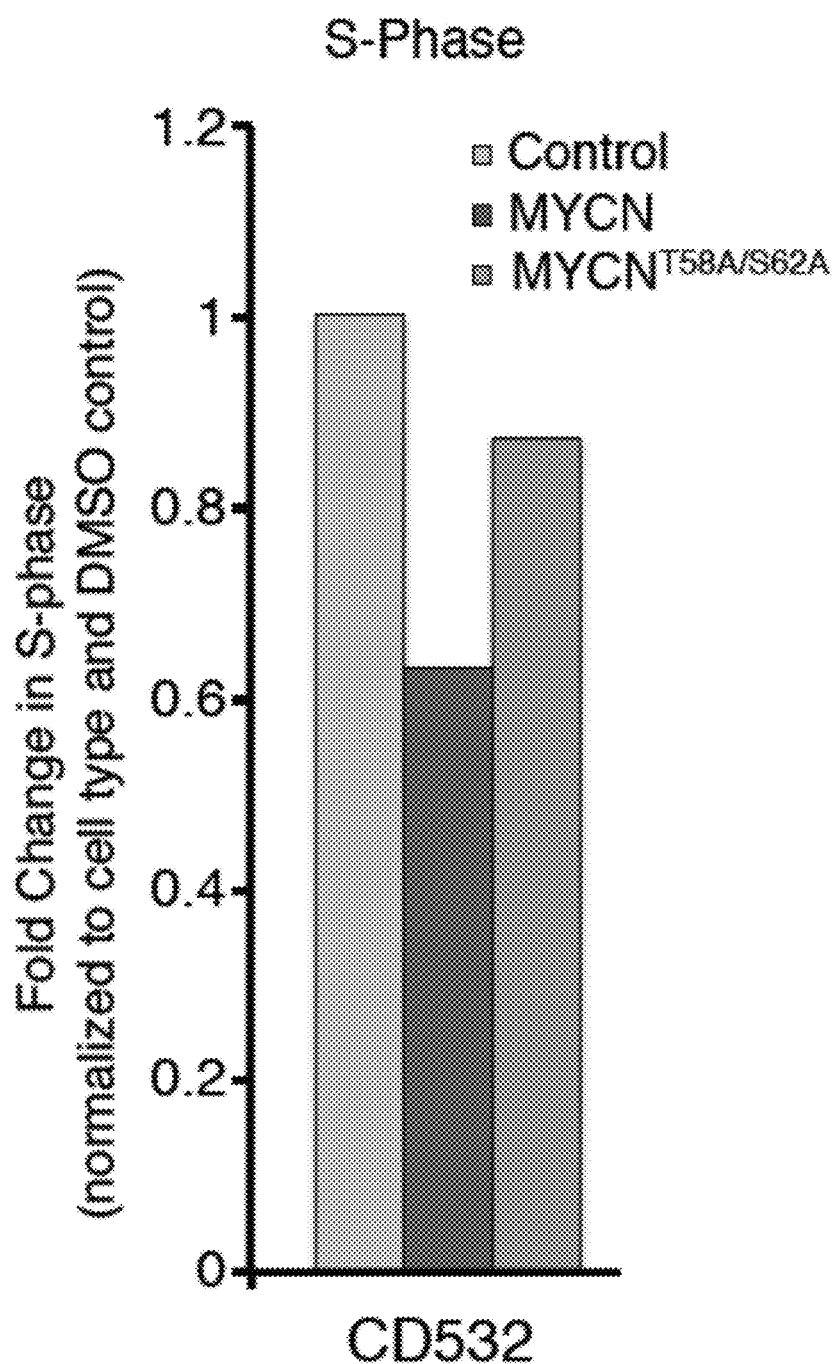
Figure 17E:
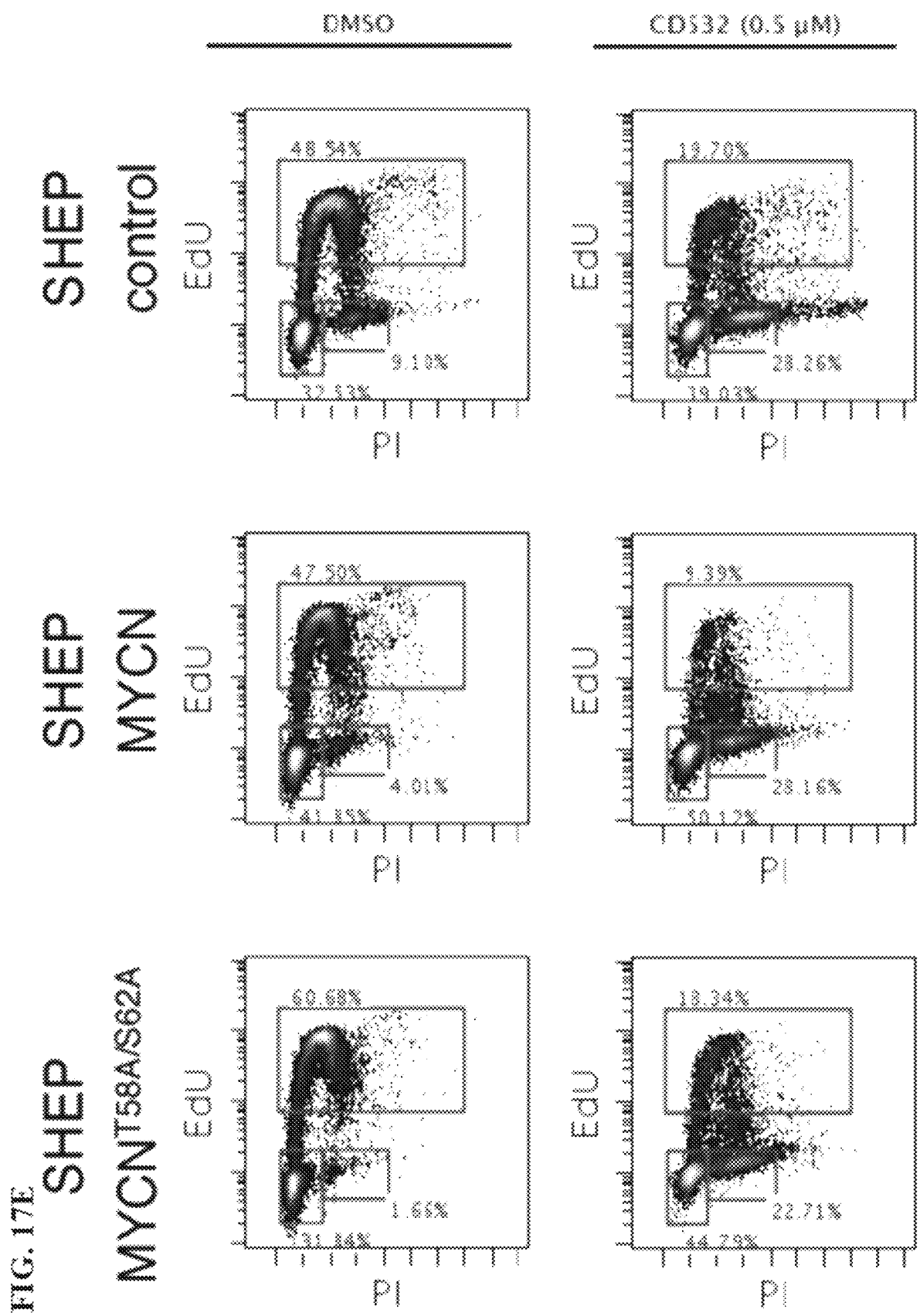

The cellular $EC_{50}$ for these compounds was determined against both GFP- and MYCN-transduced SH-EP neuroblastoma cells, which express little to no MYCN. Transduction of MYCN conferred sensitivity to CD532 but not to MLN8237 (FIG. 13B-C). In addition, CD532-driven loss of S-phase in these cells could be rescued by the stabilizing MYCNT58A/S26A mutant (FIGS. 17D and E). These data suggest that the efficacy of CD532 is due primarily to loss of MYCN, whereas that of MLN8237 is due primarily to inhibition of Aurora Kinase A.

Figure 13D:
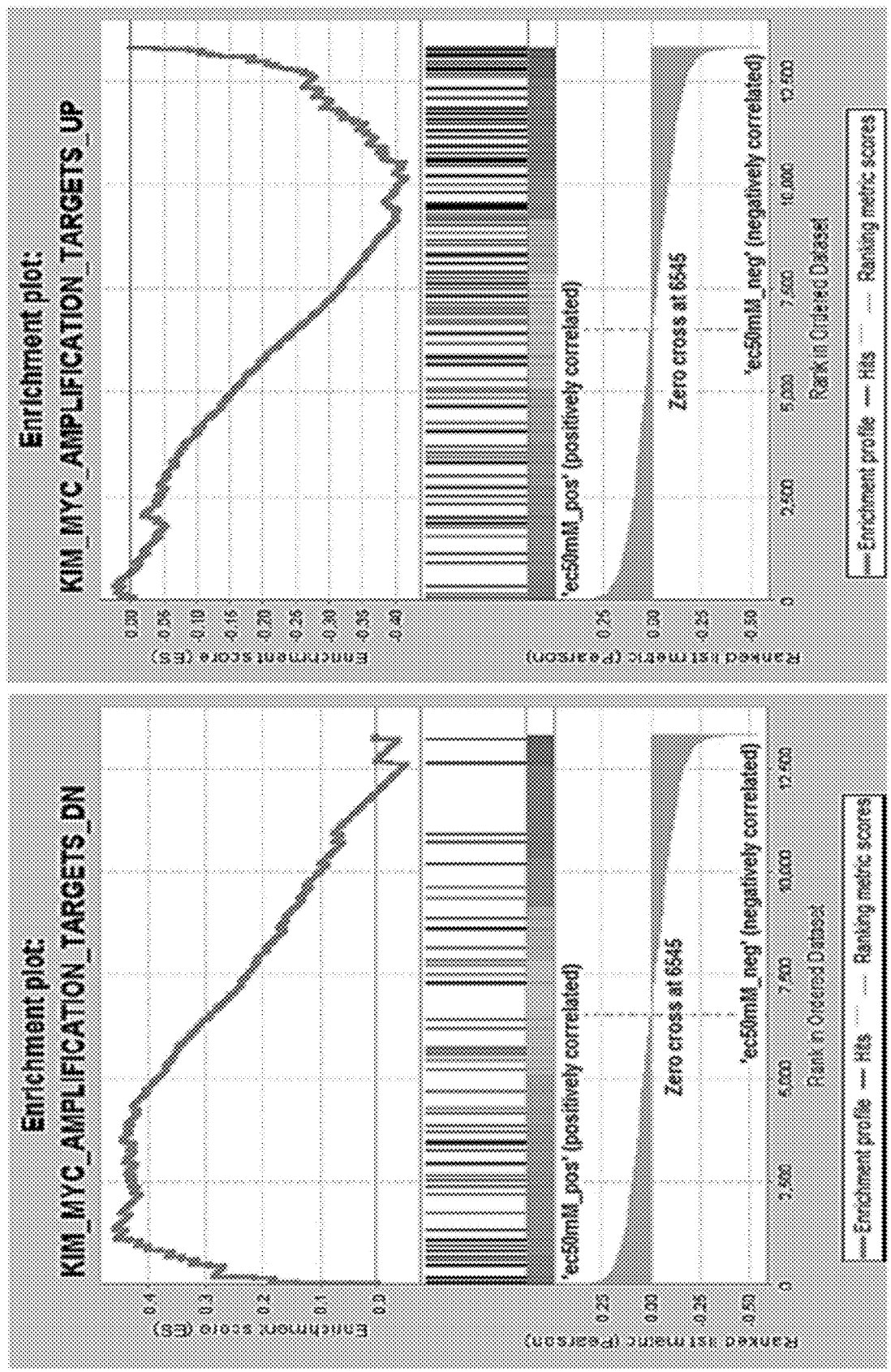
Figure 13E:
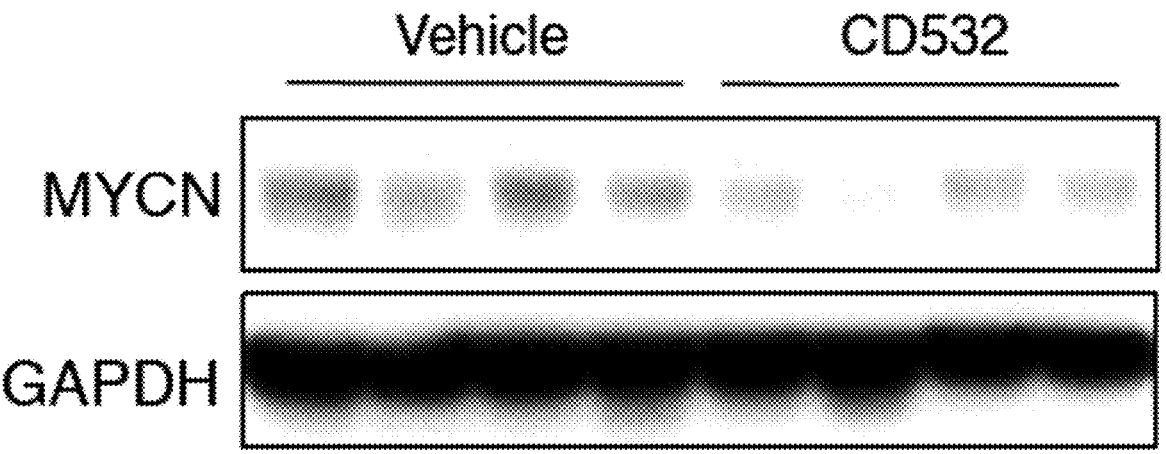
Figure 13F:
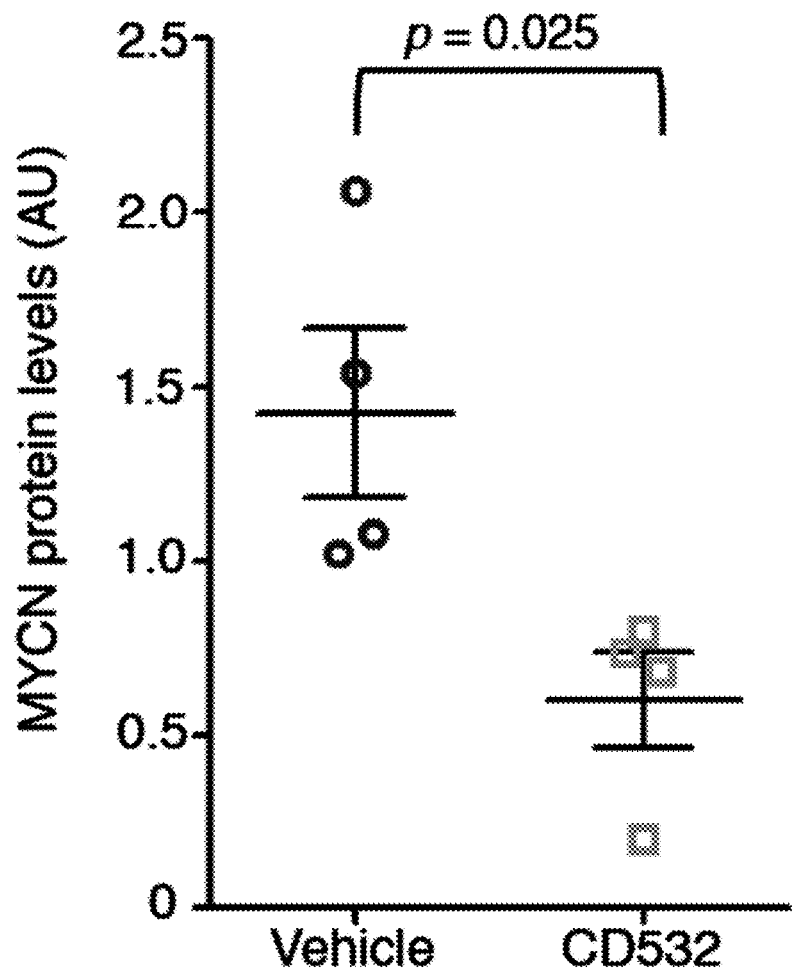
Figure 18A:
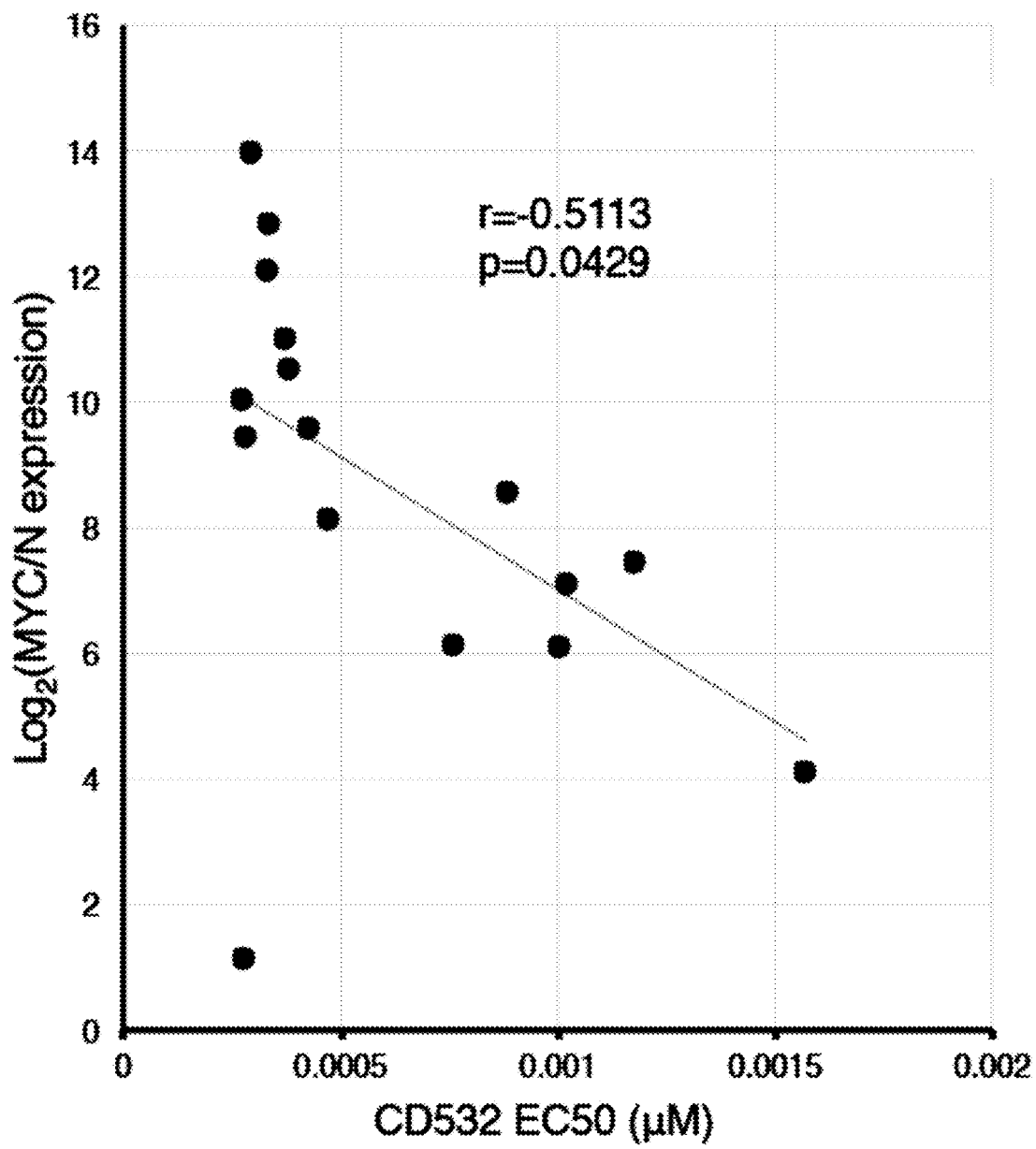
FIGS. 18A-D. Cancer cell lines are sensitized to CD532 by MYC/N expression.
Figure 18B:
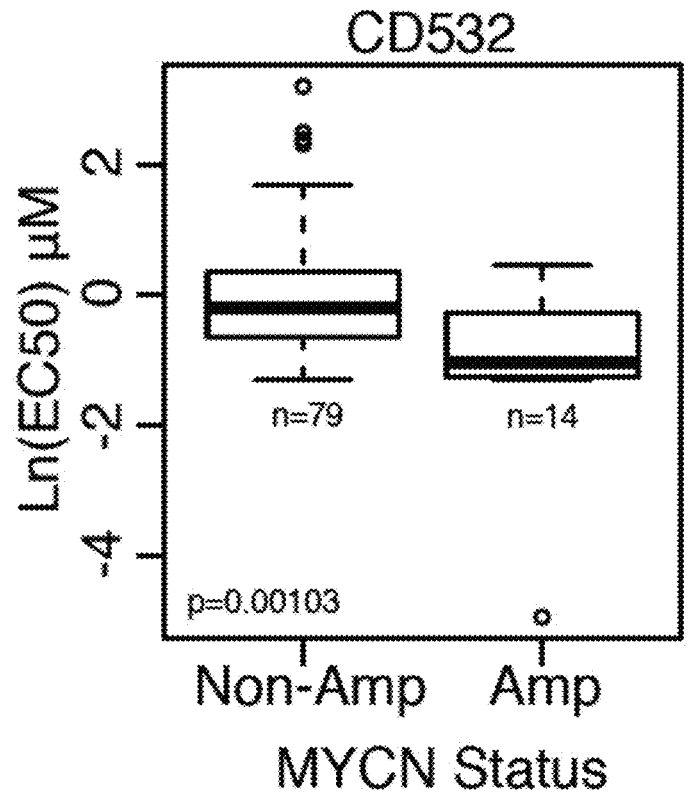
Figure 18C:
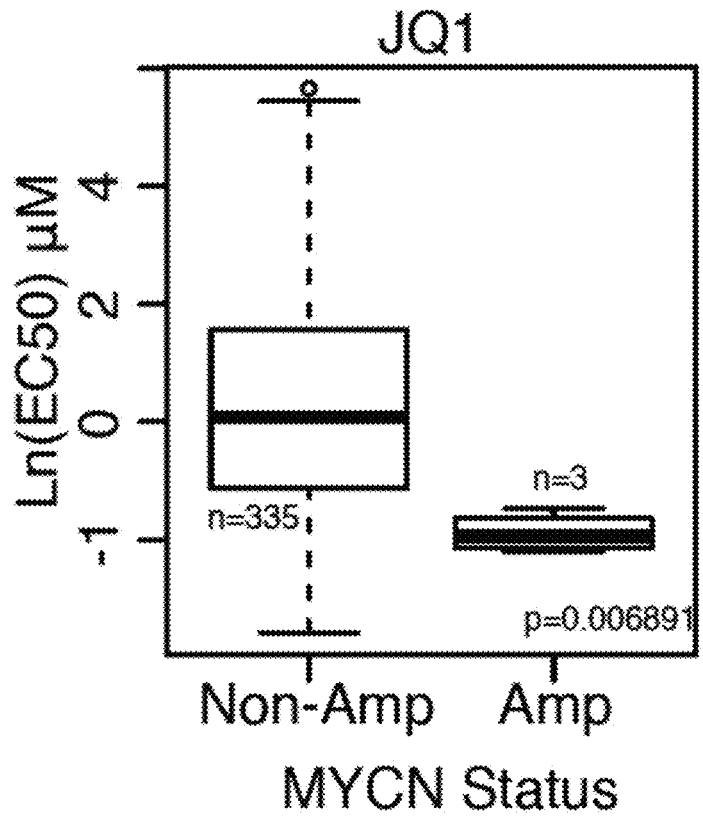
Figure 18D:
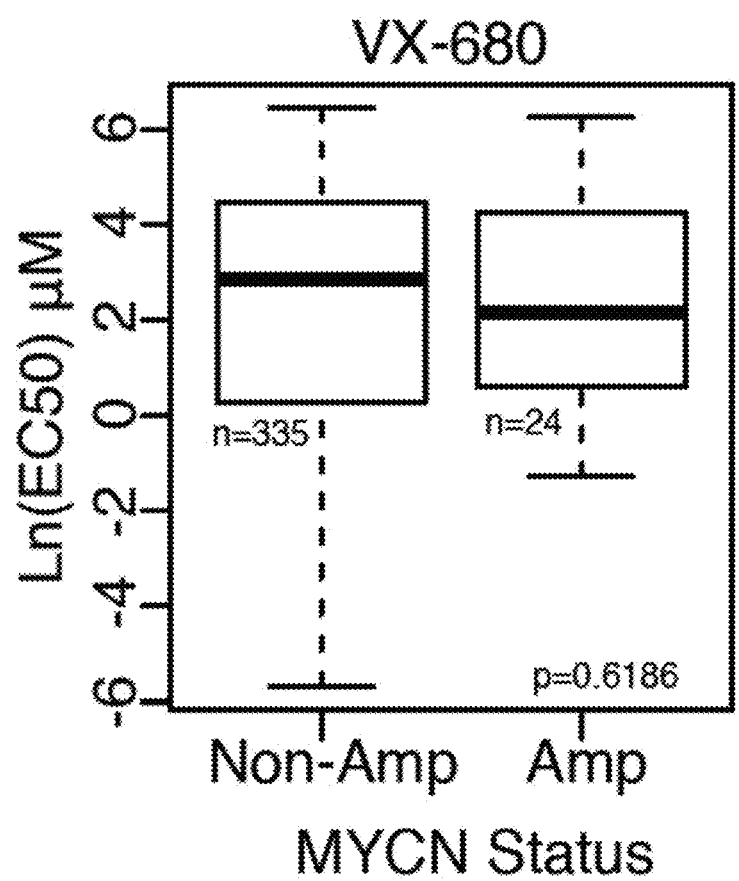

To determine whether MYCN might serve as a biomarker of sensitivity to CD532, a panel 169 distinct tumor-derived and genetically characterized cell lines were screened, including 93 lines for which MYCN copy number was available, and 87 lines for which mRNA expression data were available (Garnett et al., 2012). CD532 showed activity in most cell lines, with $EC_{50}$ values in the nanomolar range, consistent with our results in neuroblastoma (Table 2). Sensitivity to CD532 correlated with expression of MYCN/MYC mRNA in neuroblastoma cells (FIG. 18A). MYCN amplified cell lines were significantly more susceptible to CD532 than non-amplified lines (p=0.0010). In validation of this analysis, MYCN amplified lines were significantly more susceptible to JQ1 than non-amplified lines (p=0.0069), whereas MYCN amplified and non-amplified lines showed similar sensitivity to VX-680 (p=0.618; FIGS. 18B-D). Gene-set enrichment analysis revealed that susceptibility to CD532 correlated with a MYC signature, i.e. lowest $EC_{50}$ in cells with highest expression of MYC targets and highest EC50 in cells with downregulated MYC targets (FIG. 13D). These data support a broad potential for CD inhibitors of Aurora A against tumors in addition to neuroblastoma, and suggest a role for CD Aurora A inhibitors in both MYC and MYCN driven diseases.

CD532 represents a first-in-class tool compound and its in-vivo pharmacokinetic properties were assessed. Studies in mice revealed a serum half-life of ~1.5 hrs, providing for an $AUC_0$-24 of 27 μM*h when delivered at 20 mg/kg (FIG. 17C). This is in contrast to clinically developed compounds, such as MLN8237, which has an $AUC_0$-24 of 78.4 μM*h when delivered at the same dose (Carol et al., 2011). Nonetheless, treatment ofMYCN-amplified neuroblastoma xenografts with CD532 led to decreased levels of MYCN protein (FIGS. 13E and 13F), demonstrating that CD532 can block MYCN protein in vivo.

Figure 14A:
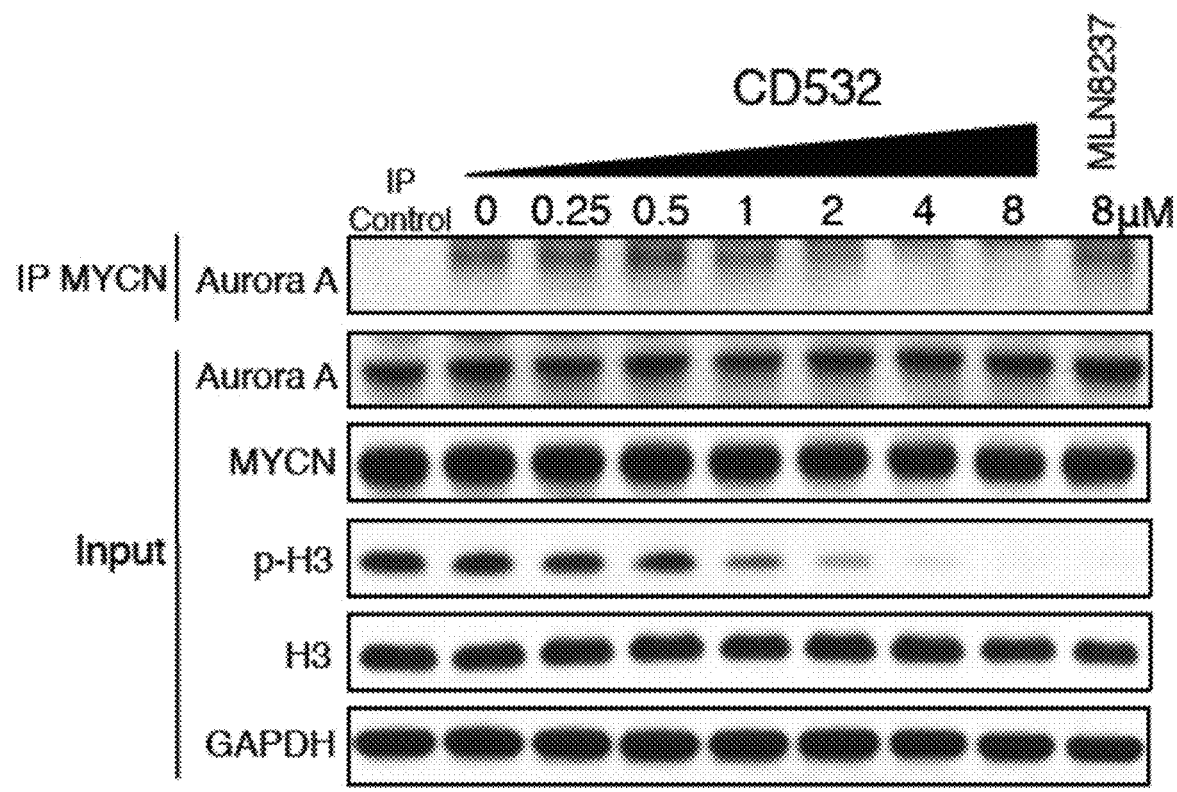
FIGS. 14A-C. CD532 and MLN8237 have distinct kinetic effects on MYCN loss and Aurora A kinase inhibition: Representative immunoprecipitation of MYCN and immunoblots from MYCN-amplified IMR32 cells treated for 4 hrs with MG-132 and 2 hrs with increasing concentrations of (FIG. 14A) CD532 or (FIG. 14B) MLN8237.
Figure 14B:
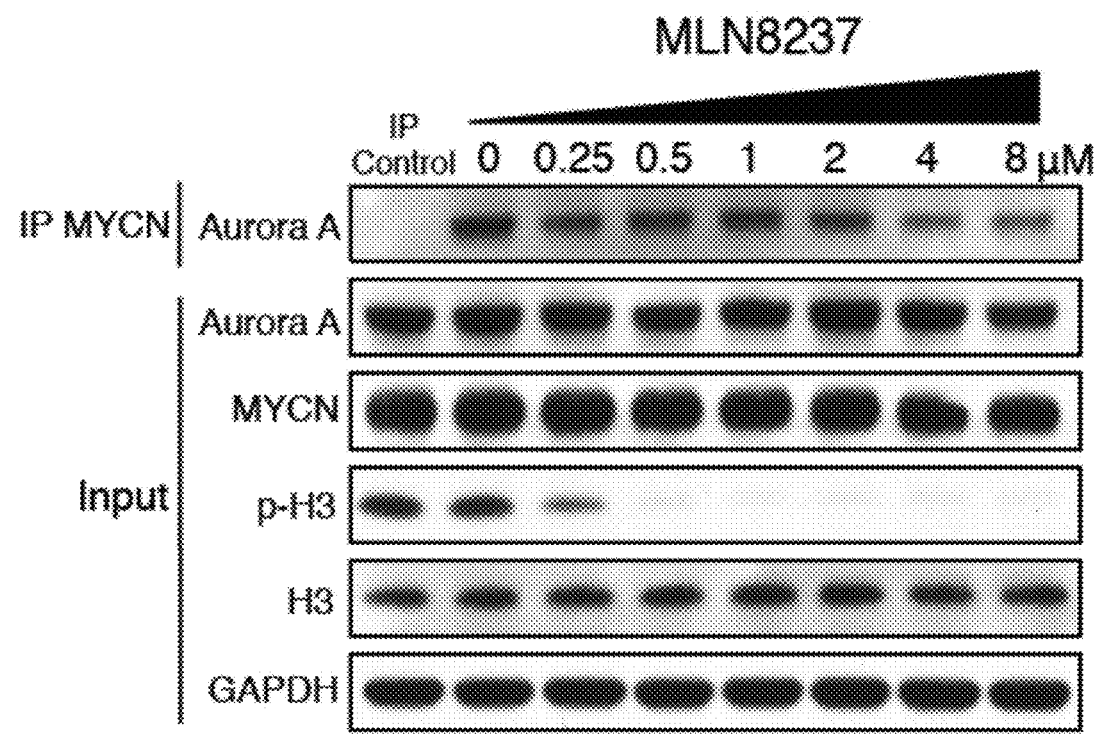
Figure 14C:
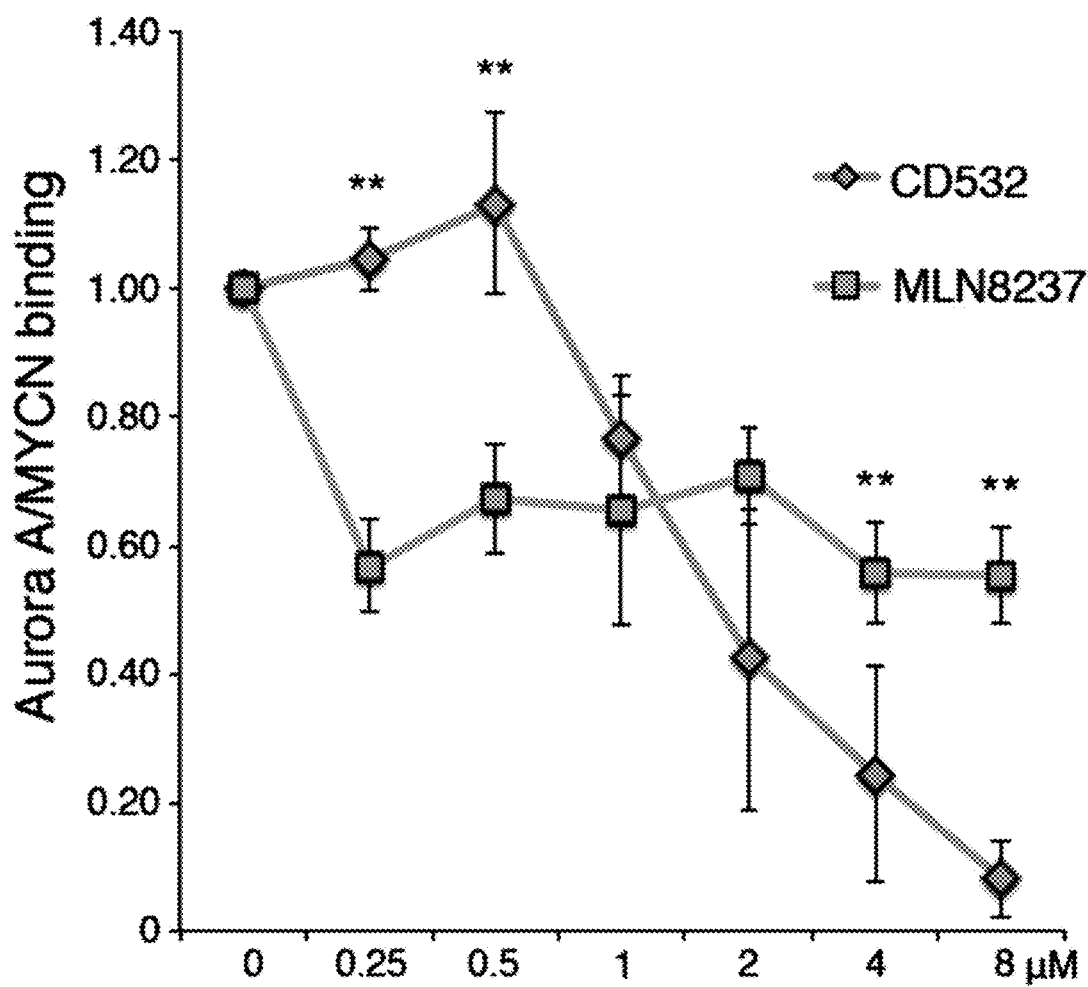
Figure 19A:
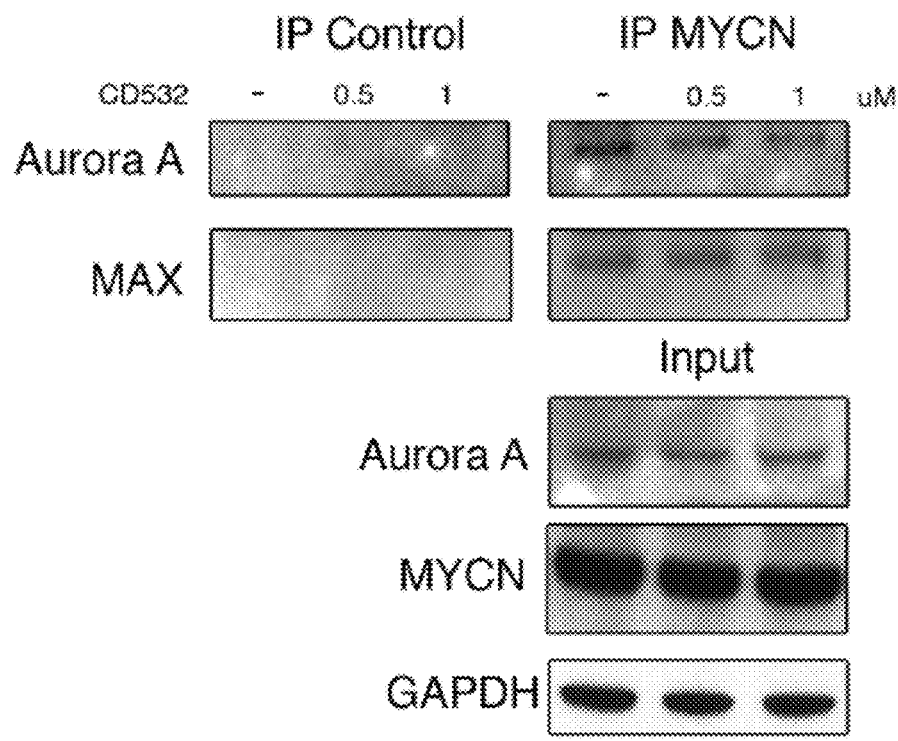
FIGS. 19A-B. CD532 disruption is specific to MYCN-Aurora A complex.
Figure 19B:
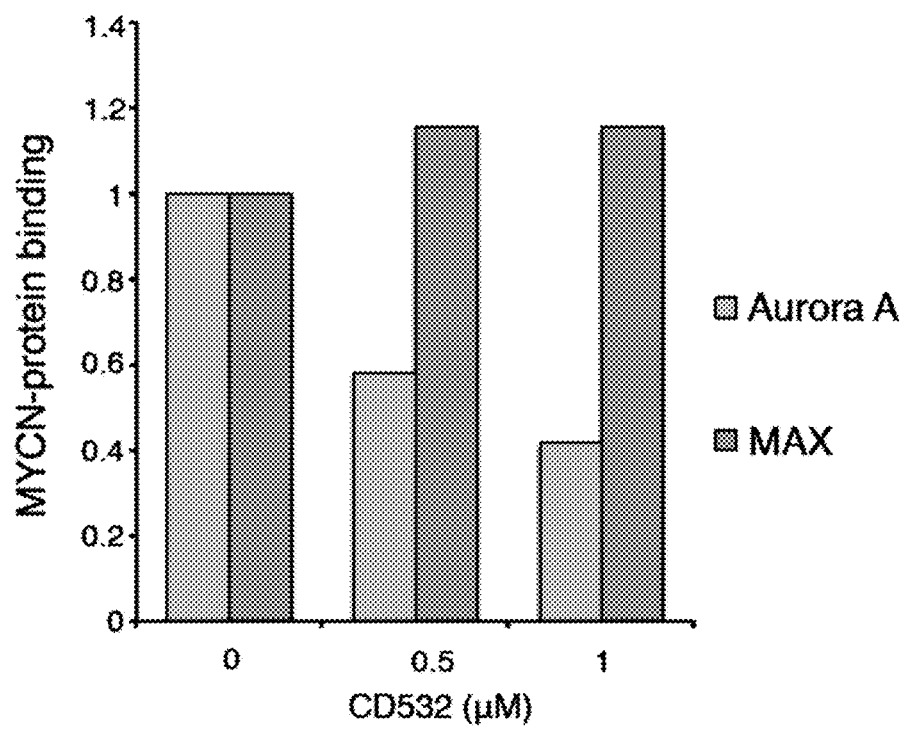
Figure 20A:
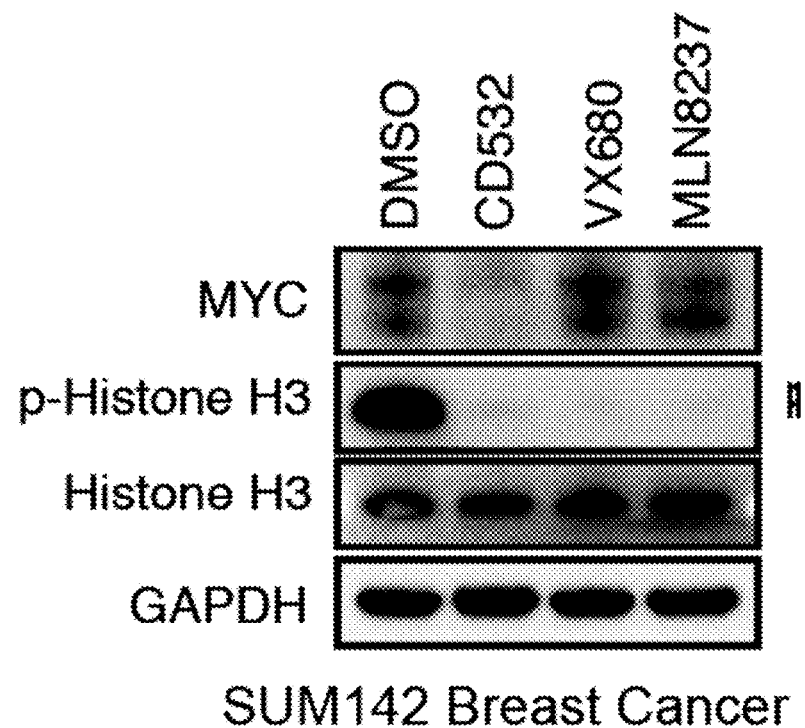
FIGS. 20A-C. CD532 applications in c-MYC driven diseases: CD532, but not other Aurora A inhibitors, effects loss of c-MYC protein in (FIG. 20A) SUM142 breast cancer, (FIG. 20B) RKO colon cancer, and (FIG. 20C) c-MYC-translocated ML-60 leukemia cell lines.
Figure 20B:
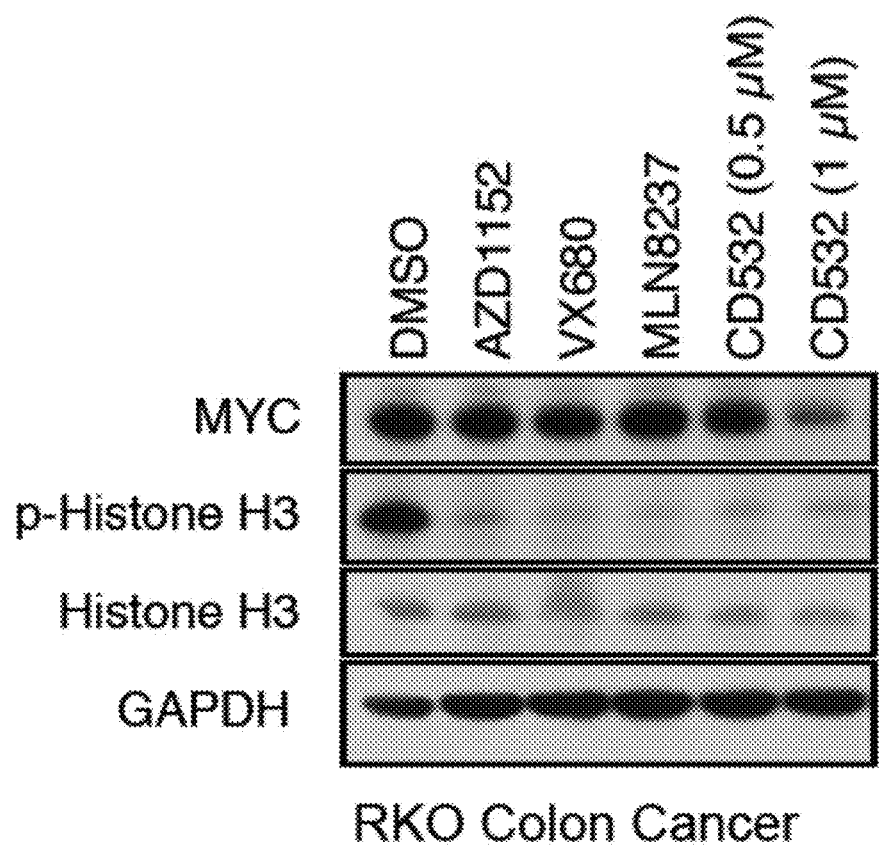
Figure 20C:
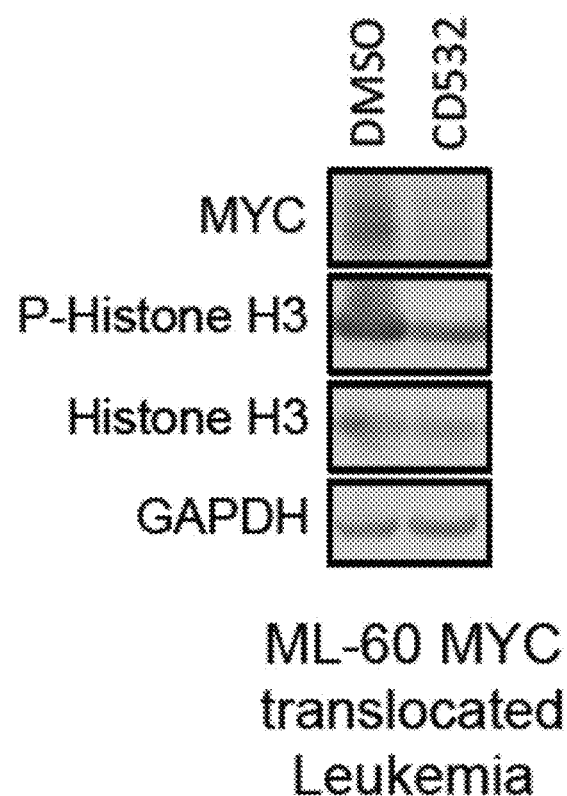
Figure 21:
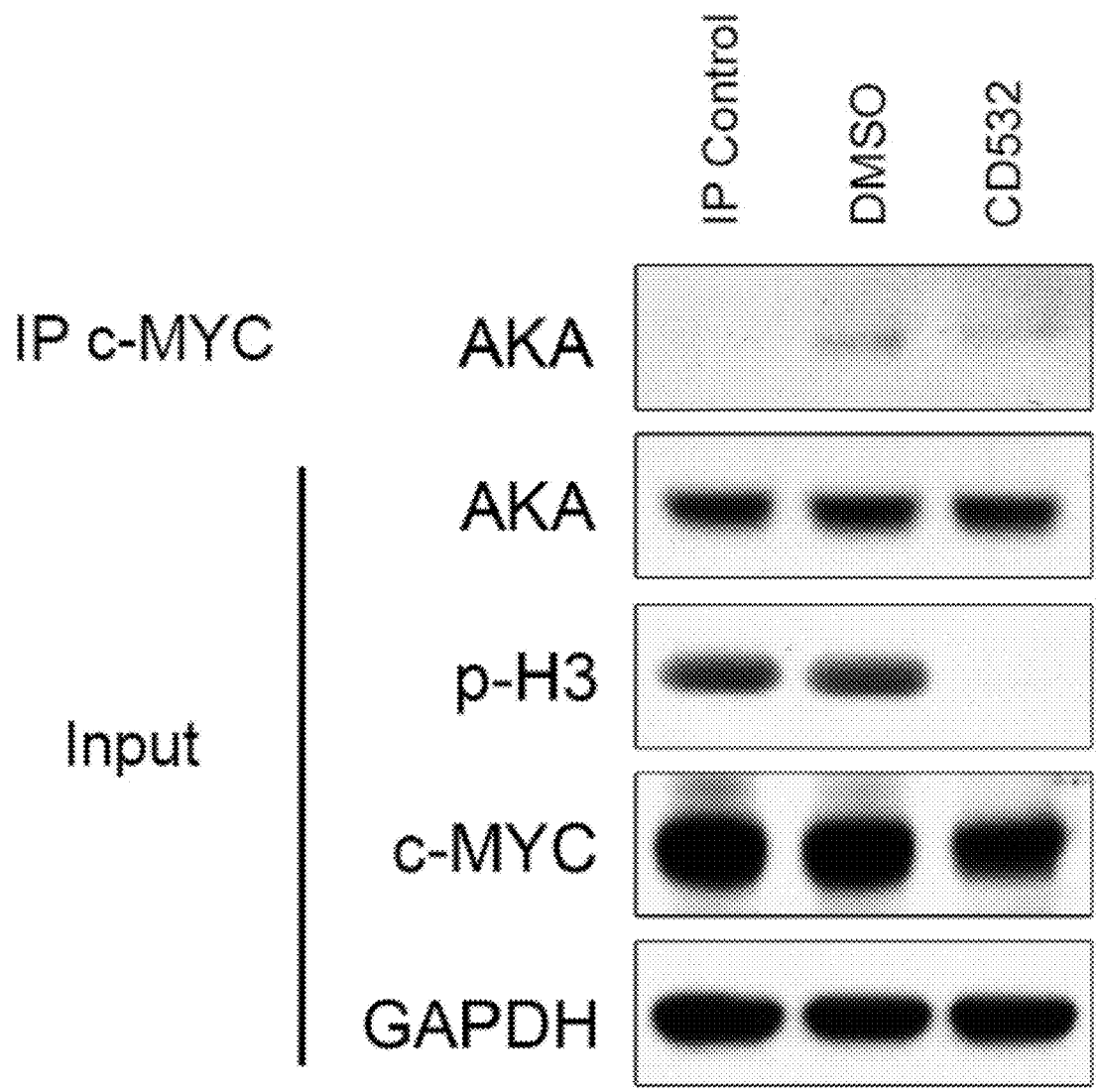
FIG. 21. Aurora A associates with c-MYC and CD532 disrupts this interaction: Immunoprecipitation (IP) of c-MYC and immunoblotting for Aurora A (AKA) demonstrates that c-MYC physically associates with Aurora A and that CD532 treatment reduces this interaction in RKO colon cancer cell line.
Figure 22:
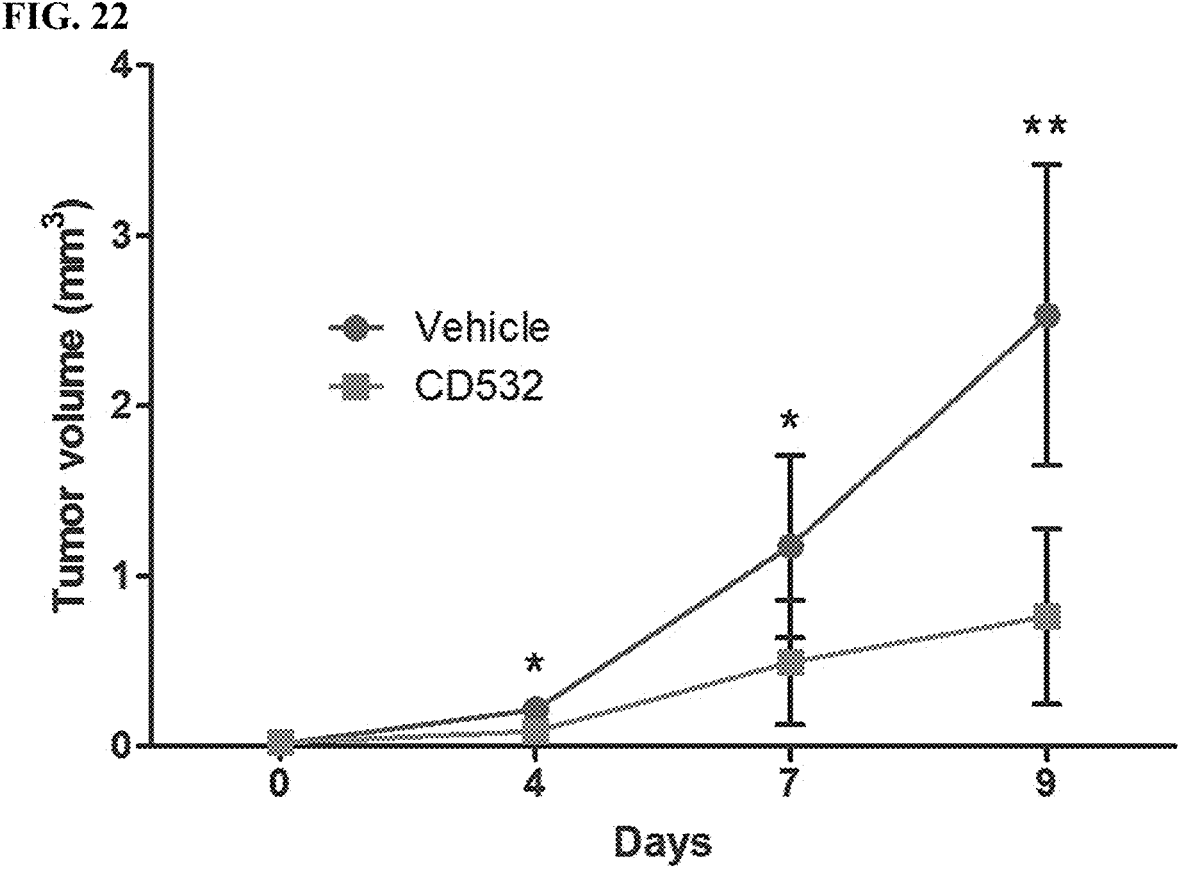
FIG. 22. CD532 inhibits growth of MYCN-expressing, SHH-subtype medulloblastoma allograft in mice: 25 mg/kg CD532 (n=5) or vehicle (n=6) were delivered b.i.w. by intraperitoneal injection and tumor size was measured over time.
Figure 23:
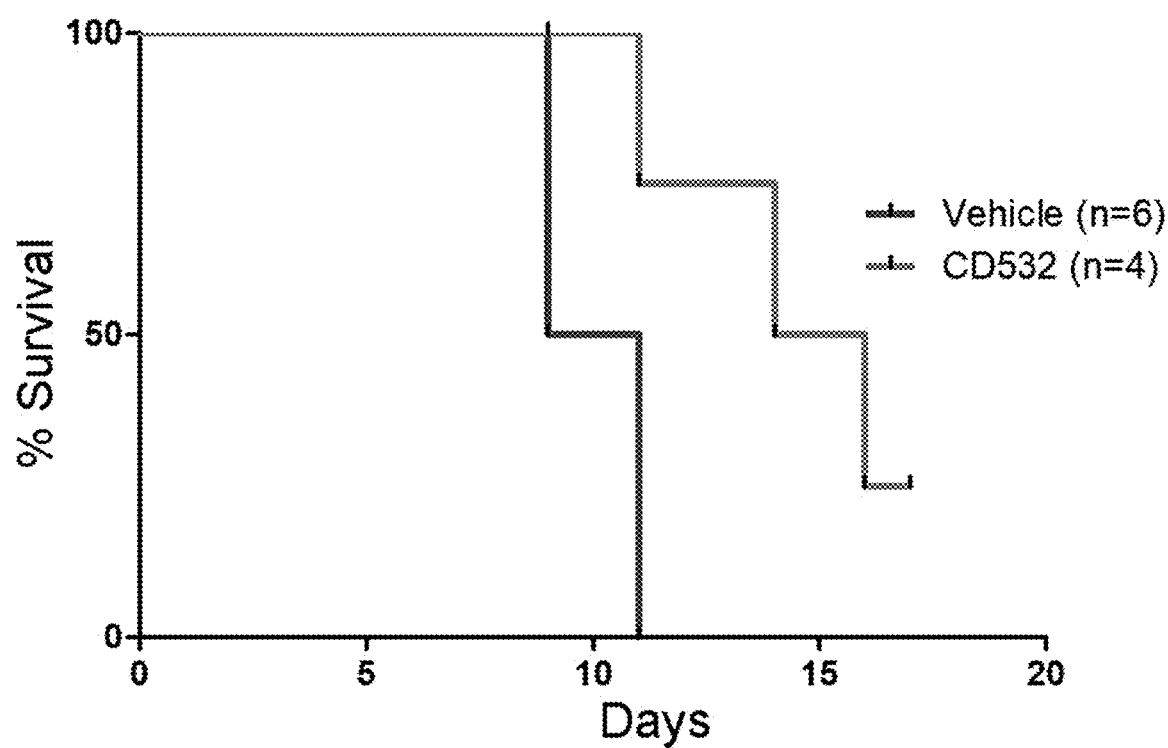
FIG. 23. CD532 inhibits growth of MYCN-expressing, SHH-subtype medulloblastoma allograft in mice: survival curve for the tumor volume of FIG. 22; statistical significant increase in overall survival (p=0.01 using Log-rank test, Hazard ratio=11.50 with 95% confidence interval of 1.75-75.49).

Disruption of the MYCN-Aurora A Complex Depends on the Magnitude of Conformational Change in Aurora A Despite its potency against Aurora A kinase activity and modest effect on the conformation of Aurora A (Dietrich et al., 2010; Dodson et al., 2010; Filomia et al., 2010; Toyoshima et al., 2012), MLN8237 subtly decreased MYCN protein levels compared to CD532 (FIGS. 1D, 12A, 7A and 7B). To test how the degree of conformational shift in Aurora Kinase A affects binding of MYCN and Aurora A, the MYCN-Aurora A interaction was measured in MYCN-amplified neuroblastoma cells treated with increasing concentrations of CD532 or MLN8237. CD532 inhibited histone H3 phosphorylation at concentrations 10-fold higher than MLN8237, consistent with their respective biochemical $IC_{50}$ values and cellular $EC_{50}$ values (FIG. 14A-B). However, CD532 caused a dose-dependent and complete dissociation of the MYCN-Aurora A complex at 2 h, whereas MLN8237 only modestly disrupted this interaction (FIG. 14A-C). This dissociation did not occur with VX-680 treatment, and was specific to the MYCN-Aurora A interaction, as CD532 did not affect MYCN-MAX binding (FIG. 19A-B). Disruption of the MYCN-Aurora A complex by CD532 occurred at doses comparable to those required to block p-H3, consistent with conformation-disruption as a consequence of CD532 binding (FIG. 14A). This is in contrast with MLN8237, which showed only partial disruption of the complex upon maximal Aurora A inhibition. Thus MLN8237, a more potent Aurora binder, only modestly decreased the affinity of Aurora A for the MYCN complex. By comparison, CD532 binds Aurora A with lower affinity, but has a dramatic effect on Aurora A binding to the MYCN complex (FIG. 14C).

Figure 4A:
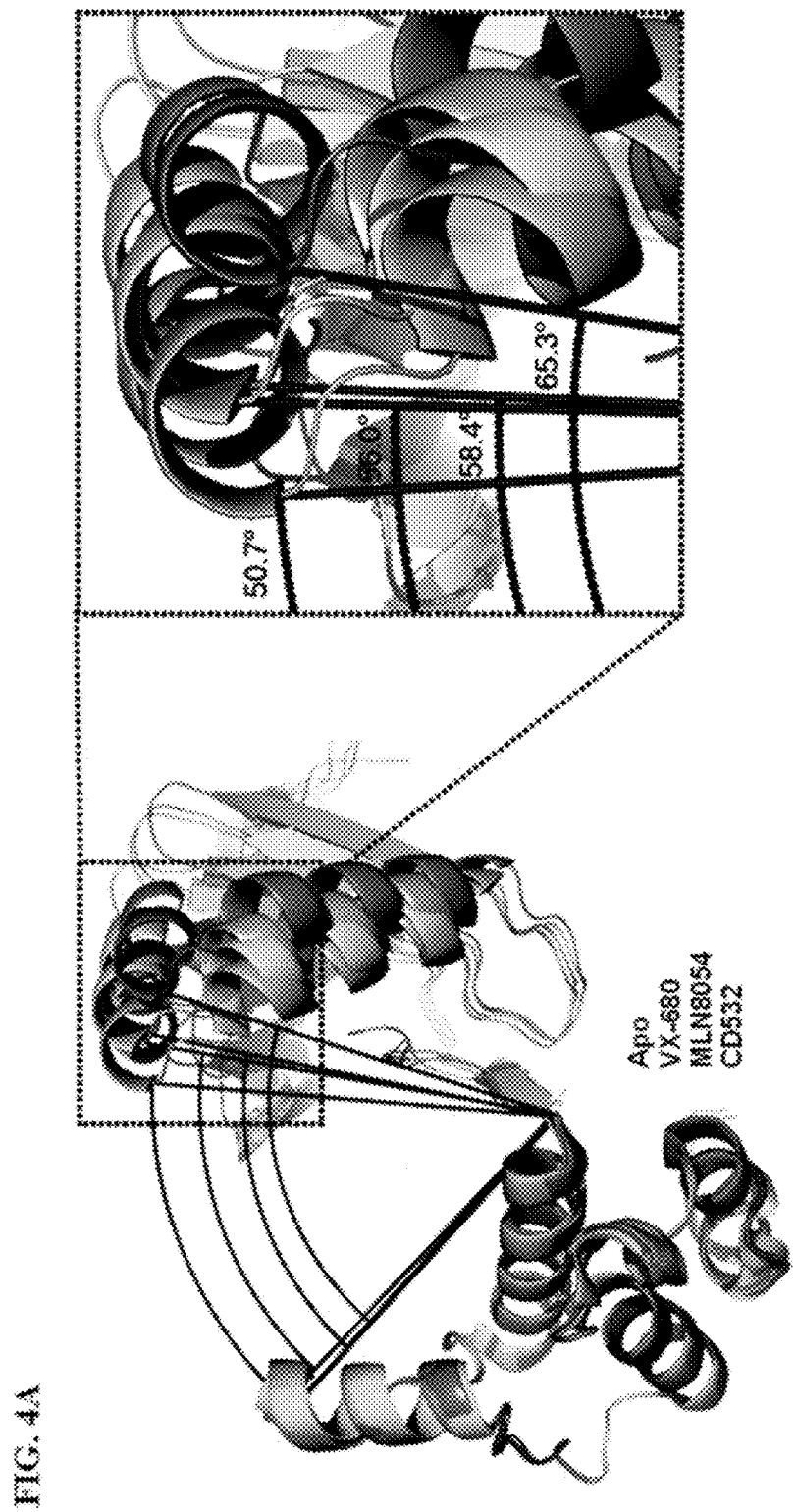
FIGS. 4A-C. Loss of MYCN tracks with the degree of conformational change in Aurora Kinase A.
Figure 4B:
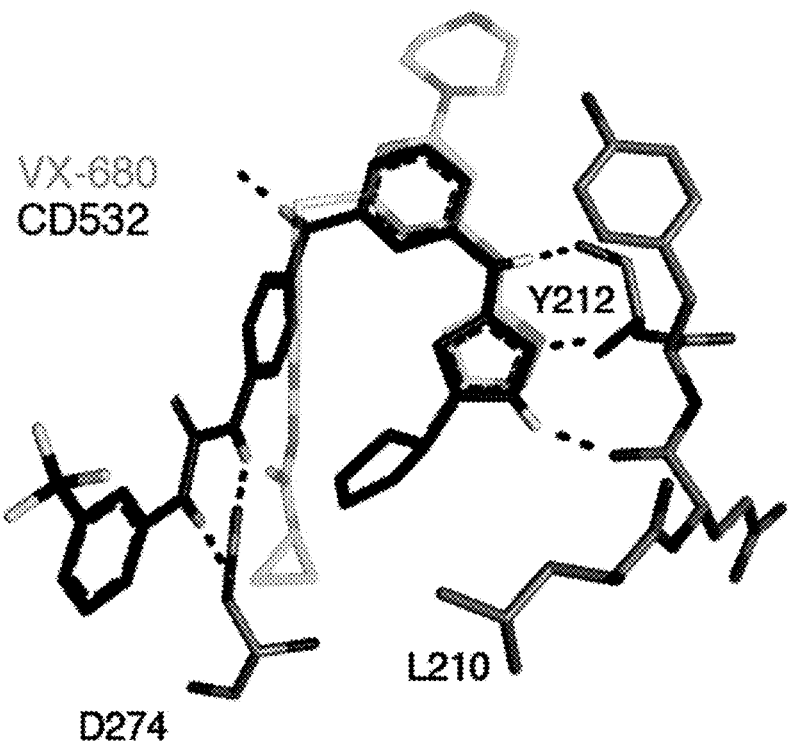

Data in FIG. 1D demonstrate that VX-680, MLN8237 and CD532 show increasing activity in driving destabilization of MYCN protein in MYCN amplified cell lines. Comparing the published structures of Aurora A bound to VX-680 and MLN8054 with our structure of Aurora A bound to CD532 demonstrates a progressive disruption of the conformation of Aurora A (FIG. 4A). As intended through use of the diaminopyrimidine scaffold for screening, CD532 binds to Aurora A at the hinge region via a pyrazole moiety in a manner similar to VX-680 (FIG. 4A), yet interacts with other parts of the Aurora A binding pocket to confer distinct biological effects (loss of MYCN, decreased viability, and loss of S-phase), biophysical effects (shift in tertiary structure), and biochemical effects (disruption of the Aurora A/MYCN complex). Thus the ability of VX-680, MLN8237 and CD532 to progressively displace the α-C helix in Aurora (a structural measure which tracks directly with MYCN proteolysis, FIGS. 4B and 4C) illustrates how a starting scaffold can be modified to effect divergent biochemical and biological activities.

Analysis

Understanding of kinase signaling has focused primarily on the sequential phosphorylation-dependent regulation of downstream targets. Such studies clarified a central role for Aurora Kinase A in mitosis and transformation. Aurora A shares significant structural and sequence similarity with Aurora B, although these proteins have both distinct mitotic functions and distinct subcellular localizations. These differences in both function and localization are attributed in part to the specific association of each kinase with a unique group of cofactor proteins (reviewed in (Carmena et al., 2009; Crosio et al., 2002; Liu et al., 2004; Ouchi, 2004; Scrittori et al., 2001; Zhao et al., 2008)).

Herein is described a class of compounds that were initially designed to bind Aurora A in a type II fashion, defined by the DFG-out orientation of D274, as a strategy for inducing a larger conformational change of the kinase. Thus it was surprising to observe that CD532 binds Aurora A as DFG-in, yet still induces a larger conformational disruption than the only known true type II Aurora inhibitors (Martin et al., 2012; Nussinov and Tsai, 2013). Comparing CD532-bound Aurora to the Apo structure shows the activation loop in the inactive orientation, accompanied by a shift in the entire N-terminal domain. Although the activation loop flip is consistent with an inactive conformation of Aurora Kinase A, polar contacts with the urea moiety of CD532 interact with the DFG motif, locking it in the active "DFG-in" orientation. This unusual conformation is achieved through a steric clash of the trifluoromethylphenyl moiety of CD532 with Aurora's N-terminal β1 and β2 strands, displacing the N-terminal lobe of Aurora A and allowing a unique network of hydrogen bonds to stabilize the activation loop in an inactive orientation.

The structural data also suggest a mechanism through which an inhibitor can stabilize the inactive conformation of a kinase. Previously described inhibitors that stabilize kinases in their active conformation displaced the aspartic acid of the catalytic DFG motif, with a concomitant crankshaft-like 180° rotation of the DFG backbone. In contrast, CD532 induces this inactive conformation through interaction with the β1/2 strands of the N-terminal domain, without reorienting the DFG motif. This structure thus reveals a novel "uncoupling" of the DFG-flip from the inactive state of a kinase, a coupling which had heretofore been regarded as obligate.

The resulting conformation of CD532-bound Aurora A blocks both kinase-dependent and MYCN-stabilizing, kinase independent functions of Aurora A. CD532 inhibits Aurora Kinase A at low nanomolar concentrations, and in parallel, effects proteolytic degradation of MYCN. Indeed, kinase inhibition and MYCN proteolysis were unable to uncoupled through structural modification of CD532, consistent with disruption of Aurora Kinase A's scaffold as a result of bulky pharmacophores that extend from an ATP-competitive core.

Figure 4C:
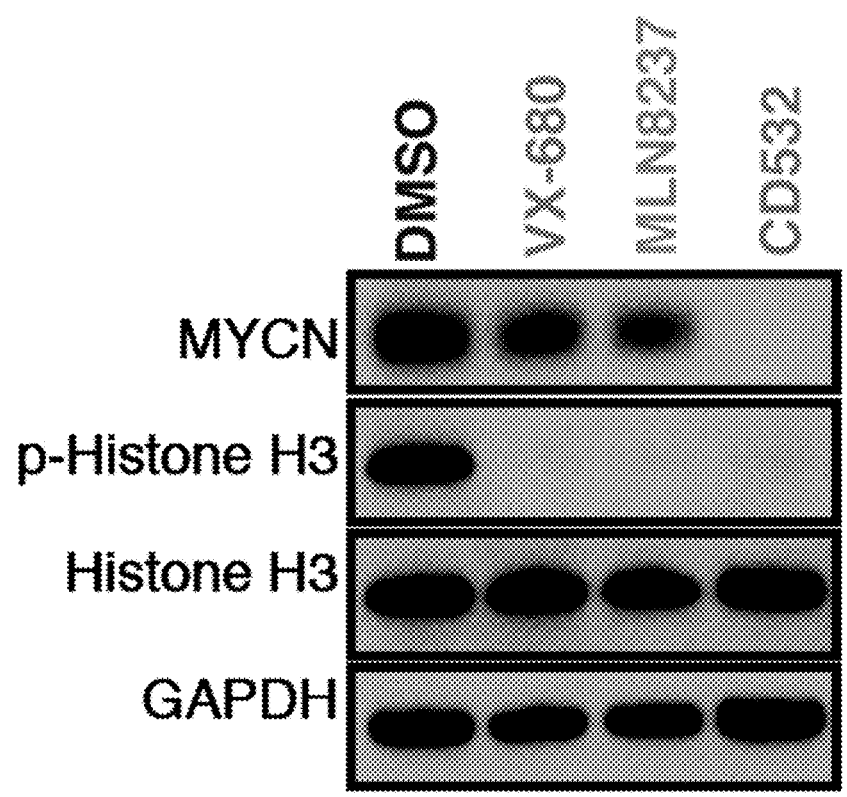
Figure 5A:
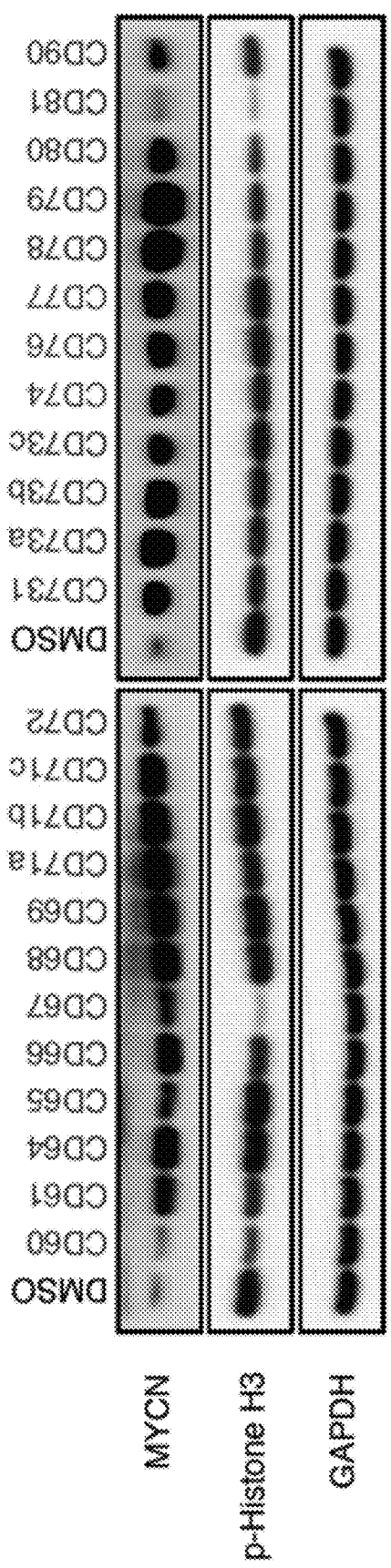
FIGS. 5A-D.
Figure 5B:
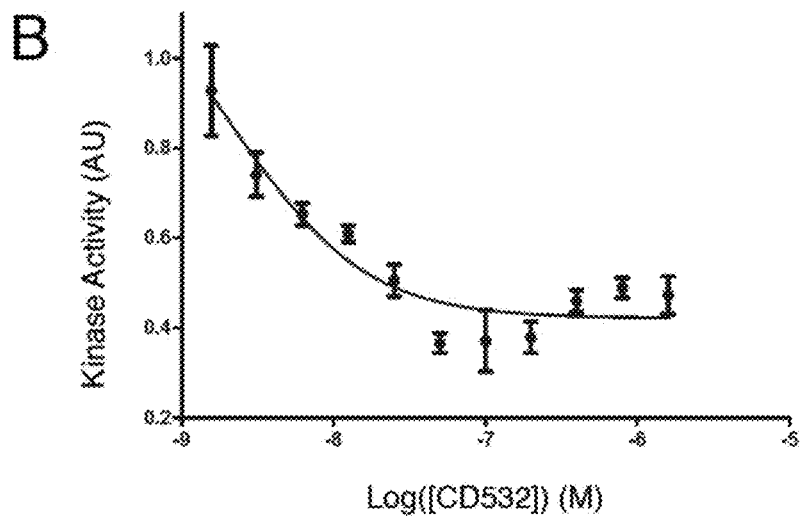
Figure 5C:
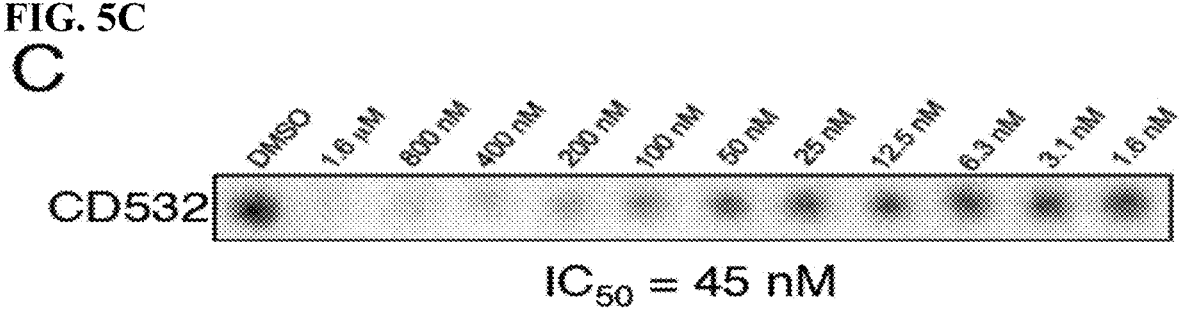
Figure 5D:
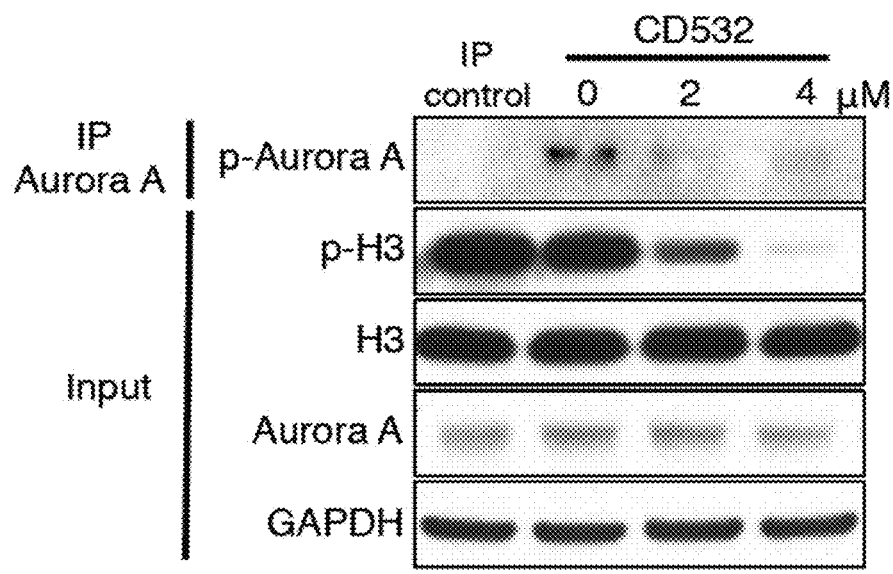

The difference in the kinetics of complex dissociation between CD532 and MLN8237 (FIGS. 14A-C), coupled with their respective $IC_{50}$ values and crystallographic information (FIGS. 5B, 5C and 3), sheds insight into the biophysical basis for disruption of the Aurora A-MYCN interaction. While MLN8237 is a potent inhibitor of Aurora A (4 nM), it only modestly disrupts the conformation of Aurora A (FIG. 4C). Thus, while MLN8237 inhibits Aurora A kinase activity at low concentrations, even saturating doses only partially disrupt the complex between Aurora and MYCN (FIG. 14C). In contrast, CD532 is a weaker inhibitor of Aurora Kinase A, however saturating doses lead to complete dissociation of the complex. Taken together with structural data, these observations suggest that the equilibrium of dissociation of the MYCN-Aurora A complex is dependent upon the degree of conformational disruption of Aurora A.

Several other inhibitors of Aurora kinase are in clinical development, all of which are act as mitotic poisons much like current cytotoxic chemotherapy agents. The functional data herein show that CD532 acts more as a potent MYCN inhibitor, rather than a conventional Aurora A inhibitor in neuroblastoma. And CD532 has potential to act as a c-MYC inhibitor in other cell types, as measured by cell line susceptibility profiling. While the pharmacokinetic properties of CD532 have not been optimized, CD532 effects loss of MYCN protein in neuroblastoma xenografts (FIGS. 13D and 13E), providing motivation for additional medicinal chemistry and optimization of this family of compounds for use in vivo.

Neuroblastoma is the most common extracranial solid tumor of childhood and MYCN amplification is the best-described genetic lesion marking high-risk, chemotherapy resistant disease. Targeted expression of MYCN drives neuroblastoma in systems from mice to zebrafish (Weiss et al., 1997; Zhu et al., 2012). Destabilization of MYCN was previously finessed through blockade of upstream PI3K/mTOR inhibition (Chanthery et al., 2012; Chesler et al., 2006) and through an alternative approach to block MYCN and its transcriptional targets is through use of BRD4-based bromodomain inhibitors (Puissant et al., 2013). Here is developed a third strategy to block MYCN in cancer. These interventions, at distinct nodes in the same oncogenic pathway, present a unique opportunity for combinatorial, targeted therapeutics to block emergent resistance, while maximizing the blockade of MYCN in neuroblastoma and potentially in other MYCN- and MYC-driven cancers.

Allostery is most generally defined as a phenomenon whereby a perturbation by an effector at one site of the molecule leads to a functional change at another through alteration of shape and/or dynamics (Nussinov and Tsai, 2013). There are several recent examples of allosteric inhibitors for the treatment of cancer including arsenic trioxide, an anti-leukemic which binds to zinc fingers within the PML-RARAα fusion protein of acute promyelocytic leukemia to induce a conformational change favoring oligomerization and eventual degradation (Dietrich et al., 2010; Filomia et al., 2010; Zhang et al., 2010) and biculutamide which binds to the androgen receptor to block transcription in prostate cancer (Osguthorpe and Hagler, 2011). Enzymes, including but not exclusive to kinases like Aurora A, may have important non-enzymatic activities including scaffolding, regulation, and localization of other proteins. As such, many molecular interactions necessary for cellular function and carcinogenesis are not targetable directly with small molecules, either because they have no amenable binding pocket (as with MYC proteins) or because their affinity for natural substrate is too high (as with many GTPases such as RAS). By contrast, orthosteric targeting of small molecules to enzymes like kinases has become relatively trivial. Here we refer to an ATP-mimetic ligand that binds the active site of Aurora A to alter its kinase-independent stabilization of MYCN, but also, obligately, its kinase activity. We have termed such inhibitors as "amphosteric", denoting an inhibitor that is simultaneously both orthosteric (inhibiting kinase activity) and allosteric (disrupting protein-protein interactions). Thus, CD532 represents the prototype of a new class of amphosteric inhibitors that induce an allosteric change to disrupt non-enzymatic functions of enzymes. As these amphosteric effects are neglected in most current inhibitor screening, development of small molecule screens for other amphosteric inhibitors has the potential to target other undruggable oncoprotein targets Kinome-Wide Profiling of Inhibitors Percent inhibition of individual kinases were generated with biochemical enzymatic kinase assays using the SelectScreen® Kinase Profiling Service (Life Technologies Corp, Madison, Wis.). Compounds were screened at 1 μM concentration and an ATP concentration equal to the ATP Km, app for the assay, unless otherwise noted in the detailed procedures described by Invitrogen (www.invitrogen.com/kinaseprofiling).

TABLE 1

Summary of data and refinement statistics for crystal structures solutions of Aurora A apo and Aurora A bound to CD532.

|  | Aurora Kinase A with CD532 | Aurora Kinase A Apo |
| --- | --- | --- |
| Resolution range (Å) | 29.07-1.853 (1.92-1.853) | 44.95-3.135 (3.247-3.135) |
| Space group | C 2 2 21 | P 31 |
| Unit cell | 83.175 92.943 74.542 90 90 90 | 83.783 83.783 171.777 90 90 120 |

TABLE 1-continued

Summary of data and refinement statistics for crystal structures solutions of Aurora A apo and Aurora A bound to CD532.

|  | Aurora Kinase A with CD532 | Aurora Kinase A Apo |
|---|---|---|
| Total reflections |  |  |
| Unique reflections | 24601 (2358) | 23663 (2375) |
| Multiplicity |  |  |
| Completeness (%) | 98.82 (96.05) | 99.95 (100.00) |
| Mean I/sigma(I) | 8.53 (2.50) | 18.99 (5.50) |
| Wilson B-factor | 28.16 | 95.57 |
| R-sym |  |  |
| R-factor | 0.1841 (0.2469) | 0.1845 (0.2838) |
| R-free | 0.2188 (0.2716) | 0.2344 (0.3634) |
| Number of atoms | 4657 | 17546 |
| macromolecules | 2190 | 8731 |
| ligands | 56 |  |
| water | 172 | 8 |
| Protein residues | 266 | 1063 |
| RMS(bonds) | 0.009 | 0.004 |
| RMS(angles) | 1.19 | 0.89 |
| Ramachandran favored (%) | 97 | 94 |
| Ramachandran outliers (%) | 0 | 0.95 |
| Clashscore | 9.21 | 13.49 |
| Average B-factor | 38 | 105 |
| macromolecules | 37.8 | 105.1 |
| solvent | 40.6 | 56.4 |

TABLE 2

Cancer cell lines profiled through the Genomics of Drug Sensitivity Project with calculated $EC_{50}$ values for CD532.

| Cell Line | Organ | CD532 $EC_{50}$ (uM) |
|---|---|---|
| A2058 | Skin | 0.975156787 |
| A2058 | Skin | 1.091672731 |
| WM-115 | Skin | 0.411713516 |
| WM793B | Skin | 0.705032914 |
| WM35 | Skin | 0.366955053 |
| RPMI-7951 | Skin | 1.061296515 |
| RPMI-7951 | Skin | 0.95218998 |
| M-14 | Skin | 0.971673219 |
| COLO-800 | Skin | 0.301755603 |
| IGR-1 | Skin | 0.269958538 |
| IGR-37 | Skin | 0.547080481 |
| IPC-298 | Skin | 0.574196164 |
| MEL-HO | Skin | 0.411287267 |
| MEL-JUSO | Skin | 0.782688747 |
| RVH-421 | Skin | 0.585150516 |
| SK-MEL-1 | Skin | 0.648516761 |
| SK-MEL-3 | Skin | 0.567429212 |
| SK-MEL-30 | Skin | 0.32287563 |
| A431 | Skin | 0.363711762 |
| HMVII | Skin | 0.746172079 |
| MEWO | Skin | 1.457417118 |
| AGS | Stomach | 0.345963592 |
| FU97 | Stomach | 0.544641492 |
| SNU-1 | Stomach | 0.158255292 |
| SNU-5 | Stomach | 2.510478463 |
| NCI-N87 | Stomach | 10.85335113 |
| MKN1 | Stomach | 0.859934099 |
| MKN45 | Stomach | 0.45603548 |
| MKN45 | Stomach | 0.260384039 |
| NUGC-3 | Stomach | 0.967961277 |
| NUGC-3 | Stomach | 1.151987365 |
| MKN28 | Stomach | 10.13383228 |
| HSC-39 | Stomach | 0.103017511 |
| 23132/87 | Stomach | 0.470858519 |
| HGC-27 | Stomach | 0.829810395 |
| SCH | Stomach | 1.239565973 |
| 8505C | Thyroid | 0.661984338 |
| B-CPAP | Thyroid | 0.739262663 |
| CAL-62 | Thyroid | 0.589115987 |
| HTC-C3 | Thyroid | 0.915150421 |
| ML-1 | Thyroid | 1.324660974 |
| A2058 | Skin | 0.975156787 |
| A2058 | Skin | 1.091672731 |
| WM-115 | Skin | 0.411713516 |
| WM793B | Skin | 0.705032914 |
| WM35 | Skin | 0.366955053 |
| RPMI-7951 | Skin | 1.061296515 |
| RPMI-7951 | Skin | 0.95218998 |
| M-14 | Skin | 0.971673219 |
| COLO-800 | Skin | 0.301755603 |
| IGR-1 | Skin | 0.269958538 |
| IGR-37 | Skin | 0.547080481 |
| IPC-298 | Skin | 0.574196164 |
| MEL-HO | Skin | 0.411287267 |
| MEL-JUSO | Skin | 0.782688747 |
| RVH-421 | Skin | 0.585150516 |
| SK-MEL-1 | Skin | 0.648516761 |
| SK-MEL-3 | Skin | 0.567429212 |
| SK-MEL-30 | Skin | 0.32287563 |
| A431 | Skin | 0.363711762 |
| HMVII | Skin | 0.746172079 |
| MEWO | Skin | 1.457417118 |
| AGS | Stomach | 0.345963592 |
| FU97 | Stomach | 0.544641492 |
| SNU-1 | Stomach | 0.158255292 |
| SNU-5 | Stomach | 2.510478463 |
| NCI-N87 | Stomach | 10.85335113 |
| MKN1 | Stomach | 0.859934099 |
| MKN45 | Stomach | 0.45603548 |
| MKN45 | Stomach | 0.260384039 |
| NUGC-3 | Stomach | 0.967961277 |
| NUGC-3 | Stomach | 1.151987365 |

TABLE 2-continued

Cancer cell lines profiled through the Genomics of Drug Sensitivity Project with calculated $EC_{50}$ values for CD532.

| Cell Line | Organ | CD532 $EC_{50}$ (uM) |
|---|---|---|
| MKN28 | Stomach | 10.13383228 |
| HSC-39 | Stomach | 0.103017511 |
| 23132/87 | Stomach | 0.470858519 |
| HGC-27 | Stomach | 0.829810395 |
| SCH | Stomach | 1.239565973 |
| 8505C | Thyroid | 0.661984338 |
| B-CPAP | Thyroid | 0.739262663 |
| CAL-62 | Thyroid | 0.589115987 |
| HTC-C3 | Thyroid | 0.915150421 |
| ML-1 | Thyroid | 1.324660974 |
| HN | Head & Neck | 1.626873697 |
| BICR 10 | Head & Neck | 4.266380535 |
| BICR 78 | Head & Neck | 12.17752254 |
| Detroit 562 | Head & Neck | 1.247870729 |
| DOK | Head & Neck | 0.511733031 |
| PE/CA-PJ15 | Head & Neck | 1.899177044 |
| RPMI 2650 | Head & Neck | 0.412439308 |
| HO-1-N-1 | Head & Neck | 1.674383846 |
| SCC-4 | Head & Neck | 0.883557985 |
| HO-1-u-1 | Head & Neck | 9.80501152 |
| SAT | Head & Neck | 1.189986258 |
| OSC-20 | Head & Neck | 1.234382794 |
| OSC-19 | Head & Neck | 1.183912689 |
| KON | Head & Neck | 4.1502558 |
| SAS | Head & Neck | 1.460669391 |
| HSC-2 | Head & Neck | 2.150386136 |
| HSC-3 | Head & Neck | 2.325849922 |
| HSC-4 | Head & Neck | 0.884566109 |
| Ca9-22 | Head & Neck | 0.704772916 |
| CL-11 | Intestine | 4.933601987 |
| 5637 | UrinaryTrack | 0.490051245 |
| BFTC-909 | Kidney | 1.508021081 |
| NH-12 | Nervous System | 0.370109406 |
| SNU-449 | Liver | 12.07979112 |
| SNU-423 | Liver | 0.753132993 |
| Hep 3B2.1-7 | Liver | 0.876980505 |
| SK-HEP-1 | Liver | 1.598524185 |
| JHH-4 | Liver | 1.354030443 |
| JHH-1 | Liver | 0.295113683 |
| JHH-2 | Liver | 0.542667827 |
| JHH-6 | Liver | 1.242482203 |
| JHH-7 | Liver | 0.766015566 |
| huH-1 | Liver | 1.375891495 |
| HLE | Liver | 0.566760045 |
| A101D | Skin | 0.429088943 |
| A253 | Head & Neck | 24.50959978 |
| ACN | Nervous System | 0.883652323 |
| BB30-HNC | Head & Neck | 0.462425117 |
| COLO-829 | Skin | 0.795960313 |
| DJM-1 | Skin | 0.42704984 |
| DSH1 | UrinaryTrack | 0.779342822 |
| GAK | Skin | 0.823290707 |
| GI-ME-N | Nervous System | 0.42754132 |
| GI-ME-N | Nervous System | 0.812075205 |
| GT3TKB | Stomach | 1.045914285 |
| HT-144 | Skin | 0.365659592 |
| IMR-5 | Nervous System | 0.007101352 |
| K5 | Thyroid | 1.327555382 |
| KP-N-YS | Nervous System | 0.27010772 |
| LB2518-MEL | Skin | 0.846564328 |
| LB2518-MEL | Skin | 0.708903527 |
| LB771-HNC | Head & Neck | 0.915951778 |
| LB831-BLC | UrinaryTrack | 1.289912617 |
| LB996-RCC | Kidney | 2.078254026 |
| LOXIMVI | Skin | 0.732283924 |
| LOXIMVI | Skin | 0.384387026 |
| LS-123 | Intestine | 0.861101678 |
| MMAC-SF | Skin | 0.565856815 |
| MZ2-MEL. | Skin | 0.434255207 |
| MZ7-mel | Skin | 0.730430209 |
| MZ7-mel | Skin | 0.555605134 |
| NB10 | Nervous System | 0.274985866 |
| NB12 | Nervous System | 0.292694801 |
| NB13 | Nervous System | 1.017631097 |
| NB17 | Nervous System | 0.281736626 |
| NB5 | Nervous System | 0.761324016 |
| NCI-H747 | Intestine | 0.664862571 |
| RL95-2 | Uterus | 0.334955988 |
| SH-4 | Skin | 0.782672274 |
| UACC-257 | Skin | 0.606530835 |
| KLE | Uterus | 2.993472634 |
| CP50-MEL-B | Skin | 0.323045044 |
| TT | Thyroid | 0.972479756 |
| RF-48 | Stomach | 0.902658876 |
| SK-MEL-5 | Skin | 0.524687487 |
| SK-MEL-5 | Skin | 0.365923321 |
| NBsusSR | Nervous System | 0.382267177 |
| SNU-61 | Intestine | 1.020798052 |
| SNU-81 | Intestine | 0.421313809 |
| EFO-21 | Ovary | 1.865638811 |
| OVMIU | Ovary | 0.868757618 |
| OVKATE | Ovary | 6.000259903 |
| HPAC | Pancreas | 2.496277553 |
| AsPC-1 | Pancreas | 5.405175405 |
| Hs, 766T | Pancreas | 2.446703814 |
| YAPC | Pancreas | 5.344712364 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

VIII. References

Adams, P. D., Afonine, P. V., Bunkoczi, G., Chen, V. B., Davis, I. W., Echols, N., Headd, J. J., Hung, L.-W., Kapral, G. J., Grosse-Kunstleve, R. W., et al. (2010). PHENIX: a comprehensive Python-based system for macromolecular structure solution. Acta Crystallogr. D Biol. Crystallogr. 66, 213-221.

Brockmann, M., Poon, E., Berry, T., Carstensen, A., Deubzer, H. E., Rycak, L., Jamin, Y., Thway, K., Robinson, S. P., Roels, F., et al. (2013). Small Molecule Inhibitors of Aurora-A Induce Proteasomal Degradation of N-Myc in Childhood Neuroblastoma. Cancer Cell.

Carmena, M., Ruchaud, S., and Earnshaw, W. C. (2009). Making the Auroras glow: regulation of Aurora A and B kinase function by interacting proteins. Curr. Opin. Cell Biol. 21, 796-805.

Carol, H., Boehm, I., Reynolds, C. P., Kang, M. H., Maris, J. M., Morton, C. L., Gorlick, R., Kolb, E. A., Keir, S. T., Wu, J., et al. (2011). Efficacy and pharmacokinetic/pharmacodynamic evaluation of the Aurora kinase A inhibitor MLN8237 against preclinical models of pediatric cancer. Cancer Chemotherapy and Pharmacology 68, 1291-1304.

Chanthery, Y. H., Gustafson, W. C., Itsara, M., Persson, A., Hackett, C. S., Grimmer, M., Charron, E., Yakovenko, S., Kim, G., Matthay, K. K., et al. (2012). Paracrine signaling through MYCN enhances tumor-vascular interactions in neuroblastoma. Sci Transl Med 4, 115ra3.

Chesler, L., Schlieve, C., Goldenberg, D. D., Kenney, A., Kim, G., McMillan, A., Matthay, K. K., Rowitch, D., and Weiss, W. A. (2006). Inhibition of phosphatidylinositol 3-kinase destabilizes Mycn protein and blocks malignant progression in neuroblastoma. Cancer Res 66, 8139-8146.

Crosio, C., Fimia, G. M., Loury, R., Kimura, M., Okano, Y., Zhou, H., Sen, S., Allis, C. D., and Sassone-Corsi, P. (2002). Mitotic phosphorylation of histone H3: spatiotemporal regulation by mammalian Aurora kinases. 22, 874-885.

Delmore, J. E., Issa, G. C., Lemieux, M. E., Rahl, P. B., Shi, J., Jacobs, H. M., Kastritis, E., Gilpatrick, T., Paranal, R. M., Qi, J., et al. (2011). BET Bromodomain Inhibition as a Therapeutic Strategy to Target c-Myc. Cell 146, 904-917.

Dietrich, J., Hulme, C., and Hurley, L. H. (2010). The design, synthesis, and evaluation of 8 hybrid DFG-out allosteric kinase inhibitors: a structural analysis of the binding interactions of Gleevec, Nexavar, and BIRB-796. 18, 5738-5748.

Dodson, C. A., Kosmopoulou, M., Richards, M. W., Atrash, B., Bavetsias, V., Blagg, J., and Bayliss, R. (2010). Crystal structure of an Aurora-A mutant that mimics Aurora-B bound to MLN8054: insights into selectivity and drug design. Biochem J 427, 19-28.

Emsley, P., Lohkamp, B., Scott, W. G., and Cowtan, K. (2010). Features and development of Coot. Acta Crystallogr. D Biol. Crystallogr. 66, 486-501.

Filippakopoulos, P., Qi, J., Picaud, S., Shen, Y., Smith, W. B., Fedorov, O., Morse, E. M., Keates, T., Hickman, T. T., Felletar, I., et al. (2010). Selective inhibition of BET bromodomains. Nature 468, 1067-1073.

Filomia, F., De Rienzo, F., and Menziani, M. C. (2010). Insights into MAPK p38alpha DFG flip mechanism by accelerated molecular dynamics. 18, 6805-6812.

Garnett, M. J., Edelman, E. J., Heidorn, S. J., Greenman, C. D., Dastur, A., Lau, K. W., Greninger, P., Thompson, I. R., Luo, X., Soares, J., et al. (2012). Systematic identification of genomic markers of drug sensitivity in cancer cells. Nature 483, 570-575.

Gogolin, S., Ehemann, V., Becker, G., Brueckner, L. M., Dreidax, D., Bannert, S., Nolte, I., Savelyeva, L., Bell, E., and Westermann, F. (2013). CDK4 inhibition restores G(1)-S arrest in MYCN-amplified neuroblastoma cells in the context of doxorubicin-induced DNA damage. Cell Cycle 12, 1091-1104.

Görgün, G., Calabrese, E., Hideshima, T., Ecsedy, J., Perrone, G., Mani, M., Ikeda, H., Bianchi, G., Hu, Y., Cirstea, D., et al. (2010). A novel Aurora-A kinase inhibitor MLN8237 induces cytotoxicity and cell-cycle arrest in multiple myeloma. Blood 115, 5202-5213.

Gustafson, W. C., and Weiss, W. A. (2010). Myc proteins as therapeutic targets. Oncogene 29, 1249-1259.

Harrington, E. A., Bebbington, D., Moore, J., Rasmussen, R. K., Ajose-Adeogun, A. O., Nakayama, T., Graham, J. A., Demur, C., Hercend, T., Diu-Hercend, A., et al. (2004). VX-680, a potent and selective small-molecule inhibitor of the Aurora kinases, suppresses tumor growth in vivo. Nat Med 10, 262-267.

Knight, Z. A., Feldman, M. E., Balla, A., Balla, T., and Shokat, K. M. (2007). A membrane capture assay for lipid kinase activity. Nat Protoc 2, 2459-2466.

Lin, C. Y., Lovén, J., Rahl, P. B., Paranal, R. M., Burge, C. B., Bradner, J. E., Lee, T. I., and Young, R. A. (2012). Transcriptional Amplification in Tumor Cells with Elevated c-Myc. Cell 151, 56-67.

Liu, Q., Kaneko, S., Yang, L., Feldman, R. I., Nicosia, S. V., Chen, J., and Cheng, J. Q. (2004). Aurora-A abrogation of p53 DNA binding and transactivation activity by phosphorylation of serine 215.279, 52175-52182.

Manfredi, M. G., Ecsedy, J. A., Chakravarty, A., Silverman, L., Zhang, M., Hoar, K. M., Stroud, S. G., Chen, W., Shinde, V., Huck, J. J., et al. (2011). Characterization of Alisertib (MLN8237), an investigational small-molecule inhibitor of aurora A kinase using novel in vivo pharmacodynamic assays. Clin Cancer Res 17, 7614-7624.

Maris, J. M., Morton, C. L., Gorlick, R., Kolb, E. A., Lock, R., Carol, H., Keir, S. T., Reynolds, C. P., Kang, M. H., Wu, J., et al. (2010). Initial testing of the aurora kinase A inhibitor MLN8237 by the Pediatric Preclinical Testing Program (PPTP). Pediatr Blood Cancer 55, 26-34.

Martin, M. P., Zhu, J.-Y., Lawrence, H. R., Pireddu, R., Luo, Y., Alam, R., Ozcan, S., Sebti, S. M., Lawrence, N. J., and Schonbrunn, E. (2012). A Novel Mechanism by Which Small Molecule Inhibitors Induce the DFG Flip in Aurora A. ACS Chem Biol.

Mertz, J. A., Conery, A. R., Bryant, B. M., Sandy, P., Balasubramanian, S., Mele, D. A., Bergeron, L., and Sims, R. J. (2011). Targeting MYC dependence in cancer by inhibiting BET bromodomains. 108, 16669-16674.

Mosse, Y. P., Lipsitz, E., Fox, E., Teachey, D. T., Maris, J. M., Weigel, B., Adamson, P. C., Ingle, M. A., Ahern, C. H., and Blaney, S. M. (2012). Pediatric Phase I Trial and Pharmacokinetic Study of MLN8237, an Investigational Oral Selective Small-Molecule Inhibitor of Aurora Kinase A: A Children's Oncology Group Phase I Consortium Study. Clinical Cancer Research 18, 6058-6064.

Nie, Z., Hu, G., Wei, G., Cui, K., Yamane, A., Resch, W., Wang, R., Green, D. R., Tessarollo, L., Casellas, R., et al. (2012). c-Myc Is a Universal Amplifier of Expressed Genes in Lymphocytes and Embryonic Stem Cells. 151, 68-79.

Nussinov, R., and Tsai, C.-J. (2013). Allostery in disease and in drug discovery. Cell 153, 293-305.

Osguthorpe, D. J., and Hagler, A. T. (2011). Mechanism of Androgen Receptor Antagonism by Bicalutamide in the Treatment of Prostate Cancer. Biochemistry 50, 4105-4113.

Otto, T., Horn, S., Brockmann, M., Eilers, U., Schüttrumpf, L., Popov, N., Kenney, A. M., Schulte, J. H., Beijersbergen, R., Christiansen, H., et al. (2009). Stabilization of N-Myc is a critical function of Aurora A in human neuroblastoma. Cancer Cell 15, 67-78.

Ouchi, M. (2004). BRCA1 Phosphorylation by Aurora-A in the Regulation of G2 to M Transition. 279, 19643-19648.

Prochownik, E. V., and Vogt, P. K. (2010). Therapeutic Targeting of Myc. 1, 650-659. Puissant, A., Frumm, S. M., Alexe, G., Bassil, C. F., Qi, J., Chanthery, Y. H., Nekritz, E. A., Zeid, R., Gustafson, W. C., Greninger, P., et al. (2013). Targeting MYCN in neuroblastoma by BET bromodomain inhibition. Cancer Discovery 3, 308-323.

Scrittori, L., Hans, F., Angelov, D., Charra, M., Prigent, C., and Dimitrov, S. (2001). pEg2 aurora-A kinase, histone H3 phosphorylation, and chromosome assembly in Xenopus egg extract. 276, 30002-30010.

Shang, X., Burlingame, S. M., Okcu, M. F., Ge, N., Russell, H. V., Egler, R. A., David, R. D., Vasudevan, S. A., Yang, J., and Nuchtern, J. G. (2009). Aurora A is a negative prognostic factor and a new therapeutic target in human neuroblastoma. Molecular Cancer Therapeutics 8, 2461-2469.

Soucek, L., Whitfield, J. R., Sodir, N. M., Masso-Valles, D., Serrano, E., Karnezis, A. N., Swigart, L. B., and Evan, G. I. (2013). Inhibition of Myc family proteins eradicates Kras driven lung cancer in mice. Genes Dev 27, 504-513.

Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proceedings of the National Academy of Sciences of the United States of America 102, 15545-15550.

Toyoshima, M., Howie, H. L., Imakura, M., Walsh, R. M., Annis, J. E., Chang, A. N., Frazier, J., Chau, B. N., Loboda, A., Linsley, P. S., et al. (2012). Functional genomics identifies therapeutic targets for MYC-driven cancer.

Weiss, W. A., Weiss, W. A., Aldape, K., Aldape, K., Mohapatra, G., Mohapatra, G., Feuerstein, B. G., Feuerstein, B. G., Bishop, J. M., and Bishop, J. M. (1997). Targeted expression of MYCN causes neuroblastoma in transgenic mice. Embo J 16, 2985-2995.

Wen, Q., Goldenson, B., Silver, S. J., Schenone, M., Dancik, V., Huang, Z., Wang, L.-Z., Lewis, T. A., An, W. F., Li, X., et al. (2012). Identification of regulators of polyploidization presents therapeutic targets for treatment of AMKL. Cell 150, 575-589.

Zhang, X. W., Yan, X. J., Zhou, Z. R., Yang, F. F., Wu, Z. Y., Sun, H. B., Liang, W. X., Song, A. X., Lallemand-Breitenbach, V., Jeanne, M., et al. (2010). Arsenic Trioxide Controls the Fate of the PML-RAR Oncoprotein by Directly Binding PML. Science 328, 240-243.

Zhao, B., Smallwood, A., Yang, J., Koretke, K., Nurse, K., Calamari, A., Kirkpatrick, R. B., and Lai, Z. (2008). Modulation of kinase-inhibitor interactions by auxiliary protein binding: crystallography studies on Aurora A interactions with VX-680 and with TPX2. Protein Sci 17, 1791-1797.

Zhu, S., Lee, J.-S., Guo, F., Shin, J., Perez-Atayde, A. R., Kutok, J. L., Rodig, S. J., Neuberg, D. S., Helman, D., Feng, H., et al. (2012). Activated ALK collaborates with MYCN in neuroblastoma pathogenesis. Cancer Cell 21, 362-373

What is claimed is:

1. A compound, or a pharmaceutically acceptable salt thereof, having the formula:

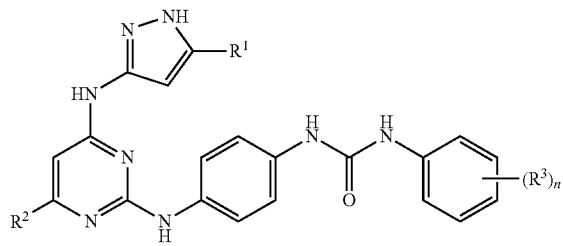

(I)

wherein $R^1$ is a substituted or unsubstituted $C_5$ cycloalkyl, substituted or unsubstituted 5 to 6 membered heteroaryl;

$R^2$ is hydrogen, halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCH$_3$, —OCF$_3$, —OCHF$_2$, —C(O)CH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCH$_3$, —OCF$_3$, —OCHF$_2$, —C(O)CH$_3$, unsubstituted alkyl, or unsubstituted heteroalkyl; and n is independently an integer from 0 to 5.

2. The compound of claim 1, wherein $R^1$ is an unsubstituted cyclopentyl or unsubstituted furanyl.

3. The compound of claim 1, wherein $R^2$ is hydrogen, halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCH$_3$, —OCF$_3$, —OCHF$_2$, —C(O)CH$_3$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

4. The compound of claim 1, wherein $R^2$ is hydrogen or unsubstituted $C_1$-$C_4$ alkyl.

5. The compound of claim 1, wherein $R^3$ is independently halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCH$_3$, —OCF$_3$, —OCHF$_2$, —C(O)CH$_3$, unsubstituted $C_1$-$C_4$ alkyl, or unsubstituted 2 to 4 membered heteroalkyl.

6. The compound of claim 1, wherein the compound has the formula:

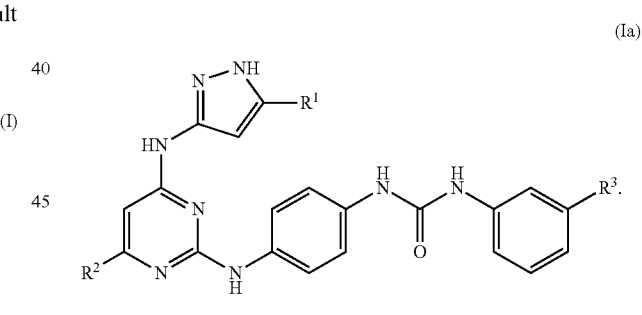

(Ia)

7. The compound of claim 1, wherein the compound has the formula:

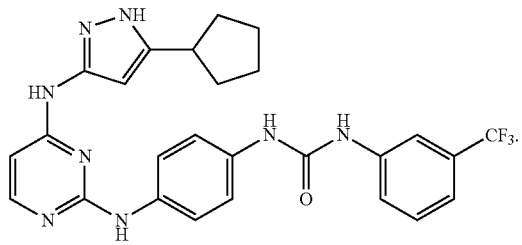 [SMILES: O=C(Nc1ccc(Nc2nccc(Nc3cc(C4CCCC4)[nH]n3)n2)cc1)Nc1cccc(C(F)(F)F)c1]

8. A pharmaceutical composition, comprising a pharmaceutically acceptable excipient and a compound, or a pharmaceutically acceptable salt thereof, of claim 1.

9. The compound of claim 1, wherein $R^1$ is a substituted or unsubstituted $C_5$ cycloalkyl.

10. The compound of claim 9, wherein $R^1$ is unsubstituted cyclopentyl.

* * * * *